US006277879B1

(12) United States Patent
Xu et al.

(10) Patent No.: US 6,277,879 B1
(45) Date of Patent: *Aug. 21, 2001

(54) CALANOLIDE ANALOGUES AND METHODS OF THEIR USE

(75) Inventors: Ze-Qi Xu, Naperville; Michael T. Flavin, Darien; David Zembower, Oak Park, all of IL (US)

(73) Assignee: Sarawak Medichem Pharmaceuticals, Inc., Lemont, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 14 days.

(21) Appl. No.: 09/173,143

(22) Filed: Oct. 15, 1998

Related U.S. Application Data

(63) Continuation-in-part of application No. 08/609,537, filed on Mar. 1, 1996, now Pat. No. 5,892,060, which is a continuation-in-part of application No. 08/510,213, filed on Aug. 2, 1995, now Pat. No. 6,043,271, which is a continuation-in-part of application No. 08/285,655, filed on Aug. 3, 1994, now Pat. No. 5,489,697.

(51) Int. Cl.$^7$ .......................... A61K 31/35; C07D 311/78

(52) U.S. Cl. .......................... 514/453; 549/277; 549/278

(58) Field of Search .......................... 514/453; 549/277, 549/278

(56) References Cited

U.S. PATENT DOCUMENTS

| 4,601,987 | 7/1986 | Klibanov et al. | 435/280 |
|---|---|---|---|
| 5,010,012 | 4/1991 | Wulbrandt et al. | 435/280 |
| 5,447,865 | 9/1995 | Wong et al. | 435/280 |
| 5,489,697 | 2/1996 | Boulanger et al. | 549/278 |
| 5,591,770 | 1/1997 | Boyd et al. | 514/453 |
| 5,608,085 | 3/1997 | Baker et al. | 549/277 |
| 5,723,631 | 3/1998 | Patil et al. | 549/277 |
| 5,840,921 | 11/1998 | Flavin et al. | 549/282 |
| 5,843,990 | 12/1998 | Baker et al. | 514/455 |
| 5,847,164 | 12/1998 | Flavin et al. | 549/277 |
| 5,859,049 | 1/1999 | Boyd et al. | 514/453 |
| 5,859,050 | 1/1999 | Flavin et al. | 514/453 |
| 5,869,324 | 2/1999 | Flavin et al. | 435/280 |
| 5,872,264 | 2/1999 | Flavin et al. | 549/277 |
| 5,874,591 | 2/1999 | Flavin et al. | 549/282 |
| 5,892,060 | 4/1999 | Flavin et al. | 549/277 |

FOREIGN PATENT DOCUMENTS

| 0 699 202 B1 | 3/1999 | (EP) . |
|---|---|---|
| WO 92/06695 | 4/1992 | (WO) . |
| WO 93/20082 | 10/1993 | (WO) . |
| WO 94/14789 | 7/1994 | (WO) . |
| WO 94/28000 | 12/1994 | (WO) . |

OTHER PUBLICATIONS

Brookmeyer, R. (1991), *Science*, vol. 253, pp. 37–42.
Braun et al. (1990), *Annu. Rev. Microbiol.*, vol. 44, pp. 555–577.
Weislow et al. (1989), *J. Natl. Cancer Inst.*, vol. 81, 577–586.
Mitsuya et al. (1990), *Science*, vol. 249, pp. 1533–1544.
Petteway et al. (1991), *Trends Pharmacol. Sci.*, vol. 12, pp. 28–34.
Richman, D.D. (1991), *Annu. Rev. Med.*, vol. 42, pp. 69–90.
De Clercq, E. (1992), *AIDS Research and Human Retroviruses*, vol. 8, pp. 119–134.
Kashman et al. (1992), *J. Med. Chem.*, vol. 35, pp. 2735–2743.
Chenera et al. (1993), *J. Org. Chem.*, vol. 58, pp. 5605–5606.
Sethna et al. (1953), *Organic Reactions*, Chapter 1, pp. 1–58.
Crombie et al. (1987), *Chem. Soc.*, vol. 1, pp. 317–333.
Barton et al. (1990), *Tetrahedron Letters*, vol. 31, pp. 7449–7452.
Széll et al. (1969), *Helvetica Chimica Acta*, vol. 52, pp. 2636–2641.
Fung et al. (1978), *J. Org. Chem.*, vol. 43, pp. 3977–3979.
Gemal et al. (1981), *J. Am. Chem. Soc.*, vol. 103, pp. 5454–5459.
Palmer et al. (1994), *Tet. Letters*, vol. 35, pp. 5363–5366.
Kashman et al. (1992), *J. Med. Chem.*, vol. 35, pp. 2735–2743.
Games et al. (1972), *Tet. Letters*, vol. 31, pp. 3187–3190.
Crombie et al. (1966), *Tet. Letters*, vol. 2, pp. 151–156.
Hizi et al. (1993), *Antimicrobial Agents and Chemotherapy*, vol. 37, pp. 1037–1042.
Buckheit et al. (1995), *Antiviral Research*, vol. 26, pp. 117–132.
Buckheit et al. (1995), *Virology*, vol. 210, pp. 186–193.
Boyer et al. (1993), *J. Virology*, vol. 67, pp. 2412–2420.
McKee et al. (1995), *J. Natural Products*, vol. 58, pp. 916–920.
Kucherenko et al. (1995), *Tet. Letters*, vol. 36, pp. 5475–5478.
Gustafson et al. (1994), *Tet. Letters*, vol. 35, pp. 5821–5824.
Kashman et al. (1993), *J. Med. Chem.*, vol. 36, p. 1110.
Bader et al. (1991), *Proc. Natl. Acad. Sci. USA*, vol. 88, pp. 6740–6744.

(List continued on next page.)

*Primary Examiner*—Amelia Owens
(74) *Attorney, Agent, or Firm*—McDonnell, Boehnen, Hulbert & Berghoff

(57) ABSTRACT

Calanolide analogues that demonstrate potent antiviral activity against many viruses are provided. Also provided is a method of using calanolide analogues for treating or preventing viral infections. The calanolide analogues provided are obtained via syntheses employing chromene 4 and chromanone 7 as key intermediates.

114 Claims, 28 Drawing Sheets

OTHER PUBLICATIONS

Borch et al. (1971), *J. Amer. Chem. Soc.*, vol. 93, pp. 2897–2904.
Buckheit et al. (1994), *Antiviral Chemistry & Chemotherapy*, vol. 5(1), pp. 35–42.
Castro, B.R. (1983), *Org. React.*, vol. 29, pp. 1–162.
Feuer et al. (1965), *J. Org. Chem.*, vol. 30, pp. 2877–2880.
Feuer and Braunstein (1969), *J. Org. Chem.*, vol. 34, pp. 1817–1821.
Hudlicky, M. (1988), *Org. React.*, vol. 35, pp. 513–637.
Hughes, D.L. (1992), *Organic Reaction*, vol. 42, pp. 335–656.
Kukla et al. (1991), *J. Medicinal Chemistry*, vol. 34, pp. 746–751.
Lin et al. (1994), *J. Med. Chem.*, vol. 37, pp. 798–803.
Massa et al. (1995), *Antiviral Chemistry and Chemotherapy*, vol. 6, pp. 1–8.
Mayaux et al. (1994), *Proc. Natl. Acad. Sci. USA*, vol. 91, pp. 3564–3568.
McGuigan et al. (1994), *Antiviral Research*, vol. 24, pp. 69–77.
McMahon et al. (1993), *Antimicrobial Agents and Chemotherapy*, vol. 37, pp. 754–760.
Meier et al. (1992) *J. Org. Chem.*, vol. 57, pp. 7300–7308.
Merluzzi et al. (1990), *Science*, vol. 250, pp. 1411–1413.
Mitsunobu, O. (1981), *Synthesis*, pp. 1–28.
Miyasaka et al. (1989), *J. Medicinal Chemistry*, vol. 32, pp. 2507–2509.
Nielsen and Houlihan (1968), *Org. React.*, vol. 16, pp. 1–438.
Pauwels et al. (1990), *Nature*, vol. 343, pp. 470–474.
Pauwels et al. (1988), *J. Virological Methods*, vol. 309–321.
Sergheraert et al. (1993), *J. Medicinal Chemistry*, vol. 36, pp. 826–830.
Wasserman et al. (1989), *Tet. Letters*, vol. 30, pp. 1721–1724.
Bandara et al. (1986), *Phytochemistry*, vol. 25, pp. 425–428.
Boyd, M., "AIDS: Etiology, Diagnosis Treatment and Prevention," Chapter 18, 2nd Ed., J.B. Lippincott Co., Devita et al., ed., pp. 305–317.
Chaturvedi et al. (1974), *Res. Communications in Chemical Pathology and Pharmacology*, vol. 9, pp. 11–22.
Craig et al. (1991), *Antiviral Research*, vol. 16, pp. 295–305.
Dahanayake et al. (1974), *J.C.S. Perkin I*, pp. 2510–2514.
Dharmaratne et al. (1985), *Phytochemistry*, vol. 24, pp. 1553–1556.
Dharmaratne et al. (1986), *Phytochemistry*, vol. 25, pp. 1957–1959.
Gautier et al. (1972), *Tetrahedron Letters*, vol. 27, pp. 2715–2718.
Gunasekera et al. (1977), *J.C.S. Perkin I*, pp. 1505–1511.
Gunasekera et al. (1975), *J.C.S. Perkin I*, pp. 2215–2220.
Gunatilaka et al. (1984), *Phytochemistry*, vol. 23, pp. 323–328.
Gustafson et al. (1992), *J. Med. Chem.*, vol. 35, pp. 1978–1986.
Gustafson et al. (1992), *Natural Products as Antiviral Agents*, Chu et al., eds. Plenum Press, New York, 1992, pp. 57–67.
Kawazu et al. (1972), *Chemical Abstracts*, vol. 78, Abstract No. 13744F.
Kumar et al. (1982), *Phytochemistry*, vol. 21, pp. 807–809.
Merigan et al. (1991), *Am. J. of Medicine*, vol. 90, pp. 8S–17S.
McCaffrey et al. (1988), *In Vitro Cellular & Developmental Biology*, vol. 24, Part I, pp. 247–252.
Ohtani et al. (1991), *J. Org. Chem.*, vol. 56, pp. 1296–1298.
Ohtani et al. (1989), *Tetrahedron Letters*, vol. 30, pp. 3147–3150.
Pauwels et al. (1992), *Nature*, vol. 343, pp. 470–474.
Rink et al. (1982), *J. of Cell Biology*, vol. 95, pp. 189–196.
Samaraweera et al. (1981), *Tetrahedron Letters*, vol. 22, pp. 5083–5086.
Saunders et al. (1992), *Drug Design and Discovery*, vol. 8, pp. 255–263.
Shih et al. (1991), *Proc. Natl. Acad. Sci. USA*, vol. 88, pp. 9878–9882.
Stout et al. (1968), *J. Organic Chemistry*, vol. 33, pp. 4185–4190.
Stout et al. (1964), *J. Organic Chemistry*, vol. 29, pp. 3604–3609.
Swagler et al. (1991), *J. Pharm. Pharmacol.*, vol. 43, pp. 823–826.
Soejarto et al. (1993), *Proceedings of the Symposium on the Industrial Utilization of Tropical Plants and the Conservation of Biodiversity*, Enugu, Nigeria, Feb. 14–19, 1993.
Somanathan et al. (1974), *J.C.S. Perkin I*, pp. 2515–2517.
White et al. (1991), *Antiviral Research*, vol. 16, pp. 257–266.
Cragg et al. (1993), *Proceedings of the Symposium on the Industrial Utilization of Tropical Plants and the Conservation of Biodiversity*, Enugu, Nigeria, Feb., 14–19.
Hertzberg et al. (1993), *Programs and Abstracts of the Third International Conference on the Biotechnology of Microbial Products: Novel Pharmacological and Agrobiological Activities*, P–42, Apr. 27, 1993.
Hertzberg et al. (1993), *Programs and Abstracts of the Third International Conference on the Biotechnology of Microbial Products: Novel Pharmacological and Agrobiological Activities*, S–9, 17, Apr. 1993.
Mabberley, D.J. (1987), *The Plant Book*, Cambridge University Press, p. 92.
Patil et al. (1993), *Programs and Abtracts of the Third International Conference on the Biotechnology of Microbial Products: Novel Pharmacological and Agrobiological Activities*, P–31, Apr. 26, 1993.
Crombie et al. (1985), Synthesis of Mammeins and Surangin A, *Tet. Letters*, vol. 26, pp. 2929–2932.
Khilevich et al., (1996) *Chemical Abstracts*, vol. 125, No. 21, Abstract No. 275454.
Khilevich et al., (1996) "Synthesis of (+)–Calanolide A. and anti–HIV agent, via enzyme catalized resolution of the aldol products." *Tethedron Asymmetry*, vol. 7, No. 11, pp. 3315–3326.
Palmer et al., (1995) "Synthesis of the Calophyllum Coumarines. Part 2," *Journal Of The Chemical Society, Perkin Trans I.*, pp. 3135–3152.
Rehder et al., (1996) *Chemical Abstracts*, vol. 125, No. 23, Abstract No. 300646.
Galinis et al., (1996) *Journal of Medicinal Chemistry*, vol. 39, pp. 4507–4510.
Zembower et al., (1997) *Journal of Medicinal Chemistry*, vol. 40, No. 6, pp. 1005–1017.
Hadden, J.W. (1991), *Trends Pharmacol. Sci.*, vol. 12, pp. 107–111.
Cooper et al. (1994), GR15987 and Related Analogues as Highly Potent, Orally Active Non–Peptide Neurokinin $NK_2$ Receptor Antagonists, *Bioorganic & Med. Chem. Lett.*, vol. 4, pp. 1951–1956.

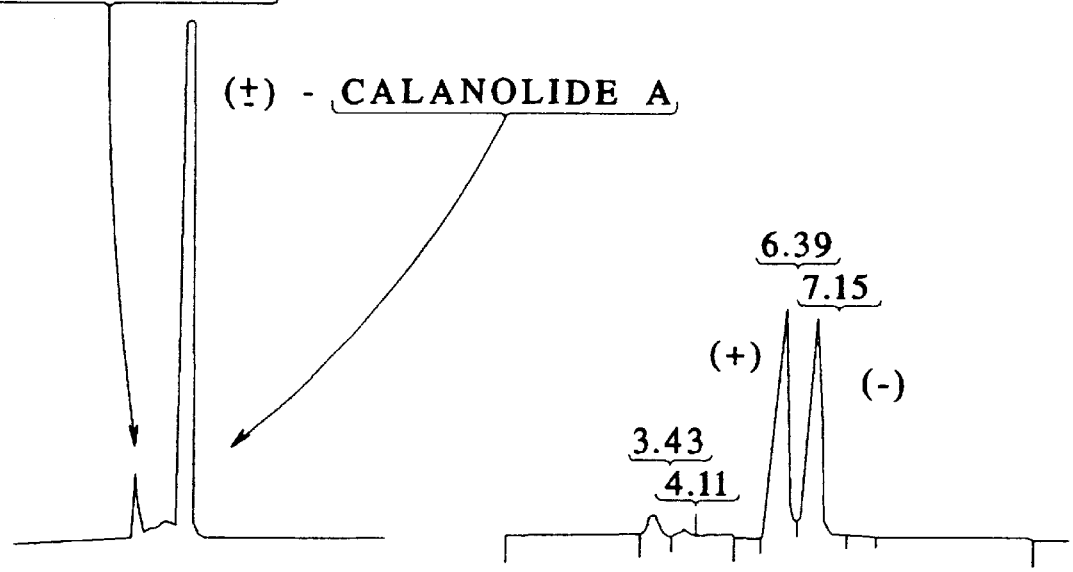
FIG. 6A
FIG. 6B
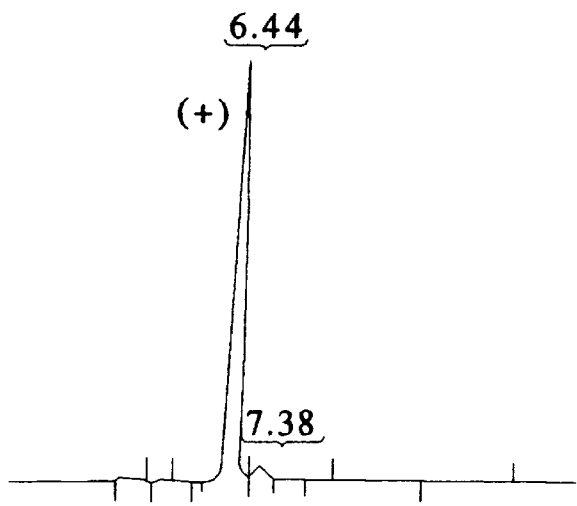
FIG. 6C
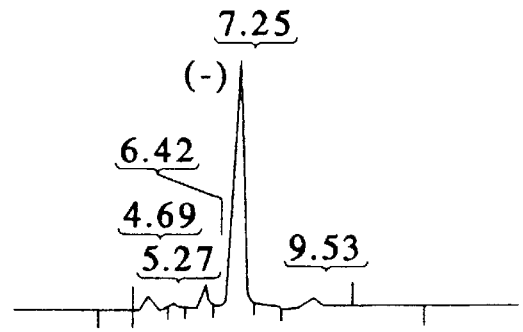
FIG. 6D

CALANOLIDE ANALOGUES AND METHODS OF THEIR USE

CROSS-REFERENCE

This is a continuation-in-part of U.S. patent application Ser. No. 8/609,537, filed Mar. 1, 1996, now U.S Pat. No. 5,892,060, issued Apr. 6, 1999, which is a continuation-in-part of U.S. patent application Ser. No. 08/510,213, filed Aug. 2, 1995, now U.S. Pat. No. 6,043,271, issued Mar. 28, 2000, which in turn is a continuation-in-part of U.S. patent application Ser. No. 08/285,655, filed Aug. 3, 1994, now U.S. Pat. No. 5,489,697 issued Feb. 6, 1996.

The work reported in this application has been supported, in part, by Grant No. 1 R43 AI/DA 41785-01 ZRG5 from the National Institute of Allergy and Infectious Diseases (NIAID), NIH. Accordingly, the United States Government has certain rights to the invention.

FIELD OF THE INVENTION

This invention relates to calanolide analogues that demonstrate potent antiviral activity against a spectrum of viruses. This invention also relates to the use of calanolide analogues for treating or preventing viral infections.

BACKGROUND OF THE INVENTION

Viruses, an important etiologic agent in infectious disease in humans and other mammals, are a diverse group of infectious agents that differ greatly in size, shape, chemical composition, host range, and effects on hosts. After several decades of study, only a limited number of antiviral agents are available for the treatment and/or prevention of diseases caused by viruses such as HIV, hepatitis B, herpes simplex type 1 and 2, cytomegalovirus, varicella zoster virus, Epstein Barr virus, influenza A and B, parainfluenza, adenovirus, measles, and respiratory syncytial virus. Because of their toxic effects on a host, many antiviral agents are limited to topical applications. Accordingly, there is a need for safe and effective antiviral agents with a wide-spectrum of anti-viral activity with reduced toxicity to the host.

A. Human Immunodeficiency Virus (HV)

Human immunodeficiency virus (HIV), which was also called human T-lymphotropic virus type III (HTLV-III), lymphadenopathy-associated virus (LAV) or AIDS-associated retrovirus (ARV), was first isolated in 1982 and has been identified as the etiologic agent of the acquired immunodeficiency syndrome (AIDS) and related diseases. Since then, chemotherapy of AIDS has been one of the most challenging scientific endeavors. So far, eleven drugs have been approved by FDA and are being clinically used as drugs for the treatment of AIDS and AIDS-related complex. Although these FDA-approved drugs can extend the life of AIDS patients and improve their quality of life, none of these drugs are capable of curing the disease. Bone-marrow toxicity and other side effects as well as the emergence of drug-resistant viral strains limit the long-term use of these agents.[1] On the other hand, the number of AIDS patients worldwide has increased dramatically within the past decade and estimates of the reported cases in the very near future also continue to rise dramatically. It is therefore apparent that there is a great need for other promising drugs having improved selectivity and activity to combat AIDS.[1] Several approaches including chemical synthesis, natural products screening, and biotechnology have been utilized to identify compounds targeting different stages of HIV replication for therapeutic intervention.[2]

Very recently, the screening program at the National Cancer Institute has discovered a class of remarkably effective anti-HIV natural products, named calanolides, from the rain forest tree *Calophyllum lanigerum,* with calanolide A, 1, being the most potent compound in the reported series.[3] For example, calanolide A demonstrated 100% protection against the cytopathic effects of HIV-1, one of two distinct types of HV, down to a concentration of 0.1 $\mu$M. This agent also halted HIV-1 replication in human T-lymphoblastic cells (CEM-SS)(EC$_{50}$=0.1 $\mu$M/IC$_{50}$=20 $\mu$M).[3] More interestingly and importantly, calanolide A was found to be active against both the AZT-resistant G-9106 strain of HIV as well as the pyridinone-resistant A17 virus.[3]

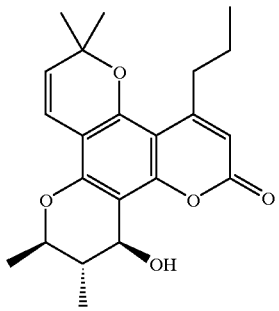

Thus, the calanolides, known as HIV-1 specific reverse transcriptase inhibitors, represent novel anti-HIV chemotherapeutic agents for drug development.

B. Hepatitis B Virus (HBV)

The hepatitis B virus (HBV) infects people of all ages. It is one of the fastest-spreading sexually transmitted diseases, and also can be transmitted by sharing needles or by behavior in which a person's mucus membranes are exposed to an infected person's blood, semen, vaginal secretions, or saliva. While the initial sickness is rarely fatal, ten percent of the people who contract hepatitis are infected for life and run a high risk of developing serious, long-term liver diseases, such as cirrhosis of the liver and liver cancer, which can cause serious complications or death.[21] The World Health Organization lists HBV as the ninth leading cause of death. It is estimated that about 300 million persons are chronically infected with HBV worldwide, with over 1 million of those in the United States. The Center for Disease Control and Prevention estimates that over 300,000 new cases of acute HBV infection occurs in the United States each year, resulting in 4,000 deaths due to cirrhosis and 1,000 due to hepatocellular carcinoma.[22] The highest rates of HBV infections occur in Southeast Asia, South Pacific Islands, Sub-Saharan Africa, Alaska, Amazon, Bahai, Haiti, and the Dominican Republic, where approximately 20% of the population is chronically infected.[23]

Hepatitis B virus (HBV) infection is currently the most important chronic virus infection, but no safe and effective therapy is available at present. The major therapeutic option for carriers of HBV is alpha interferon, which can control active virus replication. However, even in the most successful studies, the response rate in carefully selected patient groups has rarely exceeded 40%.[24,25] One of the reasons cited for interferon failure is the persistence of viral super-coiled DNA in the liver.[26] Clinical exploration of many promising antiviral agents such as nucleoside analogues is hampered because their aspecific body distribution leads to significant toxic side effects. Recently, however, a new nucleoside analogue, 2',3'-dideoxy-3'-thiacytidine (3TC), was discovered and found to be extremely potent against HBV replication with only minimal side effects.[27–29]

C. Influenza Virus

Influenza is a viral infection marked by fever, chills, and a generalized feeling of weakness and pain in the muscle, together with varying signs of soreness in the respiratory tract, head, and abdomen. Influenza is caused by several types of myxoviruses, categorized as groups A, B, and $C_4$. These influenza viruses generally lead to similar symptoms but are completely unrelated antigenically, so that infection with one type confers no immunity against the other. Influenza tends to occur in wavelike epidemics throughout the world; influenza A tends to appear in cycles of two to three years and influenza B in cycles of four to five years. Influenza is one of the few common infectious diseases that are poorly controlled by modem medicine. Its annual epidemics are occasionally punctuated by devastating pandemics. For example, the influenza pandemic of 1918, which killed over 20 million people and affected perhaps 100 times that number, was the most lethal plague ever recorded. Since that time, there have been two other pandemics of lesser severity, the so-called Asian flu of 1957 and the Hong Kong flu of 1968. All of these pandemics were characterized by the appearance of a new strain of influenza virus to which the human population had little resistance and against which previously existing influenza virus vaccines were ineffective. Moreover, between pandemics, influenza virus undergoes a gradual antigenic variation that degrades the level of immunological resistance against renewed infection.[30]

Anti-influenza vaccines, containing killed strains of types A and B virus currently in circulation, are available, but have only a 60 to 70% success rate in preventing infection. The standard influenza vaccine has to be redesigned each year to counter new variants of the virus. In addition, any immunity provided is short-lived. The only drugs currently effective in the prevention and treatment of influenza are amantadine hydrochloride and rimantadine hydrochloride.[31–33] While the clinical use of amantadine has been limited by the excess rate of CNS side effects, rimantadine is more active against influenza A both in animals and human beings, with fewer side effects.[34,35] It is the drug of choice for the chemoprophylaxis of influenza A.[30,36,37] However, the clinical usefulness of both drugs is limited by their effectiveness against only influenza A viruses, by the uncertain therapeutic efficacy in severe influenza, and by the recent findings of recovery of drug-resistant strains in some treated patients.[38–42] Ribavirin has been reported to be therapeutically active, but it remains in the investigational stage of development.[43,44]

D. Cytomegalovirus (CMV)

Cytomegalovirus (CMV) is a member of the herpes virus family, other well-known members of which include herpes simplex virus, types I and II, Epstein Barr virus and Varicella Zoster virus. Although these viruses are related taxonomically, all comprising double-stranded DNA viruses, infections due to these viruses manifest in clinically distinct ways. In the case of CMV, medical conditions arising from congenital infection include jaundice, respiratory distress and convulsive seizures that may result in mental retardation, neurologic disability or death. Infection in adults is frequently asymptomatic, but may manifest as mononucleosis, hepatitis, pneumonitis or retinitis, particularly in immunocompromised patients such as AIDS sufferers, chemotherapy patients and organ transplant patients undergoing tissue rejection therapy.

Up to 45% of all HIV-infected persons will develop cytomegalovirus-induced disease before their lives end.[45] Although two antiviral agents—ganciclovir and foscavir—are available to treat human cytomegalovirus (HCMV), they act as virustatic agents to slow but not halt progression of disease; hence, disease routinely progresses despite daily maintenance with either agent. Moreover, therapy using either agent is problematic because both agents are associated with serious toxicities.[46]

Classical drug therapies have generally focused upon interactions with proteins in efforts to modulate their disease-causing or disease-potentiating functions. Such therapeutic approaches have failed for cytomegalovirus infections. Effective therapy for CMV has not yet been developed despite studies on a number of antiviral agents. Interferon, transfer factor, adenine arabinoside (Ara-A), acycloguanosine (Acyclovir) and certain combinations of these drugs have been ineffective in controlling CMV infections. Based on preclinical and clinical data, foscarnet and ganciclovir show limited potential as antiviral agents. Foscarnet treatment has resulted in the resolution of CMV retinitis in five AIDS patients to date. Ganciclovir studies have shown efficacy against CMV retinitis and colitis. However, though ganciclovir seems to be well tolerated by most treated individuals, the appearance of a reversible neutropenia, the emergence of resistant strains of CMV upon long-term administration, and the lack of efficacy against CMV pneumonitis limit the long term applications of this compound. The development of more effective and less toxic therapeutic compounds and methods is needed for both acute and chronic use.

Several HCMV vaccines have been developed or are in the process of development. Vaccines based on live attenuated strains of HCMV have been described. A proposed HCMV vaccine using a recombinant vaccinia virus expressing HCMV glycoprotein B has also been described. However, vaccinia models for vaccine delivery are believed to cause local reactions. Additionally, vaccinia vaccines are considered possible causes of encephalitis.

E. Other Herpes Viruses

Varicella zoster virus (VZV) is the etiologic agent that produces both varicella (chickenpox) and zoster (shingles). As with other herpes viruses, VZV causes both an acute illness and lifelong latent infection. Acute primary infection (varicella) typically occurs during childhood, where the resulting infection is relatively mild. Conversely, primary infection in adults can be more severe. Herpes zoster cutaneous eruptions are caused by reactivation of VZV present in sensory ganglia.[47] Herpes zoster occurs more frequently with elderly and immunosuppressed individuals, and is eight times more likely to develop in HIV-infected individuals than in other individuals in comparable age groups.[41]

Along with other immunosuppressed patients, HIV-infected patients may develop severe and in certain cases life-threatening illnesses following either primary or recurrent VZV infection. Therapy for HIV-infected patients experiencing VZV infection generally involves administering acyclovir or vidarabine (Ara-A), with hospitalization required in many instances. To inhibit VZV replication, serum levels of acyclovir are about ten times greater than those needed to inhibit Herpes Simplex Type 1 and 2.

Herpes simplex virus type 1 and type 2 (HSV-1 and HSV-2) can establish latency following primary infection and can thus subsequently reactivate to induce recurrent disease. Upon primary infection, herpes simplex type 1 induces diseases including primary gingivostomatitis, encephalitis, and kerato-conjunctivitis, while herpes simplex type 2 induces primary genital herpes and neonatal herpes. Upon recurrence, herpes simplex type 1 induces diseases including recurrent oral herpes and recurrent kerato-conjunctivitis, while herpes simplex type 2 induces recurrent genital herpes.[49] HSV infection in HIV-infected patients can produce widespread and occasionally life-threatening lesions.

Acyclovir, delivered either intravenously, orally, or topically, shortens clinical illness in both immunocompetent and immunosuppressed patients. Vidarabine also has been used in treating HSV. Some vaccine strategies have been investigated with a view towards preventing initial primary infection. However, protecting only against primary disease but not protecting against latency and subsequent recurrence is inadequate for those persons already initially infected. Moreover, acyclovir-resistant HSV infections recently have been observed, in many cases occurring among HIV-infected patients treated successfully with acyclovir in the past. The existence of such acyclovir-resistant infections in HIV-infected patients is troubling in view of the limited number of alternative therapeutic options available.

Respiratory Syncytial Virus (RSV) is the prime etiologic agent producing lower respiratory tract disease. RSV causes extensive yearly epidemics during which there is a marked increase in hospital admissions of patients, especially infants and young children, experiencing severe lower respiratory tract disease. Immunosuppressed patients infected with RSV are at high risk of mortality. Ribavirin is the only currently approved drug for treating RSV infections. However, this drug appears to have limited efficacy. Additionally, development of effective vaccines has proven difficult to date.

F. Opportunistic Infections

The viruses above can act as sole causes of infection or can act to produce opportunistic infections in patients already battling immunosuppressing infections such as HIV. Acting by themselves, these viruses can present therapeutic challenges. But when acting to produce opportunistic infections in HIV-infected or otherwise inununosuppressed patients, these viruses dramatically increase the difficulty and complexity of successful treatment.

In addition to the viruses discussed above, other viral, bacterial, fungal, and protozoal pathogens can induce opportunistic infections. Common opportunistic pathogens in addition to those described above include *Mycobacterium avium* complex (MAC), *Pneumocystis carinii* (PC), and *M tuberculosis*.

Present therapies for HIV-infected patients also suffering from opportunistic infection generally involve administering a plurality of antiviral compounds. In such a treatment regimen, termed combination therapy, each antiviral compound employed demonstrates best antiviral activity against a distinct viral infection. For example, a combination therapy of AZT and ganciclovir can be used for an HIV-infected patient also experiencing CMV retinitis, where AZT targets the HIV infection and ganciclovir targets the CMV infection. Thus, combination therapies can be powerful therapeutic tools. Even more powerful and desirable, however, would be a single antiviral compound that demonstrates antiviral activity against both HIV and other viruses.

While some limited success has been realized in the search for viable therapeutics for treatment of the viral infections discussed above, therapeutic agents for many viruses remain severely limited. Furthermore, there are no known safe and therapeutic treatments for HBV, influenza and HIV. In HBV, with the possible exception of the drug 3TC, the use of nucleoside-based antiviral agents leads to toxicity, probably due to cross-inhibition of cellular mitchondrial DNA. Clearly, there is a need for a new class of antiviral agents which could minimize the toxicity associated with cross-inhibition. In influenza, amantadine and rimantadine have been shown to be moderately effective against only influenza A viruses, with amantadine having excessive side effects. Recently, strains of influenza A resistant to amantadine and rimantadine have been isolated. Accordingly, there is a need for new types of therapeutic antiviral agents particularly against both influenza A and influenza B, as well as against HIV, HBV and HIV and other viruses. Furthermore, due to the loss of CD4T lymphocytes in an HIV infected person, leading to immunodeficiency and thus increasing susceptibility to a broad range of opportunistic viral, bacterial, fungal, and protozoal pathogens, identifying anti-HIV agents having a spectrum of antiviral and antimicrobial activities is of particular interest. These agents would be not only effective against HIV infection, but also effective against or preventive of opportunistic infections in AIDS patients.

A natural source of calanolide A is limited.[4] This limited availability fueled the desire to develop practical synthesis routes to enable further study and development to be carried out on this active and promising series of compounds.

Herein, we describe synthetic calanolide analogues demonstrating potent antiviral activity against many viruses. We also describe methods of using such calanolide analogues for treating or preventing viral infections.

SUMMARY OF THE INVENTION

The present invention relates to calanolide analogues and methods of using such compounds for treating or preventing viral infections, especially infections caused by Hepatitis B, herpes viruses, or respiratory viruses. Herpes viruses against which calanolide analogues of the invention act as antiviral agents include Herpes Simplex Type 1, Herpes Simplex Type 2, Cytomegalovirus, Varicella Zoster Virus, or Epstein Barr Virus. Respiratory viruses against which calanolide analogues of the invention act as antiviral agents include Influenza A, Influenza B, Parainfluenza, Adenovirus, Measles, or Respiratory Syncytial Virus.

Calanolide analogues of the invention can be used alone or in combination with other therapeutic agents, including but not limited to Intron A and 3TC for Hepatitis B; gancyclovir, progancyclovir, famcyclovir, foscamet, vidarabine, cidovir, and acyclovir for herpes viruses; and ribavarin, amantidine, and rimantidine for respiratory viruses.

Calanolide analogues of the invention also demonstrate activity against multi-viral infections. For example, they are effective against both HIV and other opportunistic infections to which people with HIV are especially prone. Among all known HIV antiviral agents, the calanolide analogues described herein are unique in their ability to combat not only HIV but also other opportunistic infections.

The present invention provides calanolide analogues obtained via syntheses employing chromene 4 and chromanone 7 as key intermediates, which is described in U.S. patent application Ser. No. 08/510,213, filed Aug. 2, 1995, herein incorporated by reference in its entirety. Chromene 4 is synthesized by the sequence depicted in Scheme I. Thus, 5,7-dihydroxy-4-propylcoumarin, 2,[5] was prepared quantitatively from ethyl butyrylacetate and phloroglucinol under Pechmann conditions.[6] Product yield and purity were dependent on the amount of sulfuric acid used. The 8-position of 5,7-dihydroxy-4-propylcoumarin, 2, was then selectively acylated at 8–10° C. by propionyl chloride and AlCl$_3$ in a mixture of carbon disulfide and nitrobenzene to afford 5,7-dihydroxy-8-propionyl-4-propylcoumarin, 3.

In an alternative and preferred reaction, coumarin intermediate 3 may be produced in large scale quantities and with minimal formation of undesirable 6-position acylated product and 6,8-bis-acylated product by selective acylation of 5,7-dihydroxy-4-propylcoumarin 2 with a mixture of propionic anhydride and AlCl$_3$ at about 70–75° C.

The chromene ring was introduced upon treatment of compound 3 with 4,4-dimethoxy-2-methylbutan-2-ol, providing 4 in 78% yield (Scheme I). Chlorotitanium-mediated aldol reaction of chromene 4 with acetaldehyde led to formation of (±)-8a and (±)-8b in a ratio of 95:5. The racemic syn aldol product [(±)-8a] was resolved by enzyme-catalyzed acylation. Thus, in the presence of lipase and vinyl acetate, (−)-8a was selectively acylated and the desired enantiomer (+)-8a was unreacted. The purified (+)-8a was subjected to a Mitsunobu[7a–c] reaction, exclusively leading to (+)-trans-chromanone [(+)-7].

Finally, Luche reduction[8] on (+)-7 led to formation of (±)-calanolide A [(+)-1] which contained 10% of (+)-calanolide B (see Scheme III). (+)-Calanolide A [(+)-1] was further separated from (+)-calanolide B by preparative normal phase HPLC and was identical with an authentic sample.

If desired, the racemic anti aldol product [(±)-8b] may also be resolved by enzyme-catalyzed acylation into (+)-8b and the ester 10 from (−)-8b (Scheme IV). Mitsunobu reaction on (+)-8b would lead to formation of the cis-chromanone 7a which could then be reduced to produce calanolide C.

The synthetic sequence for (+)-calanolide A was extended to the synthesis of calanolide analogues. Thus, Pechmann reaction of phloroglucinol with various β-ketoesters yields substituted 5,7-dihydroxycoumarin 11 (Scheme V). Friedel-Crafts acylation of substituted 5,7-dihydroxycoumarin 11 leads to formation of 8-acylated 5,7-dihydroxycoumarin 12. Chromenylation of 12 can be achieved by reacting with substituted β-hydroxyaldehyde dimethylacetal, affording chromenocoumarin 13. Aldol reaction of chromenocoumarin 13 with carbonyl compounds in the presence of LDA with or without metal complexing agents forms the racemic aldol product (±)-14. Cyclization of (±)-14 under Mitsunobu conditions, by using triphenylphosphine and diethyl azodicarboxylate (DEAD), leads to formation of chromanone analogue (±)-15. Reduction of (±)-15 with sodium borohydride with or without cerium chloride yields the 12-hydroxy analogue (±)-16 (Scheme V).

Catalytic hydrogenation of both (±)-15 and (±)-16 produces 7,8-dihydro derivatives (±)-17 and (±)-18 (Scheme VI). Treatment of (±)-15 with hydroxylamine or alkoxyamine affords oxime derivatives (±)-19 (Scheme VI). Reduction of (±)-19 under different conditions[9] should selectively yield hydroxylamino or amino compounds (20 and 21).

Optically active forms of 14–21 would be obtained by employing enzymatic acylation, as described in Scheme III for (+)-calanolide A [(+)-1]. Thus, enzyme-catalyzed acylation of the racemic aldol product (±)-14 would selectively acylate one enantiomer [i.e. (−)-14] and leave the other enantiomer [i.e. (+)-14] unreacted, which would be easily separated by conventional methods such as silica gel column chromatography. The acylated enantiomer [i.e. (−)-14] may be hydrolyzed to form the pure enantiomer [i.e. (−)-14]. The optically pure enantiomers thus obtained [(+)-14 and (−)-14] will be cyclized to (+)-15 and (−)-15, respectively, by Mitsunobu reaction. Reduction of (+)-15 and (−)-15 would lead to formation of (+)-16 and (−)-16. Hydrogenation of optically active forms of 15 and 16 would provide pure enantiomers of 17 and 18 [(+)- and (+)-17; (+)- and (−)-18].

Treatment of pure enantiomers of 15 with hydroxylamine and alkoxylamine affords enantiomerically pure oxime 19 [(+)- and (−)-19]. If desired, (+)-19 and (−)-19 may be reduced to produce enantiomerically pure 20 and 21 [(+)- and (−)-20; (+)- and (−)-21].

The 12-hydroxyl group in compound 1, 16, and 17 as well as their optically active forms can be epimerized by a number of methods including acidic conditions, neutral Mitsunobu conditions[7a–c], or with DAST.[7d] An example showing conversion of (−)-calanolide A [(−)-1] into (−)-calanolide B is depicted in Scheme VII.

The process used to produce compounds of the present invention may be utilized to prepare a wide variety of calanolide analogues such as Formulas i–v shown in Scheme VIII and Formulas vi–vii shown in Scheme IX.

For Formula i, R$_1$ and R$_2$ are independently ⋯⋯IIII or ◂▬.

For Formula ii, R$_1$, R$_2$, and R$_3$ are independently H or CH$_3$.

For Formula iii, R$_1$ is C$_1$–C$_6$ linear or branched alkyl.

For Formula iv, R$_1$ is propyl or phenyl and R$_2$ is ⋯⋯IIIOH or ◂▬OH.

For Formula vi, R$_1$ is C$_1$–C$_6$ linear or branched alkyl.

For Formula vii, R$_1$ is propyl or phenyl and R$_2$ is ⋯⋯IIIOH or ◂▬OH.

Additional exemplary calanolide analogues include but are not limited to Formulas 15 and 16 shown in Scheme V, and Formulas 17 and 18 shown in Scheme VI.

Methods for treating and/or preventing viral infections using compounds of the invention are also described. Representative viral infections include HIV, hepatitis B, herpes simplex type 1 and 2, cytomegalovirus, varicella zoster virus, Epstein Barr virus, influenza A and B, parainfluenza, adenovirus, measles, and respiratory syncytial virus.

Accordingly, it is an object of the invention to provide calanolide analogues obtained via syntheses employing chromene 4 and chromanone 7 as key intermediates.

A further object of the invention is to provide a method for treating or preventing viral infections using calanolide analogues of the formula I:

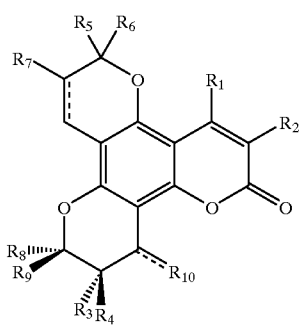

I wherein

R$_1$ is H, halogen, hydroxyl, amino, C$_{1-6}$ alkyl, aryl-C$_{1-6}$ alkyl, mono- or poly-fluorinated C$_{1-6}$ alkyl, hydroxy-C$_{1-6}$ alkyl, C$_{1-6}$ alkoxy, amino-C$_{1-8}$ alkyl, C$_{1-6}$ alkyl amino, di(C$_{1-6}$ alkyl)amino, C$_{1-8}$ alkylamino-C$_{1-8}$ alkyl, di(C$_{1-6}$ alkyl) amino-C$_{1-8}$ alkyl, cyclohexyl, aryl, or heterocycle, wherein aryl or heterocycle may each be unsubstituted or substituted with one or more of the following: C$_{1-6}$ alkyl, C$_{1-6}$ alkoxy, hydroxy-C$_{1-4}$ alkyl, hydroxyl, amino, C$_{1-6}$ alkylamino, di(C$_{1-6}$ alkyl) amino, amino-C$_{1-8}$ alkyl, C$_{1-8}$ alkylamino-C$_{1-8}$ alkyl, di(C$_{1-6}$ alkyl)amino-C$_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl) amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R^6$ can be taken together to form a 5–7 membered saturated cycle ring or heterocycle ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_8$ and $R_9$ can be taken together to form a 5–7 membered saturated cycle ring or heterocyclic ring;

$R_{10}$ is halogen, O, $OR_{11}$, $NOR_{11}$, $NHOR_{11}$, $NOR_{12}$, $NHOR_{12}$, $NR_{11}R_{12}$, $NR_{12}$, or $NR_{12}R_{13}$; wherein $R_{11}$ is H, acyl, $P(O)(OH)_2$, $S(O)(OH)_2$, $CO(C_{1-10}$ alkyl)$CO_2H$, $(C_{1-8}$ alkyl)$CO_2H$, $CO(C_{1-10}$ alkyl)$NR_{12}R_{13}$, $(C_{1-8}$ alkyl)$NR_{12}R_{13}$; $R_{12}$ and $R_{13}$ are independently selected from the group consisting of H, $C_{1-6}$ alkyl, aryl, and aryl-$C_{1-6}$ alkyl; and $R_{12}$ and $R_{13}$ can be taken together to form a 5–7 membered saturated heterocyclic ring containing said nitrogen;

or a pharmaceutically acceptable salt thereof.

These and other objects of the invention will become apparent in view of the detailed description below.

SCHEME II

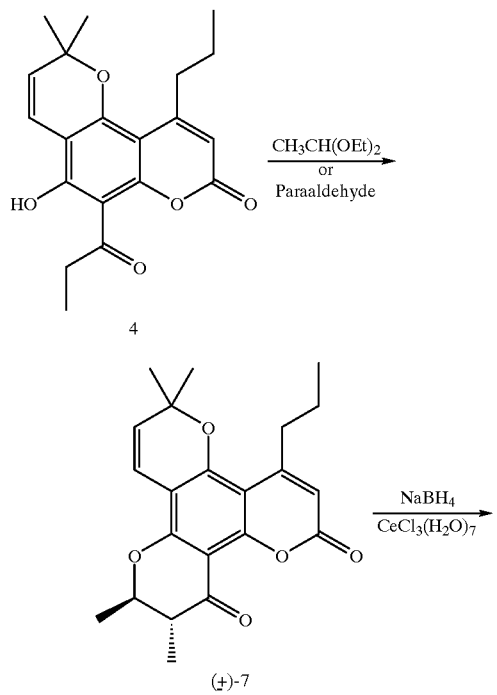

SCHEME I

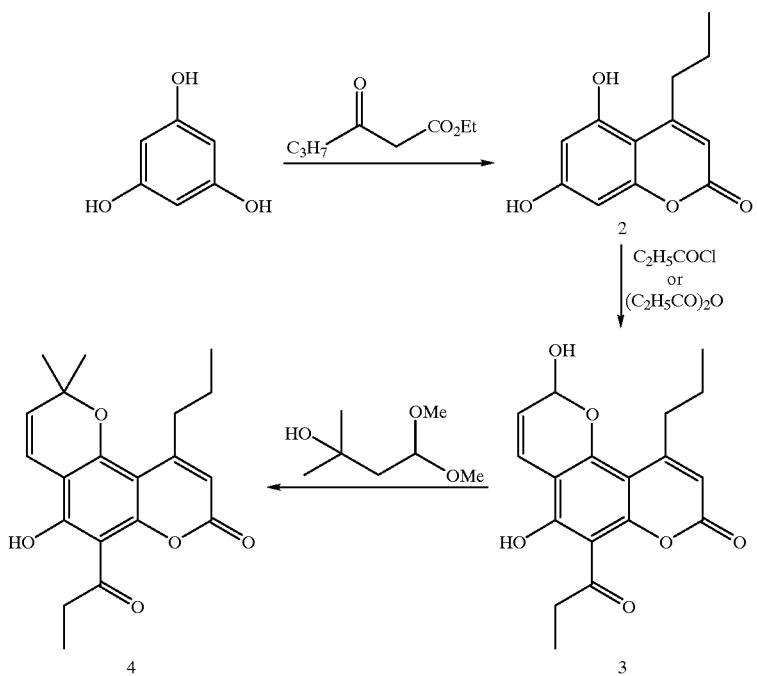

-continued
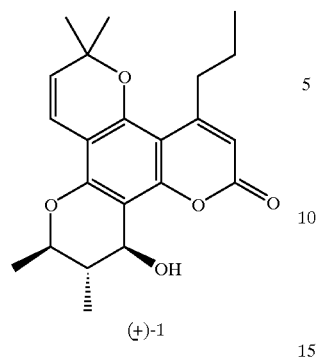
(±)-1
SCHEME III
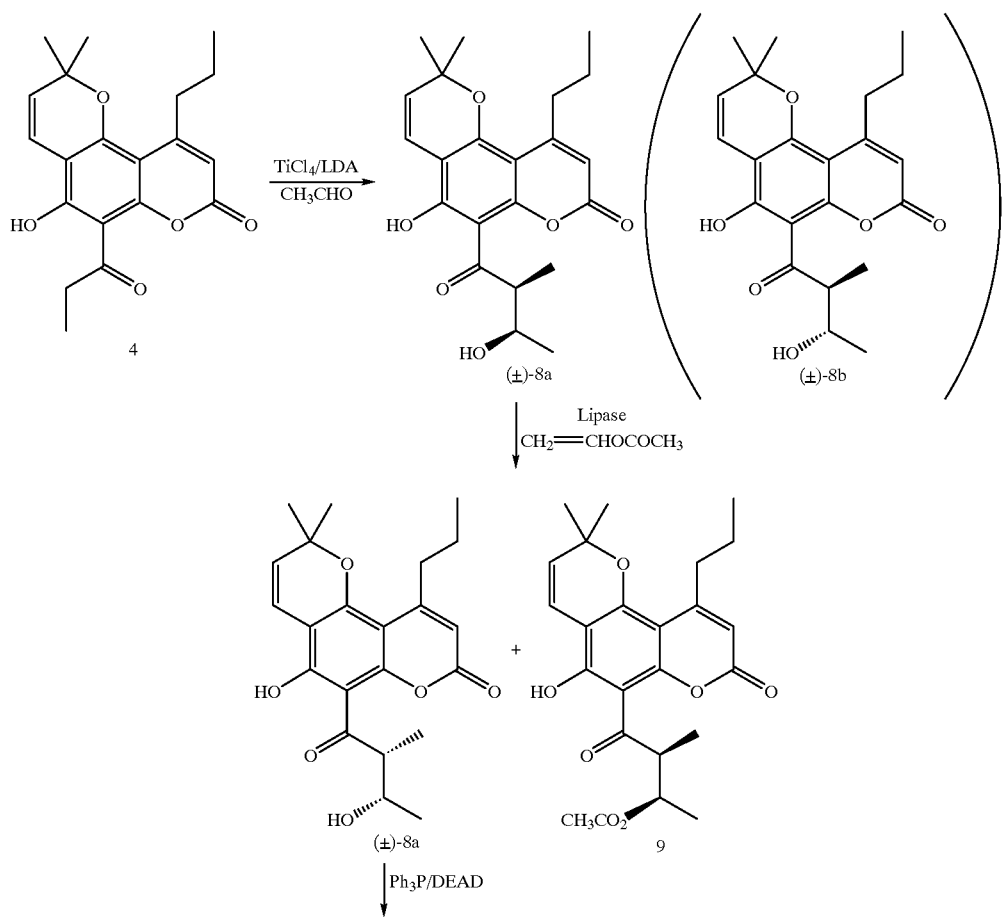

-continued
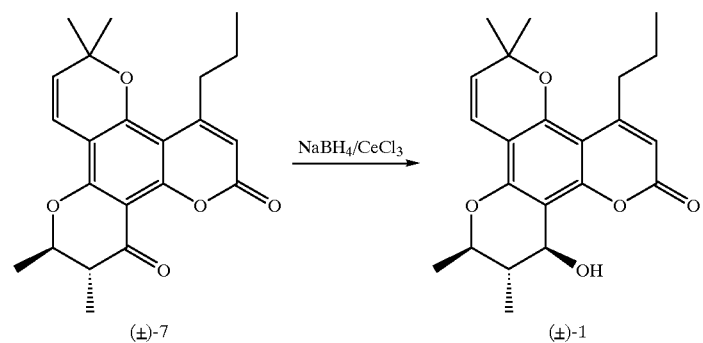
SCHEME IV
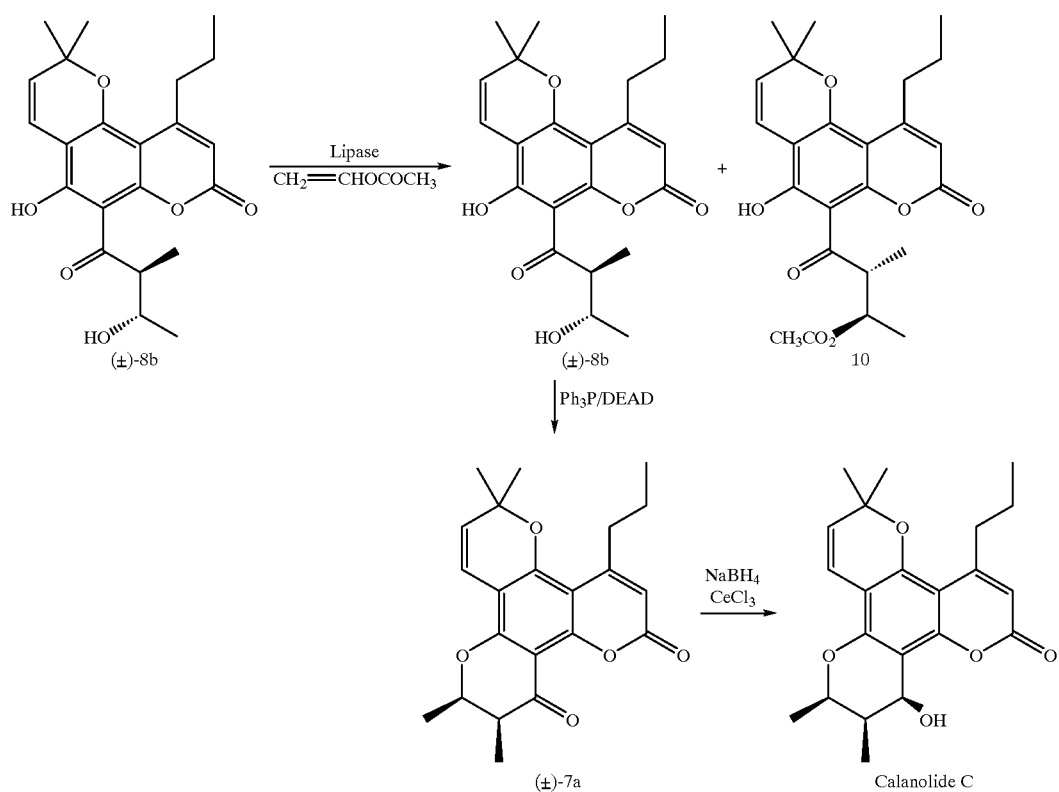

SCHEME V
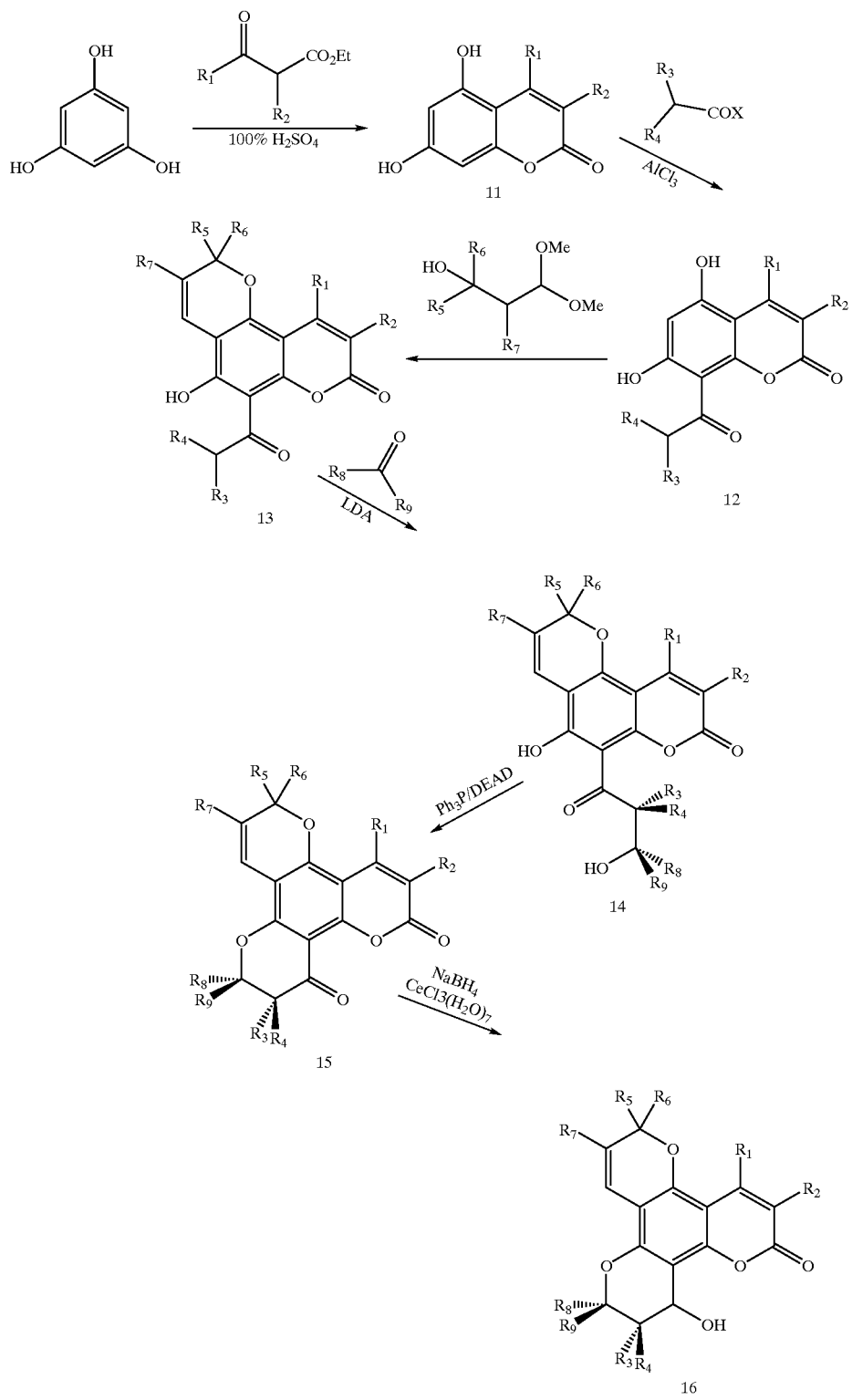

SCHEME VI
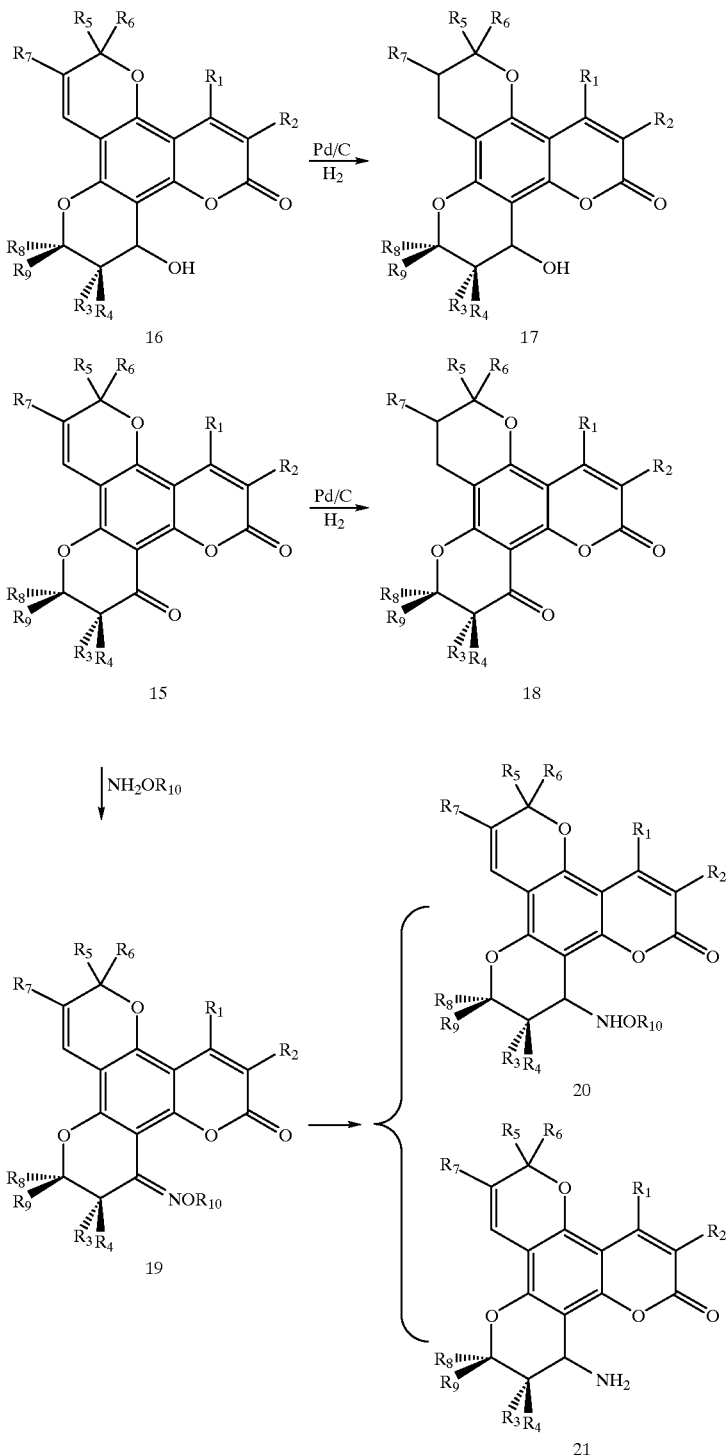

SCHEME VII

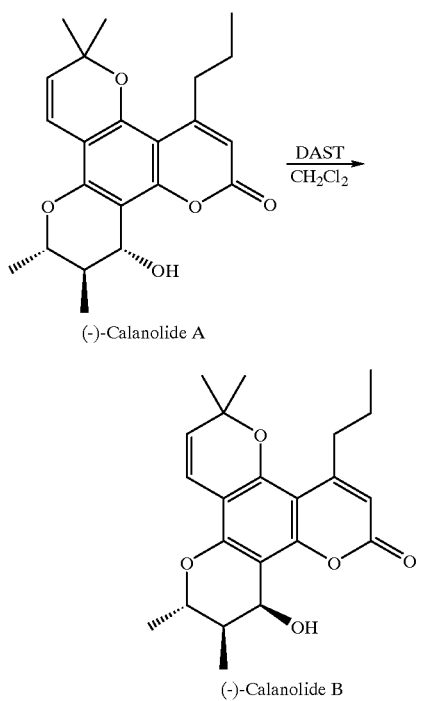

(−)-Calanolide A (−)-Calanolide B

22

SCHEME VIII

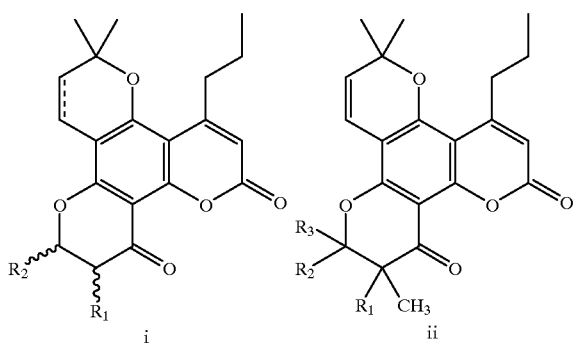

i ii

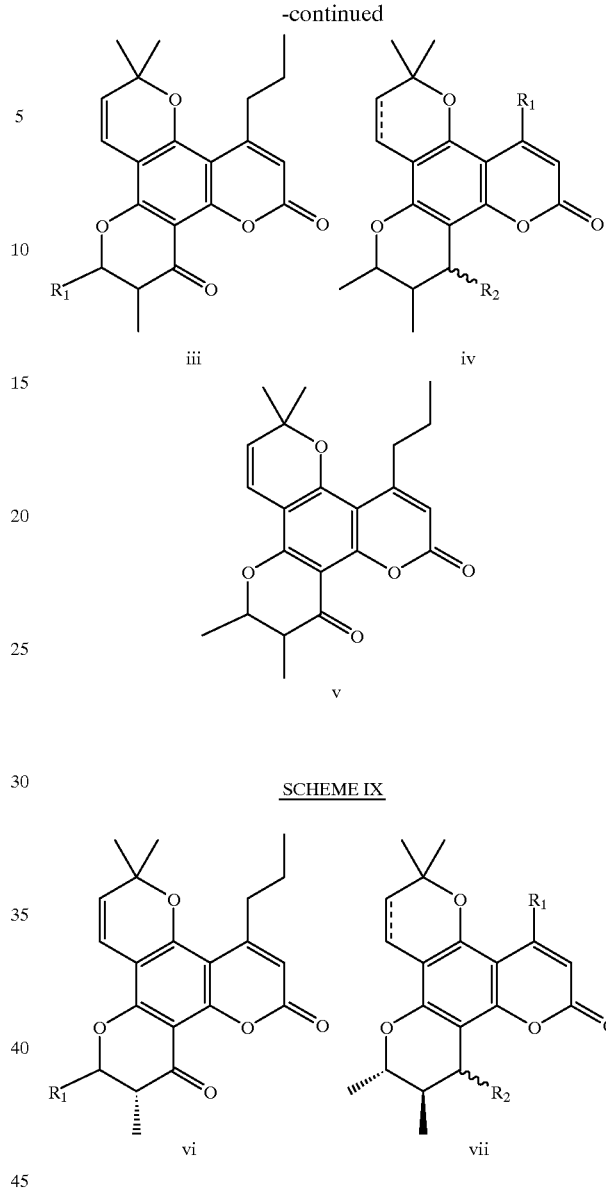

iii iv v

SCHEME IX

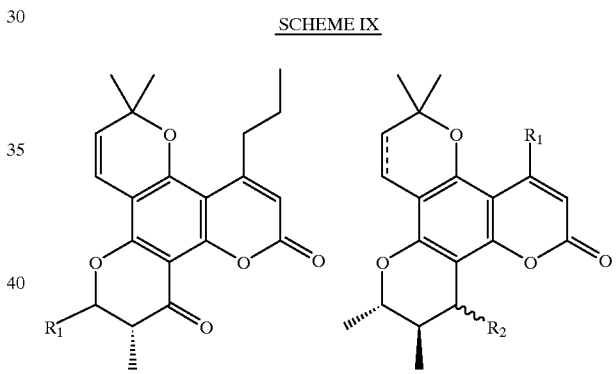

vi vii

DESCRIPTION OF THE DRAWINGS

FIG. 6 is an HPLC chromatogram of (a) (±)-calanolide A on normal phase column; (b) (±)-calanolide A on a chiral HPLC column; (c) (+)-calanolide A on a chiral HPLC column and (d) (−)-calanolide A on a chiral TPLC column. The HPLC conditions are described in Example 13.

DETAILED DESCRIPTION OF THE INVENTION

Figure 1A:
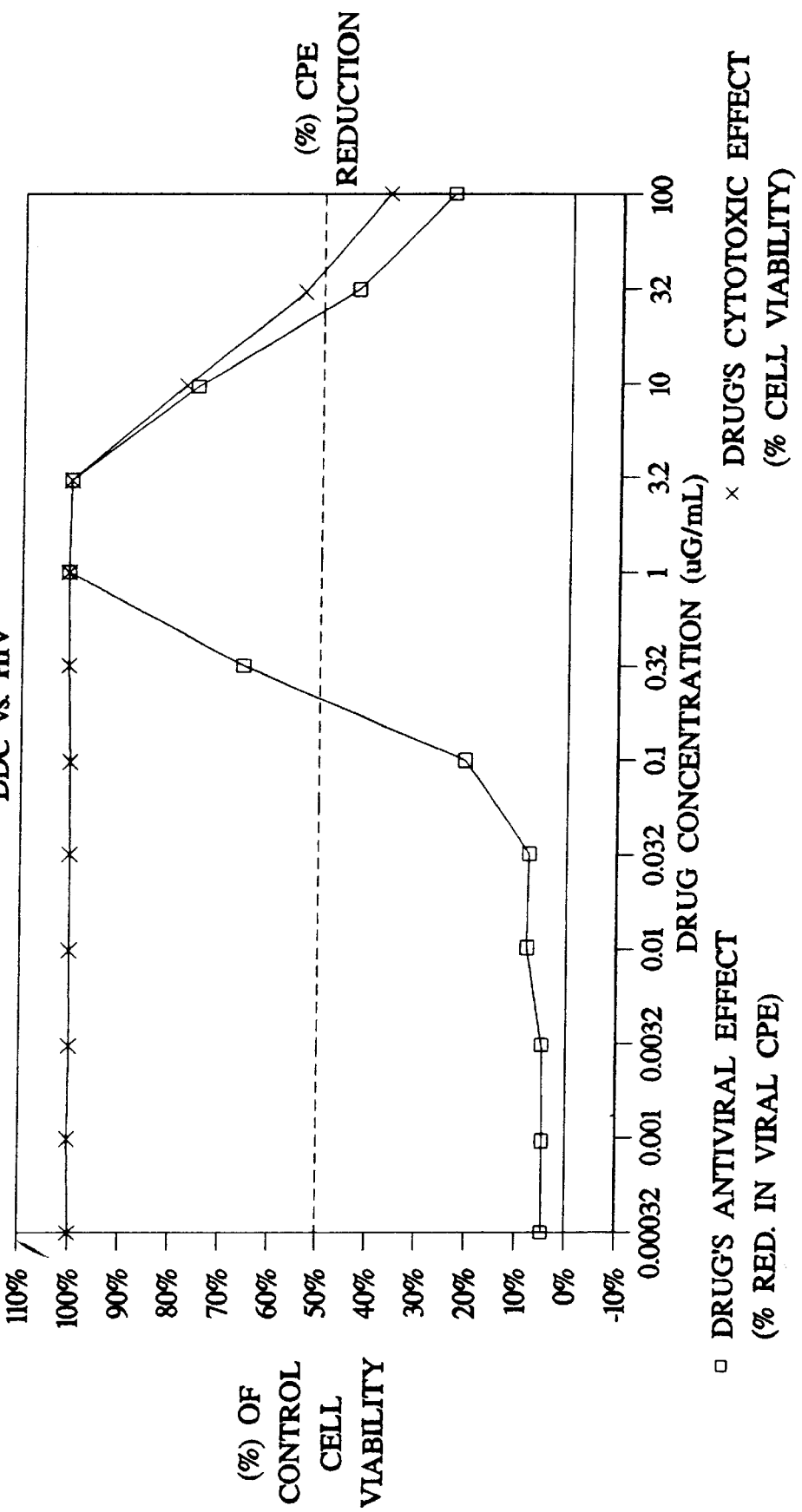
FIGS. 1(a) to 1(e) illustrate in vitro MTT assay results, as described in Example 37, using G910-6 HIV viral strain which is AZT-resistant.

All patents, patent applications, and literature references cited herein are incorporated by reference in their entirety.

The present invention relates to calanolide analogues and methods of using such compounds for treating or preventing viral infections. In one embodiment, the invention provides calanolide analogues obtained via syntheses employing chromene 4 and chromanone 7 as key intermediates, as shown in Schemes I and III. According to this synthetic scheme, chromene 4 may be prepared from 5,7-dihydroxy-4-propylcoumarin, 2, as shown in Scheme I. According to this synthetic scheme, 5,7-dihydroxy-4-propylcoumarin, 2,5 was prepared quantitatively from ethyl butyrylacetate and phloroglucinol under Pechmann conditions.[6]

In conducting this reaction, a volume of a concentrated acid is added in a dropwise manner to a stirring mixture of ethyl butyrylacetate and phloroglucinol with a molar ratio ranging between about 3:1 and about 1:3, with a preferable range being about 0.9:1.0. The dropwise addition of an acid was conducted at a rate such that the temperature of the reaction mixture is maintained at a temperature ranging between about 0° C. and about 120° C., preferably about 90° C.

Suitable, but not limiting, examples of concentrated acid include sulfuric acid, trifluoroacetic acid, and methanesulfonic acid. In making compounds of the invention, concentrated sulfuric acid is particularly preferred. As the product yield and purity appear to be dependent on the amount of concentrated sulfuric acid used, it is preferred that the amount of concentrated sulfuric acid ranges between about 0.5 and 10 mole, most preferably ranging between about 2 and about 3.5 mole, per mole of ethyl butyrylacetate.

The reaction mixture is then heated to a temperature ranging between about 40° C. and about 150° C., preferably about 90° C., until the reaction reaches completion as determined by TLC analysis. The reaction mixture is then poured onto ice and the precipitated product is collected by filtration and dissolved in an organic solvent. Suitable, but non-limiting, examples of organic solvents include ethyl acetate, chloroform, and tetrahydrofuran. A preferred solvent is ethyl acetate. The resulting solution is then washed with brine and dried over a suitable drying agent, e.g., sodium sulfate. The yields of this reaction are generally quantitative.

Thereafter, 5,7-dihydroxy-8-propionyl-4-propylcoumarin, 3, was prepared by selectively acylating the 8-position of 5,7-dihydroxy-4-propylcoumarin, 2, with propionyl chloride in the presence of a Lewis acid catalyst (Friedel-Crafts acylation). In conducting this reaction, a solution of propionyl chloride in a suitable solvent, e.g., carbon disulfide, was added in a dropwise manner to a vigorously stirred solution of 5,7-dihydroxy-4-propylcoumarin, 2, a Lewis acid and an organic solvent cooled in an ice bath. Dropwise addition of propionyl chloride is conducted such that the temperature of the reaction mixture is maintained at a temperature ranging between 0° C. and about 30° C., preferably between about 8° C. and 10° C.

In making compounds of the invention, the amount of propionyl chloride used generally ranges between about 0.5 and about 6 moles, preferably ranging between about 1 and about 2 moles, per mole of 5,7-dihydroxy-4-propylcoumarin, 2.

Non-limiting examples of Lewis acid catalysts useful in the acylation reaction include $AlCl_3$, $BF_3$, $SnCl_4$, $ZnCl_2$, $POCl_3$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 5 moles, per mole of 5,7-dihydroxy-4-propylcoumarin, 2.

Non-limiting examples of organic solvent for use in preparing the 5,7-dihydroxy-4-propylcoumarin, 2, solution include nitrobenzene, nitromethane, chlorobenzene, or toluene and mixtures thereof. A preferred organic solvent for use in this invention is nitrobenzene.

Upon completion of the addition of propionyl chloride, the vigorously stirred reaction mixture is maintained at a temperature ranging between about 0° C. and about 120° C., preferably ranging between about 25° C. and 80° C., until the reaction reaches completion as monitored by conventional means such as TLC analysis. The reaction mixture is then poured onto ice and extracted several times with a suitable solvent such as ethyl acetate, chloroform, methylene chloride, tetrahydrofuran, or a mixture of chloroform/methanol. A preferred solvent for this extraction is ethyl acetate. The extracts are then dried over a suitable drying agent, e.g., sodium sulfate, and the product may be purified by conventional means such as silica gel column chromatography.

On small scale (<1 gram), the yield of 5,7-dihydroxy-8-propionyl-4-propylcoumarin 3, produced by the above described reaction is generally quantitative. However, on larger scale (>1 gram), the reaction was very difficult to control and did not exclusively afford the desired product as the desired 8-position acylated product 3 was accompanied by the formation of undesired 6-position acylated product and 6,8-bis-acylated product. Thus, an alternative and preferred route for preparing 5,7-dihydroxy-8-propionyl-4-propylcoumarin 3 in large scale quantities was devised.

Preparation of 8-acylated coumarin 3 on a 5 gram scale as a single product (45% yield) has been achieved by adding a mixture of propionic anhydride, a Lewis acid, e.g., $AlCl_3$, and suitable solvent, e.g., 1,2-dichloroethane, into a vigorously stirring pre-heated mixture of coumarin, a Lewis acid, e.g., $AlCl_3$, and suitable solvent, e.g., 1,2-dichloroethane, at a temperature ranging between about 40° C. and about 160° C., preferably ranging between about 70° C. and about 75° C. Dropwise addition of the propionic anhydride solution is conducted at a rate such that the temperature of the reaction mixture is maintained within the desired temperature range.

The amount of propionic anhydride used in the reaction generally ranges between about 0.5 and about 10 moles, preferably ranging between about 1 and about 2 moles, per mole of 5,7-dihydroxy-4-propylcoumarin 2.

Non-limiting examples of Lewis acid catalysts useful in the acylation reaction include $AlCl_3$, $BF_3$, $POCl_3$, $SnCl_4$, ZnCl$_2$ and TiCl$_4$. A preferred Lewis acid catalyst is AlCl$_3$. The amount of Lewis acid catalyst relative to 5,7-dihydroxy-4-propylcoumarin, 2, ranges between about 0.5 and about 12 moles, preferably ranging between about 2 and about 4 moles, per mole of 5,7-dihydroxy-4-propylcoumarin, 2.

Suitable but nonlimiting examples of solvents for use in making compounds of the invention include diglyme, nitromethane, 1,1,2,2-tetrachloroethane, and 1,2-dichloroethane (preferred). Upon completion of the addition of propionyl anhydride, the vigorously stirred reaction mixture is maintained at a temperature ranging between about 40° C. and about 160° C., preferably ranging between about 70° C. and 75° C., until the reaction reaches completion as monitored by conventional means such as TLC analysis. The workup procedure is the same as described above.

The product was purified without the use of column chromatography to afford the desired product 3. This procedure has been scaled-up to 1.7 kg of coumarin (for details see experimental section) and the yield for 8-acylated coumarin 3 was 29% after recrystallization. The yield for 8-acylated coumarin 3 may be further improved by changing the purification processing. For example, the crude product may be recrystallized from solvent(s) other than dioxane, or a simple washing with an appropriate solvent may lead to product pure enough for the next reaction step.

Thereafter, chromene 4 was prepared by introducing the chromene ring into 5,7-dihydroxy-8-propionyl-4-propylcoumarin, 3, using 4,4-dimethoxy-2-methylbutan-2-ol. A solution of 5,7-dihydroxy-8-propionyl-4-propylcoumarin, 3, and 4,4-dimethoxy-2-methylbutan-2-ol in a suitable organic solvent in the presence of a base was reacted at a temperature ranging between about 40° C. and about 180° C., preferably ranging between about 100° C. and about 120° C., until the reaction reached completion as determined by conventional means such as TLC analysis. Water and methanol formed during the reaction were removed azeotropically via a Dean-Stark trap.

In making compounds of the invention, the amount of 4,4-dimethoxy-2-methylbutan-2-ol employed in the reaction generally ranges between about 0.5 and about 8 moles, preferably ranging between about 2 and about 4 moles, per mole of 5,7-dihydroxy-8-propionyl-4-propylcoumarin 3.

Suitable, but not limiting examples of organic solvents include pyridine, triethylamine, N,N-dimethylformamide (DMF), toluene, tetrahydrofuran (THF) or 1,2-dichloroethane. Suitable, but non-limiting examples of the bases include pyridine, 4-dimethylaminopyridine, triethylamine, N,N-diethylaniline, 1,5-diazabicyclo-[4,3,0]-non-5-ene (DBN), 1,8-diazabicyclo-[5,4,0]undec-7-ene (DBU), sodium carbonate and sodium bicarbonate. Pyridine was used as both base and solvent in this invention on a small scale; for scale-up, however, pyridine was used as a base and toluene was used as a solvent.

Upon completion of the reaction, the solvent is removed under reduced pressure and the reaction product is dissolved in a suitable solvent, e.g., ethyl acetate. The solution is then washed sequentially with water and brine and dried over a suitable drying agent, e.g., sodium sulfate. Thereafter, the crude chromene 4 product can be purified by conventional means such as silica gel column chromatography using 25% ethyl acetate/hexane as the elution solvent. The yields of chromene 4 generally fall with the range of about 60% and about 85%, usually resulting in about 78% yield. Chromene 4 was then used to prepare chromanone 7.

A number of alternative routes were devised for preparing chromanone 7 from chromene 4 in large scale quantities. These routes were described in U.S. patent application Ser. No. 08/510,213, filed Aug. 2, 1995, the disclosure which is incorporated herein in its entirety. For instance, U.S. patent application Ser. No. 08/510,213 describes a one-step reaction process (paraldehyde one-step reaction), shown in Scheme II, and a two-step reaction process (LDA/sulfuric acid process or LDA/Mitsunobu process) for preparing chromanone 7 from chromene 4. Examples of these reactions are provided in the Examples below. In this invention, a new route for preparing chromanone 7 from chromene 4 was devised, shown in Scheme III, which introduces a chiral resolution step between the two step LDA/Mitsunobu process described in the 08/510,213 application and illustrated below. One of the benefits for including the enzyme acylation/resolution step at this stage of the process is that it provides a more practical and economical means for producing large scale amounts of chromanone (+)-7, which would lead to formation of (+)-calanolide A after reduction without the subsequent need for chiral HPLC resolution of the racemic calanolide A.

According to Scheme III, (+)-chromanone 7 was prepared by a chlorotitanium-mediated aldol condensation reaction of chromene 4 with acetaldehyde which led to formation of aldol products (±)-8a and (±)-8b in a ratio of 95:5, respectively. In conducting the aldol condensation reaction, a solution of LDA was added dropwise to a solution of chromene 4 dissolved in a solvent at a temperature ranging between about −78° C. and about 0° C., preferably about −30° C. and about −78° C. Thereafter, a solution of titanium tetrachloride was added dropwise to the stirring reaction mixture. The resulting solution was then warmed to a temperature ranging between about −78° C. and about 40° C., preferably about −40° C., and allowed to stir for about 45 minutes to allow for transmetallation. Thereafter, the solution was recooled to −78° C.

The amount of LDA added per mole of chromene 4 ranged between about 1 and about 4 moles, preferably ranging between about 2 and about 3 per mole of chromene 4. Dropwise addition LDA is conducted such that the reaction temperature is maintained within the desired range.

The amount of titanium tetrachloride ranges between about 0.5 and about 10 moles, preferably ranging between about 2 and about 4 moles per mole of chromene 4.

Suitable, but not limiting examples of solvent include methylene chloride, THF, diethyl ether, dioxane, etc.

Acetaldehyde was then added dropwise to the reaction mixture in amounts ranging between about 1 and about 12 moles, preferably ranging between about 4 and about 6 moles per mole of chromene 4. Dropwise addition of acetaldehyde is conducted such that the reaction temperature is maintained within the aforementioned range. The reaction was monitored by conventional means, e.g., TLC analysis, until it reached completion.

The aldol reaction of chromene 4 with acetaldehyde may be carried out under conditions which employs bases other than LDA. For example, metal hydroxides such as NaOH, KOH and Ca(OH)$_2$, metal alkoxides such as MeONa, EtONa and t-BuOK, and amines such as pyrrolidine, piperidine, diisopropylethylamine, 1,5-diazabicyclo[4,3,0]non-5-ene (DBN), 1,8-diazabicyclo[5,4,0]undec-7-ene (DBU), NaNH$_2$ and LiHMDS as well as hydrides such as NaH and KH can all be employed for the aldol reactions.[10] Also, aldol reactions can be mediated by metal complexes of Al, B, Mg, Sn, Zn, Zr and other Ti compounds such as (i-PrO)$_3$TiCl, (i-PrO)$_4$Ti, PhBCl$_2$, (n-Bu)$_2$BCl, BF$_3$, (n-Bu)$_3$SnCl, SnCl$_4$, ZnCl$_2$, MgBr$_2$, Et$_2$AlCl with or without chiral auxiliaries such as 1,1'-binaphthol, norephedrinesulfonate, camphanediol, diacetone glucose and dialkyl tartrate.[11–13]

Thereafter, the reaction mixture was quenched at −30° C. to −10° C. with saturated aqueous ammonium chloride solution and extracted with a suitable solvent, e.g., ethyl acetate. The pooled extracts were washed with brine and dried over a suitable drying agent, e.g., sodium sulfate. The yields of aldol product generally range between about 40% and about 80%, usually about 70%.

It should be noted that the aldol reaction of chromene 4 results in a product having two asymmetric centers which in turn would result in a diastereomeric mixture of two sets of enantiomers (four optically active forms). The mixture may be separated by conventional means to produce racemic syn aldol product (±)-8a and racemic anti aldol product (±)-8b which may be resolved into optically active forms. Conventional resolution methods may be used such as chromatography or fractional crystallization of suitable diastereoisomeric derivatives such as salts or esters with optically active acids (e.g., camphor-10-sulfonic acid, camphoric acid, methoxyacetic acid, or dibenzoyltartaric acid) or enzymatically catalyzed acylation or hydrolysis of the racemic esters. The resultant or synthetic enantiomer may then be transformed to enantioselective synthesis of (+)-calanolide A and its congeners.

In one method, the racemic aldol product may be resolved by high performance liquid chromatography (HPLC) with organic solvent system as a mobile phase. HPLC is performed on a column packed with chiral packing material. Suitable, but not limiting, examples of chiral packing material include amylose carbamate, D-phenylglycine, L-phenylglycine, D-leucine, L-leucine, D-naphthylalanine, L-naphthylalanine, or L-naphthylleucine. These materials may be bounded, either ionically or covalently, to silica sphere which particle sizes ranging between about 5 m and about 20 m. Suitable, but non-limiting, mobile phase includes hexane, heptane, cyclohexane, ethyl acetate, methanol, ethanol, or isopropanol and mixtures thereof. The mobile phase may be employed in isocratic, step gradient or continuous gradient systems at flow rates generally ranging between about 0.5 mL/min. and about 50 mL/min.

In making compounds of the invention, the racemic product, i.e., syn aldol product [(±)-8a], is resolved preferably by enzyme-catalyzed acylation. Enzymatic resolution may employ enzymes such as lipase CC (*Candida cylindracea*), lipase AK (*Candida cylindracea*), lipase AY (*Candida cylindracea*), lipase PS (*Pseudomonas Species*), lipase AP (*Aspergillus niger*), lipase N (*Rhizopus nieveuis*), lipase FAP (*Rhizopus nieveus*), lipase PP (Porcine Pancrease), pig (porcine) liver esterase (PLE), pig liver acetone powder (PLAP), or subtilisin. Immobilized forms of the enzyme on cellite, molecular sieves, or ion exchange resin are also contemplated for use in this method. The amount of enzyme used in the reaction depends on the rate of chemical conversion desired and the activity of the enzyme. The preferred enzyme for use in the enzyme-catalyzed acylation reaction is lipase.

The enzymatic acylation reaction is carried out in the presence of an acylating agent. Suitable, but not limiting, examples of acylating agents include vinyl acetate, vinyl propionate, vinyl butyrate, vinyl stearate, acetic anhydride, propionic anhydride, phthalic anhydride, acetic acid, propionic acid, hexanoic acid or octanoic acid. The enzymatic reaction employs at least one mole of acylating agent per mole of aldol product. Acylating agent can be used as a solvent in the acylation reaction or in solution with another solvent such as hexanes, chloroform, benzene, tert-butylmethyl ether, and TBF. The preferred solvent and acylating agent for use in the enzyme-catalyzed acylation are tert-butylmethyl ether and vinyl acetate, respectively.

Suitable, but not limiting examples of solvents for use in the enzymatic hydrolysis reaction include water, suitable aqueous buffers such as sodium phosphate buffers, or alcohols such as methanol or ethanol.

One skilled in the art will appreciate that racemic esters of aldol products can be made by conventional esterification means and selectively hydrolyzed by enzymes so as to produce, in high enantiomeric excess, optically active aldol product, i.e., (+)-8, in free or esterified form.

The purified (+)-8a was subjected to a neutral Mitsunobu reaction, selectively leading to (+)-trans-chromanone [(+)-7]. In performing this reaction, diethyl azodicarboxylate (DEAD) was added dropwise to a solution containing (+)-8a and triphenylphosphine at a temperature ranging between about −10° C. and about 40° C., preferably about ambient temperature. The amount of DEAD used in the reaction generally ranges between about 1 mole and about 10 moles preferably about 1 mole and about 4 moles, per mole of aldol (+)-8a. The amount of triphenylphosphine used in the reaction generally ranged between about 1 mole and about 10 moles, preferably ranging between about 1 mole and about 4 moles, per mole of aldol (+)-8a.

Instead of DEAD, other suitable azo reagents reported in the literature can be employed such as diisopropyl azodicarboxylate (DIAD), dibutyl azodicarboxylate (DBAD), dipiperidinoazodicarboxamide, bis(N$^4$-methylpiperazin-1-yl)azodicarboxamide, dimorpholinoazodicarboxamide, N,N,N',N'-tetramethylazodicarboxamide (TMAD)[14]. Also, in addition to triphenylphosphine, other phosphine derivatives such as tri-n-butylphosphine,[14] triethylphosphine, trimethylphosphine and tris(dimethylamino)phosphine may be used.

Thereafter, the reaction was quenched with saturated ammonium chloride upon completion and extracted with a suitable solvent, e.g., ethyl acetate. The pooled organic layers were washed with brine, concentrated in vacuo and the crude chromanone (+)-7 was purified by conventional means as discussed above. The yields of chromanone (+)-7 from the Mitsunobu reaction generally range between about 60% and about 80%, usually about 70%.

Finally, mild borohydride reduction of chromanone (+)-7 in the presence of CeCl$_3$(H$_2$O)$_7$ (Luche reduction) produced (+)-calanolide A with the desired stereochemical arrangement. In conducting the reduction reaction, a solution of chromanone (+)-7 was added dropwise into a solution of reducing agent, e.g., sodium borohydride and a metal additive, e.g., CeCl$_3$(H$_2$O)$_7$ in ethanol. The rate of addition is such that the reaction mixture temperature is maintained within a range of between about −40° C. and about 60° C., preferably ranging between about −10° C. and about −30° C. Thereafter, the reaction mixture was stirred at a temperature ranging between about −40° C. and about 60° C.

In general, the amount of metal additive, e.g., CeCl$_3$(H$_2$O)$_7$ present in the reaction mixture ranged between about 0.1 and about 2 moles, preferably ranging between bout 0.5 and about 1 mole, per mole of sodium borohydride. In addition, the amount of reducing agent, e.g., sodium borohydride employed in the reaction generally ranged between about 0.1 and about 12 moles, preferably ranging between about 2 and about 4 moles, per mole of chromanone (+)-7. Suitable, but non-limiting, examples of reducing agents include NaBH$_4$ LiAlH$_4$,(i-Bu)$_2$AlH,(n-Bu)$_3$SnH,9-BBN, Zn(BH$_4$)$_2$, BH$_3$, DIP-chloride, selectrides and enzymes such as baker yeast. Suitable, but non-limiting, examples of metal additives include CeCl$_3$, ZnCl$_2$, AlCl$_3$, TiCl$_4$, SnCl$_3$, and LnCl$_3$ and their mixture with triphenylphosphine oxide. In practicing this invention, sodium borohydride as reducing agent and CeCl$_3$H$_2$O)$_7$ as metal additive are preferred.

Thereafter, the reduction mixture was diluted with water and extracted with a suitable solvent, e.g., ethyl acetate. The extract was dried over a suitable drying agent, e.g., sodium sulfate, and concentrated. The resulting residue was then purified by conventional means such as silica gel chromatography, using ethyl acetate/hexane solvent mixtures. Luche reduction on (+)-7 led to formation of (+)-calanolide A [(+)-1] which contained 10% of (+)-calanolide B. (+)-Calanolide A [(+)-1] was further separated from (+)-calanolide B by preparative normal phase HPLC and was identical with an authentic sample.

Thus, (+)-calanolide A, 1, was successfully prepared with the desired stereochemical arrangement by treatment of the key intermediate chromene 4 with chlorotitanium catalyzed aldol reaction to produce (±)-8a, enzyme resolution of the racemate to produce (+)8a, and neutral Mitsunobu reaction of (+)-8a to produce chromanone (+)-7, followed by Luche reduction via chromanone (+)-7 (see Scheme III).

Enzyme resolution of trans-(±)8b racemate with vinyl acetate and lipase allowed for the separation of (+)-8b, which, following treatment under neutral Mitsunobu reaction with triphenylphosphine and DEAD and subsequent Luche reduction, would result in calanolide C (Scheme IV).

In another embodiment of the invention, analogues of calanolide A are provided by extension of the aforementioned synthetic sequence for (+)-calanolide A. Pechmann reaction of phloroglucinol with substituted β-ketoesters yields substituted 5,7-dihydroxycoumarin 11 as shown in Scheme V. The conditions and reagents used in the Pechmann reaction are described above.

Suitable, but non-limiting, β-ketoesters include those of formula a:

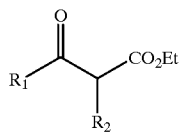

a wherein R$_1$ is H, halogen, hydroxyl, amino, C$_{1-6}$ alkyl, aryl-C$_{1-6}$ alkyl, mono- or poly-fluorinated C$_{1-6}$ alkyl, hydroxy-C$_{1-6}$ alkyl, C$_{1-6}$ alkoxy, amino-C$_{1-8}$ alky, C$_{1-6}$ alkylamino, di(C$_{1-6}$ alkyl)amino, C$_{1-8}$ alkylamino-C$_{1-8}$ alky, di(C$_{1-6}$ alkyl) amino-C$_{1-8}$ alkyl, cyclohexyl, aryl, or heterocycle, wherein aryl or heterocycle may each be unsubstituted or substituted with one or more of the following: C$_{1-6}$ alky, C$_{1-6}$ alkoxy, hydroxy-C$_{1-4}$ alkyl, hydroxyl, amino, C$_{1-6}$ alkylamino, di(C$_{1-6}$ alkyl)amino, amino-C$_{1-8}$ alkyl, C$_{1-8}$ alkylamino-C$_{1-8}$ alkyl, di(C$_{1-6}$ alkyl-amino-C$_{1-8}$ alkyl, nitro, azido or halogen; and R$_2$ is H, halogen, hydroxyl, C$_{1-6}$ alkyl, aryl-C$_{1-6}$ alkyl, mono- or poly-fluorinated C$_{1-6}$ alkyl, aryl or heterocycle.

Friedel-Crafts acylation of substituted 5,7-dihydroxycoumarin 11 leads to formation of 8-acylated 5,7-dihydroxycoumarin 12. The conditions and reagents used in the Friedel-Crafts acylation reaction are described above.

Non-limiting examples of carboxylic acid anhydrides and halides include formula b carboxylic acid anhydrides and halides:

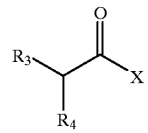

b wherein X is halogen (e.g. chloro) or OCOCHR$_3$R$_4$ wherein R$_3$ and R$_4$ are independently selected from the group consisting of H, halogen, hydroxyl, C$_{1-6}$ alkyl, aryl-C$_{1-6}$ alkyl, mono- or poly-fluorinated C$_{1-6}$ alkyl, hydroxy-C$_{1-6}$ alkyl, amino-C$_{1-8}$ alky, C$_{1-8}$ alkylamino-C$_{1-8}$ alkyl, di(C$_{1-6}$ alkyl) amino-C$_{1-8}$ alkyl, cyclohexyl, aryl or heterocycle; and R$_3$ and R$_4$ can be taken together to form a 5–7 membered saturated cycle ring or heterocyclic ring.

Chromenylation of 12 can be achieved by reacting with substituted β-hydroxyaldehyde dimethylacetal, affording chromenocoumarin 13. The conditions and amounts of reagents are described above. Representative examples of substituted β-hydroxyaldehyde dimethylacetals of formula c comprise:

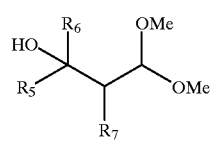

c wherein R$_5$ and R$_6$ are independently selected from the group consisting of H, C$_{1-6}$ alkyl, aryl-C$_{1-6}$ alkyl, mono- or poly-fluorinated C$_{1-6}$ alkyl, aryl or heterocycle; R$_5$ and R$_6$ can be taken together to form a 5–7 membered saturated cycle ring or heterocycle ring; and R$_7$ is H, halogen, methyl, ethyl.

Aldol condensation reaction of chromene 13 with carbonyl compounds in the presence of LDA forms the racemic aldol product (±)-14. According to the present invention, a solution of LDA in THF was added dropwise to a solution of chromene 13 in THF at a temperature ranging between about −78° C. and about 0° C., preferably about −30° C. and about −78° C. The amount of LDA added per mole of chromene 13 ranged between about 1 and about 4 moles, preferably ranging between about 2 and about 3 moles per mole of chromene 13. Dropwise addition of LDA is conducted such that the reaction temperature is maintained within the desired range.

A carbonyl compound of formula iv was then added dropwise to the reaction mixture in amounts ranging between about 1 and about 12 moles, preferably ranging between about 4 and about 6 moles per mole of chromene 13. Dropwise addition of carbonyl compound is conducted such that the reaction temperature is maintained within the aforementioned range. The reaction was monitored by conventional means, e.g., TLC analysis, until it reached completion.-

Representative examples of formula d carbonyl compounds comprise:

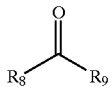

wherein $R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl) amino-$C_{1-8}$ alkyl, cyclohexyl, aryl or heterocycle; and $R_8$ and $R_9$ can be taken together to form a 5–7 membered saturated cycle ring or heterocyclic ring.

One skilled in the art will appreciate that the aldol reaction of chromene 13 with carbonyl compounds of formula d to form 14 can be carried out under conditions which employs bases other than LDA. For example, metal hydroxides such as NaOH, KOH and Ca(OH)$_2$, metal alkoxides such as MeONa, EtONa and t-BuOK, and amines such as pyrrolidine, piperidine, diisopropylethylamine, 1,5-diazabicyclo[4,3,0]non-5-ene (DBN), 1,8-diazabicyclo[5,4,0]undec-7-ene (DBU), NaNH$_2$ and LiHMDS as well as hydrides such as NaH and KH can all be employed for the aldol reactions.[10] Also, aldol reactions can be mediated by metal complexes of Al, B, Mg, Sn, Ti, Zn and Zr compounds such as TiCl$_4$, (i-PrO)$_3$TiCl, (i-PrO)$_4$Ti, PhBCl$_2$, (n-Bu)$_2$BCl, BF$_3$, (n-Bu)$_3$SnCl,SnCl$_4$, ZnCl$_2$, MgBr$_2$, Et$_2$AlCl with or without chiral auxiliaries such as 1,1'-binaphthol, norephedrinesulfonate, camphanediol, diacetone glucose and dialkyl tartrate.[11–13]

Thereafter, the reaction mixture was quenched at −30° C. to −10° C. with saturated aqueous ammonium chloride solution and extracted with a suitable solvent, e.g., ethyl acetate. The pooled extracts were washed with brine and dried over a suitable drying agent, e.g., sodium sulfate. The yields of aldol product (±)-14 generally range between about 40% and about 80%, usually about 70%.

Cyclization of (±)-14 under neutral Mitsunobu conditions, by using triphenylphosphine and diethyl azodicarboxylate (DEAD), leads to formation of chromanone analogue (±)-15. Reduction of (±)-15 with sodium borohydride with or without metal additives such as cerium chloride yields the 12-hydroxy analogue (±)-16 (Scheme V). The conditions and amounts of reagents used in the Mitsunobu and borohydride reduction reactions are described above.

Catalytic hydrogenation of both (±)-15 and (±)-16 produces 7,8-dihydro derivatives (±)-17 and (±)-18 (Scheme VI). To a solution of (±)-15 or (±)-16 in ethanol or ethanol/methylene chloride mixtures in a conventional Parr apparatus under H$_2$, hydrogenation catalyst was added at ambient temperature. The mixture was shaken under hydrogen for a time sufficient to complete the hydrogenation reaction. The solution was then gravity filtered to remove catalyst and solvent was evaporated.

Suitable, but non-limiting, hydrogenation catalysts for use in the invention include Pd/C, PtO$_2$ and Rh/C, Raney-Ni. In making compounds of the invention, 10% palladium/carbon is preferred. The amount of catalyst employed generally ranges between about 0.01 and about 0.5 mole, preferably ranging between about 0.05 and about 0.1 mole per mole of (±)-15 or (±)-16.

In yet another embodiment of the invention, intermediate chromanones (±)-7, (±)-7, (±)-7a and (±)-15 can be used to prepare oxime, hydroxyamino, alkoxyamino or amino calanolide derivatives. Treatment of the said chromanones with hydroxylamine or alkoxyamine affords oxime derivatives (±)-19 (Scheme VI).

Representative amines for preparing oxime derivatives comprise NH$_2$OR$_{10}$ wherein R$_{10}$ is H, C$_{1-8}$ alkyl, phenyl, benzyl, acyl P(O)(OH)$_2$, S(O)(OH)$_2$, CO(C$_{1-10}$ alkyl)CO$_2$H, (C$_{1-8}$ alkyl)CO$_2$H, CO(C$_{1-10}$ alkyl)NR$_{12}$ R$_{13}$, (C$_{1-8}$ alkyl) NR$_{12}$R$_{13}$; wherein R$_{12}$ and R$_{13}$ are independently selected from the group consisting of H, C$_{1-6}$ alkyl; and R$_{12}$ and R$_{13}$ can be taken together to form a 5–7 membered saturated heterocyclic ring containing said nitrogen. Examples of useful alkoxyamines include methoxyamine and benzyloxyamine.

The oxime derivatives may be prepared by refluxing a methanolic solution of the chromanone with hydroxyl amine or alkoxyamine in the presence of a metal carbonate such as potassium carbonate or pyridine until the reaction reaches completion. The amount of amine generally ranges between about 1 and about 20 moles, preferably between about 3 and about 6 moles, per mole of chromanone.

Upon completion of the reaction, filtration of the solution to remove solids and removal of solvent resulted in an oil which was purified via silica gel chromatography. The yields of oximes generally range between about 30% and about 80%, usually about 50%.

If desired, oxime derivatives (±)-19 may be reduced under different conditions[9] to yield hydroxyamino or amino compounds (20 and 21).

Thus, optically active forms of 14–21 (Scheme V and VI) would be obtained by employing enzymatic acylation, as described above, in the procedure outlined in Scheme III for (+)-calanolide A [(+)-1]. Enzyme-catalyzed acylation of the racemic aldol product (±)-14 would selectively acylate one enantiomer [i.e. (−)-14] and leave the other enantiomer [i.e. (+)-14] unreacted, which would be easily separated by conventional methods such as silica gel column chromatography. The acylated enantiomer [i.e. (−)-14] may be hydrolyzed to form the pure enantiomer [i.e. (−)-14]. The optically pure enantiomers thus obtained [(+)-14 and (−)-14] will be cyclized to (+)-15 and (−)-15, respectively, by the Mitsunobu reaction as described above. Subsequent reduction of (+)-15 and (−)-15 would lead to formation of (+)-16 and (−)-16, respectively. Hydrogenation of optically active forms of 15 and 16 would provide pure enantiomers of 17 and 18 [(+)- and (−)-17; (+)- and (−)-18], respectively. Treatment of pure enantiomers of 15 with hydroxylamine or alkoxyamine, as described above, should afford enantiomerically pure oxime 19 [(+)- and (−)-19]. Reduction of (+)-19 and (−)-19 would lead to formation of enantiomerically pure 20 and 21 [(+)- and (−)-20; (+)- and (−)-21].

The 12-hydroxyl group in compound 1, 16, and 17 as well as their optically active forms can be epimerized under a variety of conditions including acidic conditions, neutral Mitsunobu conditions[7a–c], or with DAST.[7d] An example showing conversion of (−)-calanolide A [(−)-1] into (−)-calanolide B using DAST[7d] is depicted in Scheme VII.

Thus, the process used to produce compounds of the present invention may be utilized to prepare a wide variety of calanolide analogues such as Formulas i–v shown in Scheme VIII and Formulas vi–vii shown in Scheme IX.

For Formula i, $R_1$ and $R_2$ are independently ⋯⋯ or ◀.

For Formula ii, $R_1$, $R_2$, and $R_3$ are independently H or CH$_3$.

For Formula iii, $R_1$ is $C_1$–$C_6$ linear or branched alkyl.

For Formula iv, $R_1$ is propyl or phenyl and $R_2$ is ⋯⋯OH or ◀OH.

For Formula vi, $R_1$ is $C_1$–$C_6$ linear or branched alkyl.

For Formula vii, $R_1$ is propyl or phenyl and $R_2$ is ⋯⋯OH or ◀OH.

Additional exemplary calanolide analogues include but are not limited to Formulas 15 and 16 shown in Scheme V, and Formulas 17 and 18 shown in Scheme.

In another embodiment of the invention, (−)-calanolide B, obtained via conversion of (−)-calanolide A, is provided. It has been discovered that (−)-calanolide A may be converted readily to (−)-calanolide B using diethylamidosulfur trifluoride (DAST) or the Mitsunobi reaction, e.g., diethyl azodicarboxylate and triphenylphosphine, under the conditions and ranges described above.

The amount of DAST employed in the inversion reaction generally ranges between about 0.5 and about 5.0 moles, preferably ranging between about 1 and about 2.0 moles, per mole of (−)-calanolide A. Suitable, but non-limiting, reaction solvents for use in the invention include methylene chloride, THF, diethyl ether, or chloroform. In practicing the invention, the preferred solvent is methylene chloride. The reaction may be conducted at a temperature ranging between about −78° C. and about 50° C., preferably about −78° C., until the reaction is complete as determined by usual methods such as thin layer chromatography.

In yet another embodiment of the invention, a method for treating or preventing viral infections in mammals using calanolide analogues of the invention is presented. Examples of mammals include humans, primates, bovines, ovines, porcines, felines, canines, etc. Examples of viruses may include, but not be limited to, HIV-1, HIV-2, herpes simplex virus (type 1 and 2) (HSV-1 and 2), varicella zoster virus (VZV), cytomegalovirus (CMV), papilloma virus, HTLV-1, HTLV-2, feline leukemia virus (FLV), Epstein Barr virus, avian sarcoma viruses such as rous sarcoma virus (RSV), hepatitis types A–E, equine infections, influenza A and B virus, parainfluenza, adenovirus, arboviruses, respiratory syncytial virus, measles, mumps and rubella viruses. More preferably the compounds of the present invention will be used to treat a human infected with HIV, Hepatitis B, cytomegalovirus, Epstein Barr virus, or measles.

Hence the compounds of the present invention are particularly useful in the prevention or treatment of infection by the human immunodeficiency virus and also in the treatment of consequent pathological conditions associated with AIDS. Treating AIDS is defined as including, but not limited to, treating a wide range of states of HIV infection: AIDS, ARC, both symptomatic and asymptomatic, and actual or potential exposure to HIV. For example, the compounds of this invention are useful in treating infection of HIV after suspected exposure to HIV by e.g., blood transfusion, exposure to patient blood during surgery or an accidental needle stick.

Antiviral calanolide analogues of the invention may be formulated as a solution of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium chloride or sodium citrate.

Alternatively, the compounds of the present invention may be encapsulated, tableted or prepared in an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or colloidal silicon dioxide. Liquid carriers include syrup, peanut oil, olive oil, corn oil, sesame oil, saline and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of antiviral calanolide analogues of the invention are those to produce the desired affect whereby symptoms of infection are ameliorated. For example, as used herein, a pharmaceutically effective amount for an HIV or other viral infection refers to the amount administered so as to maintain an amount which suppresses or inhibits secondary infection by syncytia formation or by circulating virus throughout the period during which the HIV or other viral infection is evidenced, such as by presence of antiviral antibodies, presence of culturable virus and presence of antigen in patient sera. For example, the presence of anti-HIV antibodies can be determined through use of standard ELISA or Western blot assays, e.g., anti-gp120, anti-gp41, anti-tat, anti-p55, anti-p17, antibodies, etc. The dosage will generally vary with age, extent of the infection, the body weight and counterindications, if any, for example, immune tolerance. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 50 mg/kg/day, but preferably between about 0.01 to about 1.0 mg/kg/day. For viral infections other than HIV, antiviral activity can be shown via other standard assays. For example, calanolide analogue antiviral efficacy against HSV, CMV, and VZV can be determined by cytopathic effect (CPE) inhibition assay. Similarly, calanolide analogue efficacy against HSV-1, HSV-2, VZV, CMV can be determined by plaque reduction assay. In this method, the reduction of plaque on a treated agar plate is compared to an untreated control. Calanolide analogue efficacy against EBV can be determined by immunofluoresence assay, where monoclonal antibodies and fluorescin conjugated anti-mouse antibody are sequentially added to incubated cell cultures infected with EBV, with the number of fluorescence positive cells in smears ultimately counted.

The pharmaceutical composition may contain other pharmaceuticals in conjunction with the antiviral calanolide analogues of the invention. For example, other pharmaceuticals may include, but are not limited to, other antiviral compounds (e.g., AZT, ddC, ddI, D4T, 3TC, acyclovir, gancyclovir, fluorinated nucleosides and nonnucleoside analog compounds such as TIBO derivatives and nevirapine, α-interfon and recombinant CD4), protease inhibitors (e.g., indinavir, saquinavir, ritonavir, and nelfinavir), immunostimulants (e.g., various interleukins and cytokines), immunomodulators, antibiotics (e.g., antibacterial, antifungal, anti-pneumocysitis agents), and chemokine inhibitors. Administration of the inhibitory compounds with other anti-retroviral agents that act against other HIV proteins such as protease, intergrase and TAT will generally inhibit most or all replicative stages of the viral life cycle.

The calanolide analogues described herein can be used either alone or in conjunction with other pharmaceutical compounds to effectively combat a single infection. For example, calanolide analogues of the invention can be used either alone or combined with acyclovir in a combination therapy to treat HSV-1. Calanolide analogues can also be used either alone or in conjunction with other pharmaceutical compounds to combat multiple infections. For example, calanolide analogues can be used in combination with Intron A and/or a biflavanoid for treating Hepatitis B; with gancyclovir, progancyclovir, famcyclovir, foscamet, vidarabine, cidovir, and/or acyclovir for treating herpes viruses; and with ribavarin, amantidine, and/or rimantidine for treating respiratory viruses.

In addition, the compounds of the present invention are useful as tools and/or reagents to study inhibition of retroviral reverse transcriptases. For example, the instant compounds selectively inhibit HIV reverse transcriptase. Hence, the instant compounds are useful as a structure/activity relationship (SAR) tool to study, select and/or design other molecules to inhibit HIV.

The following examples are illustrative and do not serve to limit the scope of the invention as claimed. The inhibitory activities against HIV and other viruses including hepatitis B, herpes viruses (HSV-1, HSV-2, HCMV, VZV, and Epstein Barr virus), and respiratory viruses (influenza A, influenza B, parainfluenza, adenovirus, measles, and respiratory syncytial virus) were investigated.

EXPERIMENTAL

All chemical reagents and solvents referred to herein are readily available from a number of commercial sources including Aldrich Chemical Co. or Fischer Scientific. NMR spectra were run on a Hitachi 60 MHz R-1200 NMR spectrometer or a Varian VX-300 NMR spectrometer. IR spectra were obtained using a Midac M series FT-IR instrument. Mass spectral data were obtained using a Finnegan MAT 90 mass spectrometer. All melting points are corrected.

EXAMPLE 1

5,7-Dihydroxy4-propylcoumarin[5] (2)

Concentrated sulfuric acid (200 mL) was added into a mixture of phloroglucinol dihydrate (150 g, 0.926 mol) and ethyl butyrylacetate (161 g, 1.02 mol). The resulting mixture was stirred at 90° C. for two hours whereupon it was poured onto ice. The solid product was collected by filtration, and then dissolved in ethyl acetate. The solution was washed with brine and dried over $Na_2SO_4$. After removal of the solvent in vacuo, the residue was triturated with hexane to provide essentially pure compound 2 (203 g) in quantitative yield, mp 233–235° C. (Lit.[5] 236–238° C.). $^1$H-NMR[5] (DMSO-$d_6$) δ0.95 (3H, t, J=6.9 Hz, $CH_3$); 1.63 (2H, apparent sextet, J=7.0 Hz, $CH_2$); 2.89 (2H, t, J=7.5Hz, $CH_2$); 5.85 (1H, s, $H_3$); 6.22 (1H, d, J=2.0 Hz, $H_6$); 6.31 (1H, d, J=2.0 Hz, $H_8$); 10.27 (1H, s, OH); 10.58 (1H, s, OH); MS (EI): 220(100, M$^+$); 205 (37.9, M-1055 $CH_3$); 192 (65.8, M-$C_2H_4$); 177 (24.8, M-$C_3H_7$); 164 (60.9, M-$CHCO_2$+1); 163 (59.6 M-$CHCO_2$); IR (KBr): 3210 (vs and broad, OH); 1649 (vs, sh); 1617 (vs, sh); 1554 (s) cm$^{-1}$; Anal. calcd. for $C_{12}H_{24}O_4$: C, 65.45; H, 5.49; Found: C, 65.61; H, 5.44.

EXAMPLE 2

5,7-Dihydroxy-8-propionyl4-propylcoumarin (3)

A three-neck flask (500 mL) equipped with an efficient mechanical stirrer, thermometer and addition funnel was charged with 5,7-dihydroxy-4-propylcoumarin, 2, (25.0 g, 0.113 mol), aluminum chloride (62.1 g; 0.466 mol), and nitrobenzene (150 mL) and the mixture was stirred until a solution was obtained, which was cooled to 0° C. in an ice bath. A solution of propionyl chloride (15.2 g; 0.165 mol) in carbon disulfide (50 mL) was added dropwise at such a rate that the reaction temperature was maintained at 8–10° C. Addition was completed over a period of 1 hour with vigorous stirring. The reaction was monitored by TLC using a mobile phase of 50% ethyl acetate/hexane. After three hours, an additional portion of propionyl chloride (2.10 g; 0.0227 mol) in carbon disulfide (10 mL) was added. Immediately after the TLC analysis indicated the total consumption of starting material, the reaction mixture was poured onto ice, and allowed to stand overnight. The nitrobenzene was removed by steam distillation, and the remaining solution was extracted several times with ethyl acetate. The extracts were combined and dried over $Na_2SO_4$. The crude product obtained by evaporation in vacuo was purified by chromatography on a silica gel column eluting with 50% ether/hexane to provide the desired propionylated coumarin 3, mp 244–246° C. $^1$H-NMR (DMSO-$d_6$) δ0.96 (3H, t, J=7.3 Hz, $CH_3$); 1.10 (3H, t, J=7.2 Hz, $CH_3$); 1.60 (2H, m, $CH_2$); 2.88 (2H, t, J=7.7 Hz, $CH_2$); 3.04 (2H, q, J=7.2 Hz, $CH_2$); 5.95 (1H, s, $H_3$); 6.31 (1H, s, $H_6$); 11.07 (1H, s, OH); 11.50 (1H, s, OH); MS (EI): 277 (6.6, M+1); 276 (9.0, M$^+$); 247 (100, M-$C_2H_5$); IR (KBr): 3239 (s and broad, OH); 1693 (s, C=O), 1625 and 1593 (s) cm$^{-1}$; Anal. calcd. for $C_{15}H_{16}O_5$: C, 65.21; H, 5.84; Found: c, 64.92; H, 5.83. The isomer assignment was made by analogy to precedent.[15]

EXAMPLE 3

2,2-Dimethyl-5-hydroxy-6-propionyl-10-propyl-2H, 8H-benzo[1,2-b:3,4-b']dipyran-8one (4)

A mixture of 3 (2.60 g, 9.42 mmol) and 4,4-dimethoxy-2-methylbutan-2-ol (5.54 g, 37.7 mmol) were dissolved in anhydrous pyridine (6.5 mL). The mixture was refluxed under nitrogen for three days. After removal of the solvent in vacuo, the residue was dissolved in ethyl acetate. The ethyl acetate was washed several times with 1 N HCl and brine. It was then dried over $Na_2SO_4$. The crude product obtained by evaporation in vacuo was purified by silica gel column chromatography, eluting with 25% ethyl acetate/hexane to afford 2.55 g of 4 in 78.6% yield, mp 96–98° C. $^1$H-NMR (CDCl$_3$) δ1.05 (3H, t, J=7.3 Hz, $CH_3$); 1.22 (3H, t, J=7.5 Hz, $CH_3$); 1.53 (6H, s, 2 $CH_3$); 1.75 (2H, m, $CH_2$); 2.92 (2H, t, J=7.1 Hz, $CH_2$); 3.35 (2H, q, J =7.1 Hz, $CH_2$); 5.56 (1H, d, J=10.0 Hz, $H_3$); 5.98 (1H, s, $H_9$); 6.72 (1H, d, J=10.0 Hz, $H_4$); MS (EI): 343 (5.7, M+1); 342 (22.5, M$^{30}$); 327 (100, M—$CH_3$); IR (KBr): 1728 (vs, C=O) cm$^{-1}$;

Anal. calcd. for $C_{20}H_{22}O_5$: C, 70.16; H, 6.48; Found: C, 70.45; H, 6.92.

EXAMPLE 4

10,11-Didehydro-12-oxocalanolide A (5)

A mixture of 4 (1.76 g, 5.11 mmol) and sodium acetate (0.419 g, 5.11 mmol) in acetic anhydride (12 mL) were refluxed for 10 hours whereupon the solvent was removed in vacuo. The residue was purified by silica gel column chromatography, eluting first with 25% ethyl acetate/hexane followed by 50% ethyl acetate/hexane to provide 1.16 g (62% yield) of enone 5 (6,6,10,11-tetramethyl-4-propyl-2H, 6H, 12H-benzo[1,2-b:3,4-b':5,6-b"]tripyran-2,12-dione) as a white solid, mp 209–209.5° C. $^1$H-NMR (CDCl$_3$) δ1.05

(3H, t, J=6.6 Hz, $CH_3$); 1.56 (6H, s, 2 $CH_3$); 1.73 (2H, m, $CH_2$); 1.98 (3H, s, $CH_3$); 2.38 (3H, s, $CH_3$); 2.91 (2H, t, J=7.5 Hz, $CH_2$); 5.69 (1H, d, J=10.0 Hz, $H_7$); 6.11 (1H, s, $H_3$); 6.71 (1H, d, J=10 Hz, $H_8$); MS (EI): 366 (29.6, M$^+$); 351 (100, M-$CH_3$); 323 (16.5, M-$C_3H_7$); IR (KBr): 1734 (vs, C=O), 1657, 1640, 1610, and 1562 cm$^{-1}$; Anal. calcd. for $C_{22}H_{22}O_5$: 72.12; H, 6.05; Found: C, 72.14; H, 6.15.

EXAMPLE 5

10,11-Didehydrocalanolide A (6)

A mixture of enone 5 (160 mg, 0.437 mmol) and tri-n-butyltin hydride (0.318 g, 1.09 mmol) in dry dioxane (2.0 mL) was refluxed under nitrogen for 12 hours. The solvent was then removed in vacuo and the residue was purified by preparative TLC using 25% ethyl acetate in hexane as the mobile phase. The product exhibited an $R_f$ of about 0.4. Enol 6 (12-hydroxy-6,6,10,11-tetramethyl-4-propyl-2H,6H,12H-benzo[1,2-b:3,4-b':5,6-b"]tripyran-2-one) (13.3 mg, 8%) was isolated as an oil from the plate by ethyl acetate elution. This elution may have been inefficient, and the actual yield higher, as indicated by analytical TLC of the crude product. $^1$H-NMR (CDCl$_3$) δ0.92 (3H, t, J=6.0 Hz, $CH_3$); 1.26 (3H, s, $CH_3$); 1.39 (3H, s, $CH_3$); 1.63 (2H, m, $CH_2$); 1.96 (3H, s, $CH_3$); 2.36 (3H, s, $CH_3$); 2.45 (2H, t, J=6.0 Hz, $CH_2$); 3.65 (1H, s, $H_{12}$); 5.51 (1H, d, J=10.0 Hz, $H_7$); 6.06 (1H, S, $H_3$); 6.67 (1H, d, J=10.0 Hz, $H_8$); 13.25 (1H, br s, OH); MS (EI): 369 (3.8, M+1), 368 (4.4, M$^+$, 367 (8.3, M−1) 366 (28.4, M−2), 351 (100, M—OH); IR(KBr): 1651 (s), 1589 (m)cm$^{-1}$.

EXAMPLE 6

12-Oxocalanolide A [(±)-(7)

A solution containing chromene 4 (344 mg, 1.0 mmol), acetaldehyde diethylacetal (473 mg, 4.0 mmol), trifluoroacetic acid (1.5 mL, 19.4 mmol) and anhydrous pyridine (0.7 mL) was heated at 140° C. under $N_2$. The reaction was monitored by TLC analysis. After 4 hours, the reaction mixture was cooled to room temperature, diluted with ethyl acetate and washed several times with 10% aqueous NaHCO$_3$ and brine. The organic layer was separated and dried over Na$_2$SO$_4$. The solvent was removed in vacuo and the crude product was purified by silica gel column chromatography eluting with ethyl acetate/hexane (2:3). Chromanone (±)-7 (10,11-trans-dihydro-4-propyl-6,6,10,11-tetramethyl-2H,6H,12H-benzo[1,2-b:3,4-b':5,6-b"]-tripyran-2,12-dione) (110 mg, 30% yield) was obtained m.p. 176–177° C. (Lit.$^5$ 130–132° C.). $^1$HNMR$^5$ (CDCl$_3$) δ1.02 (3H, t, J=7.5 Hz, $CH_3$); 1.21 (3H, d, J=6.8 Hz, $CH_3$); 1.51 (3H, d, J=7.0 Hz, $CH_3$); 1.55 (6H, 2s, 2 $CH_3$); 1.63 (2H, sextet, J=7.0 Hz, $CH_2$); 2.55 (1H, dq, J=6.9 Hz, J=11.0 Hz, $H_{11}$); 2.88 (2H, t, J=7.6 Hz, $CH_2$); 4.28 (1H, dq, J=6.3 Hz, J=11.0 Hz, $H_{10}$); 5.60 (1H, d, J=9.9 Hz, $H_7$); 6.04 (1H, s, $H_3$); 6.65 (1H, d, J=11.8 Hz, $H_8$); MS (CI): 369 (100, M+1).

EXAMPLE 7

(±)-Calanolide A (1)

To a solution of chromanone (±)-7 (11 mg, 0.03 mmol) in ethanol (0.4 mL) was added sodium borohydride (2.26 g, 0.06 mmol) and CeCl$_3$(H$_2$O)$_7$ (11.2 mg, 0.03 mmol) in ethanol (5 mL) at room temperature. After stirring for 45 minutes, the mixture was diluted with H$_2$O and extracted with ethyl acetate. The organic layer was dried over Na$_2$SO$_4$ and concentrated. The crude product was purified by preparative TLC eluting with ethyl acetate/hexane (1:1) to afford (±)-calanolide A (1) (10.5 mg, 94%). m.p. 52–54° C., which increased to 102° C. after it was dried thoroughly (Lit$^5$. 56–58° C.). $^1$H NMR (CDCl$_3$): δ1.03 (3H, t, J=7.3 Hz, $CH_3$), 1.15 (3H, d, J=6.8 Hz, $CH_3$), 1.46 (3H, d, J=6.8 Hz, $CH_3$), 1.47 (3H, s, $CH_3$), 1.51 (3H, s, $CH_3$), 1.66 (2H, m, $CH_2$), 1.93 (1H, m, $H_{11}$), 2.89 (2H, m, $CH_2$), 3.52 (1H, broad-s, OH), 3.93 (1H, m, $H_{10}$), 4.72 (1H, d, J=7.8 Hz, $H_{12}$), 5.54 (1H, d, J=10.0 Hz, $H_7$), 5.94 (1H, s, $H_3$) 6.62 (1H, d, J=9.9 Hz, $H_8$); MS (CI): 371 (75.4, M+1), 370 (16.1, M$^+$), 353 (100, M-OH); Anal. calcd. for $C_{22}H_{25}O_5$: C, 71.33; H, 7.07; Found: C, 71.63; H, 7.21.

EXAMPLE 8

5,7-Dihydroxy4-propylcoumarin (2)

In this Example, kilogram scale preparation of intermediate 2 is described. Into a stirring suspension of phloroglucinol (3574.8 g, 28.4 mol, pre-dried to constant weight) and ethyl butyrylacetate (4600 mL, 28.4 mol) was added concentrated sulfric acid dropwise at such a rate that the internal temperature did not exceed 40° C. After 100 mL of sulfuric acid was added, the temperature rose to 70° C. and the suspension turned into a yellow solid. Analysis of TLC indicated that the reaction had proceeded to completion. The reaction mixture was diluted with water (10 L) and stirred at ambient temperature overnight. The precipitated product was collected by filtration and then rinsed with water until the filtrate was neutral. A quantity of 4820 g (77% yield) of 5,7-dihydroxy-4-propylcoumarin 2 was obtained after being dried, which was identical with an authentic sample by comparison of TLC, melting point and spectroscopic data.

EXAMPLE 9

5,7-Dihydroxy-8-propionyl4-propylcoumarin (3)

In this Example, kilogram quantities of intermediate 3 were synthesized using propionic anhydride instead of propionyl chloride. 5,7-dihydroxy-4-propylcoumarin 2 (1710 g, 7.77 mol) and AlCl$_3$ (1000 g, 7.77 mol) were mixed in 1,2-dichloroethane (9 L). The resulting orange suspension was stirred and heated to 70° C. until a solution was obtained. Then, a mixture of propionic anhydride (1010 g. 7.77 mol) and AlCl$_3$ (2000 g, 15.54 mol) in 1,2-dichloroethane (3.4 L) was added dropwise over 3 h. The reaction was allowed to stir at 70° C. for an additional hour. After being cooled down to room temperature, the reaction mixture was poured into a rapidly stirring mixture of ice water and 1N HCl. The precipitated product was taken into ethyl acetate (30 L) and the aqueous solution was extracted with the same solvent (10 L×2). The combined extracts were successively washed with 1 N HCl (10 L), saturated aq. NaHCO$_3$ (10 L), and water (10 L). After being dried over MgSO$_4$ and concentrated in vacuo, a solid product (1765 g) was obtained which was washed with ethyl acetate (15 L) and recrystallized from dioxane (9.5 L) to provide 514 g of pure compound 3. From the ethyl acetate washings, an additional 100 g of compound was obtained after recrystallization from dioxane. Thus, the combined yield for compound 3, which was identical with an authentic sample by comparison of TLC, melting point and spectroscopic data, was 29%.

EXAMPLE 10

2,2-Dimethyl-5-hydroxy-6propionyl-10propyl-2H, 8H-benzo[1,2-b:3,4b']dipyran-8-one (4)

In this Example, intermediate 4 was prepared in half kilogram quantities from 3 via modification of the reaction conditions described in Example 3. A mixture of compound 3 (510.6 g, 1.85 mol) and 4,4-dimethoxy-2-methylbutan-2-ol (305.6 g, 2.06 mol) were dissolved in a mixture of toluene (1.5 L) and dry pyridine (51 mL). This mixture was stirred and refluxed; water and methanol formed during the reaction were removed azeotropically via a Dean-Stark trap. The reaction was monitored by TLC. After 6 days, the reaction had proceeded to completion. The mixture was then cooled to ambient temperature and diluted with ethyl acetate (2 L) and 1 N HCl (1 L). The ethyl acetate solution was separated and washed with 1N HCl (500 mL) and brine (1 L). After being dried over $Na_2SO_4$ and evaporated in vacuo, a quantity of 590 g (93% yield) of compound 4 was obtained which was greater than 95% pure without further purification and was compared with an authentic sample by TLC and spectroscopic data.

EXAMPLE 11

12-Oxocalanolide A ((±)-7)

In this Example, chromanone (±)-7 was prepared from two alternative pathways involving either a one-step paraldehyde reaction (procedure A) or a two-step reaction process (procedures B and C).

Procedure A. Paraldehyde One-Step Reaction: To a stirring solution of chromene 4 (350 mg, 1.0 mmol) and PPTS (250 mg, 1.0 mmol) in 1,2-dichloroethane (2 mL) at ambient temperature under $N_2$ was added 3 mL paraldehyde (22.5 mmol). The resulting mixture was refluxed for 7 h. Then, $CF_3CO_2H$ (1 mL), an additional equivalent of PPTS and 1 mL of paraldehyde were added; the mixture was refluxed overnight. The reaction mixture was neutralized with saturated aqueous $NaHCO_3$ and extracted with ethyl acetate (50 mL×3). The crude product obtained by evaporation under reduced pressure was washed with hexane. The residue was purified by column chromatography eluting with ethyl acetate/hexane (1:2) to afford 100 mg (27% yield) of chromanone (±)-7 and 30 mg (8% yield) of (±)-7a. Chromanone (±)-7 (10,11 -trans-dihydro-4-propyl-6,6,10,11-tetramethyl-2H,6H,12H-benzo[1,2-b:3,4-b':5,6-b"]tripyran-2,12-dione) obtained by this method was identical with an authentic sample by comparison of TLC, PLC and spectroscopic data.

Procedure B LDA/Sulfuric Acid Two-Step Reaction: To a stirring solution of chromene 4 (5.0 g, 14.6 mmol) in THF (75 mL) at −30° C. under $N_2$ was added 18.3 mL (36.5 mmol) of 2 M LDA in THF. After 15 min at the same temperature, acetaldehyde (5.0 mL, 89.5 mmol) was added via syringe. The reaction was monitored by TLC analysis. After 1 h, the reaction mixture was quenched at −10° C. with saturated aqueous $NH_4Cl$ (75 mL) and extracted with ethyl acetate (125 mL×3). The combined extracts were washed with brine (125 ml) and dried over $Na_2SO_4$. Removal of solvents in vacuo afforded a reddish oil of (±))-8a and (±)-8b (8.5 g).

The crude (±)-8a and (±)-8b was dissolved in acetic acid (100 mL) and then 50% $H_2SO_4$ (100 mL) was added with stirring. The resulting mixture was heated at 75° C. for 2.5 h and then at 50° C. for 4 h. TLC analysis indicated that the starting material had been consumed. The reaction mixture was determined to contain both chromanone (±)7 and 10,11-cis-dimethyl derivative (±)-7a in a 1:1 ratio. After cooling to ambient temperature, the reaction mixture was poured into a mixture of ice water (500 mL) and ethyl acetate (500 mL). The layers were separated and the aqueous layer was extracted with ethyl acetate (200 mL×3). The ethyl acetate solutions were combined and washed with saturated aqueous $NaHCO_3$ and brine. After being concentrated in vacuo, the product was purified by chromatography on a silica gel column eluting with ethyl acetate/hexane (2:3) to provide 850 mg (16% yield) of chromanone (±)-7, which was further purified by recrystallization from ethyl acetate/hexane and was identical with an authentic sample by comparison of TLC, HPLC and spectroscopic data.

Procedure C. LDA/Mitsunobu Two-Step Reaction: Into a stirring solution of THF (10 mL) containing triphenylphosphine (1.27 g, 4.80 mmol) and the crude mixture of (±)-8a and (±)-8b, obtained from chromene 4 (1.0 g, 2.34 mmol), 2.5 equivalents of LDA and 6.0 equivalents of acetaldehyde by the procedure described above, was added dropwise diethyl azodicarboxylate (DEAD, 0.77 mL, 4,89 mmol). The resulting reddish solution was stirred at ambient temperature under $N_2$ for 1 h, after which the reaction mixture was quenched with saturated aqueous $NH_4Cl$ and extracted with ethyl acetate (50 mL×3). The extracts were washed with brine and dried over $Na_2SO_4$. After removal of solvents, the crude product was purified by column chromatography on silica gel eluting with ethyl acetate/hexane (2:3) to provide 412 mg (48% yield, based on chromene 4) of chromanone (±)-7, the predominant product of the reaction, which was identical with an authentic sample by comparison of TLC, HPLC and spectroscopic data.

EXAMPLE 12

(±)-Calanolide A (1)

In this Example, (±)-calanolide A was prepared in multi-gram scale using the procedure described in Example 7. To a stirring solution of chromanone (±)-7 (51.5 g, 0.14 mol) in ethanol (1.5 L) was added $CeCl_3(H_2O)_7$ (102 g, 274 mmol). The mixture was stirred for 1.5 h at room temperature under $N_2$ and then cooled to −30° C. with an ethylene glycol/$H_2O$ (1:2 w/w) dry ice bath. After the temperature was equilibrated to −30° C. , $NaBH_4$ (21.3 g, 563 mmol) was added and stirred at the same temperature for 8.5 h, at which time the reaction was quenched with $H_2O$ (2 L) and extracted with ethyl acetate (2 L×3). The extracts were combined, washed with brine (2 L) and dried over $Na_2SO_4$. The crude product obtained by removal of solvent under reduced pressure was passed through a short silica gel column to provide 53 g of mixture which contained 68% of (±)-calanolide A, 14% of calanolide B and 13% of chromanone (±)-7 as shown by HPLC. This material was subjected to further purification by preparative HPLC to afford pure (±)-calanolide A (1).

EXAMPLE 13

Chromatographic Resolution of Synthetic ±-Calanolide A

The synthetic ±-1 was resolved into enantiomers, (+)-calanolide A and (−)-calanolide A, by preparative HPLC[16]. Thus, using a normal phase silica gel HPLC column (250 mm×4.6 mm I.D. Zorbasil, 5 μm particle size, MAC-MOD Analytical, Inc., PA, USA), the synthetic (±)-1 appeared as one peak with a retention time of 10.15 minutes when hexane/ethyl acetate (70:30) was used as the mobile phase at a flow rate of 1.5 mL/min and a wavelength of 290 nm was used as the uv detector setting. However, on a chiral HPLC column packed with amylose carbamate (250 mm×4.6 mm I.D. Chiralpak AD, 10 μm particle size, Chiral Technologies, Inc., PA, USA), two peaks with retention times of 6.39 and 7.15 minutes in a ratio of 1:1 were observed at a flow rate of 1.5 mL/min. The mobile phase was hexane/ethanol (95:5) and the uv detector was set at a wavelength of 254 nm. These two components were separated using a semi-preparative chiral HPLC column, providing the pure enantiomers of calanolide A. The chemical structures of the separated enantiomers, which were assigned based on their optical rotations and compared with the reported natural product, were characterized by spectroscopic data. HPLC chromatograms of (±)-calanolide A and its optical forms are shown in FIG. 6.

(+)-Calanolide A (1): mp 47–50° C. (Lit.[17] 45–48° C.);[α]$^{25}_D$=+68.8° (CHCl$_3$, c 0.7) (Lit.[17] [α]$^{25}_D$=+66.6°) (CHCl$_3$; c 0.5); $^1$H NMR (CDCl$_3$) δ1.03 (3H, t, J=7.3 Hz, CH$_3$), 1.15 (3H, d, J=6.8 Hz, CH$_3$), 1.46 (3H, d, J=6.4 Hz, CH$_3$), 1.47 (3H, s, CH$_3$), 1.51 (3H, s, CH$_3$), 1.66 (2H, m, CH$_2$), 1.93 (1H, m, H$_{11}$), 2.89 (2H, m, CH$_2$), 3.52 (1H, d, J=2.9 Hz, OH), 3.93 (1H, m, H$_{10}$), 4.72 (1H, dd, J=7.8 Hz, J=2.7 Hz, H$_{12}$), 5.54 (1H, d, J=9.9 Hz, H$_7$), 5.94 (1H, s, H$_3$), 6.62 (1H, d, J=9.9 Hz, H$_8$); $^{13}$C NMR (CDCl$_3$) 13.99 (CH$_3$), 15.10 (CH$_3$), 18.93 (CH$_3$), 23.26 (CH$_2$), 27.38 (CH$_3$), 28.02 (CH$_3$), 38.66 (CH$_2$), 40.42 (CH), 67.19 (CH—OH), 77.15 (CH—O), 77.67 (C—O), 104.04 (C$_{4a}$), 106.36 (C$_{8a}$ and C$_{12a}$), 110.14 (C$_3$), 116.51 (C$_8$), 126.97 (C$_7$), 151.14 (C$_{4b}$), 153.10 (C$_{8b}$), 154.50 (C$_{12b}$), 158.88 (C$_4$), 160.42 (C=O); CIMS: 371 (100, M+1), 370 (23.6, M$^+$), 353 (66.2, M—OH); 1R: 3611 (w) and 3426 (m, broad, OH), 1734 (vs. C=O), 1643 (m), 1606 (m) and 1587 (vs) cm$^{-1}$; UV λ$_{max}$ (methanol): 204 (32,100), 228 (23,200), 283 (22,200), 325 (12,700) nm; Anal. calcd. for C$_{22}$H$_{26}$O$_5$1/4H$_2$O: C, 70.47; H, 7.12; Found: C, 70.64; H, 7.12.

—-Calanolide A (1): mp 47–50° C.;[α]$^{25}_D$=−75.6° (CHCl$_3$, c 0.7) Lit.[17][α]$^{25}_D$=−66.6° (CHCl$_3$, c 0.5); $^1$H NMR (CDCl$_3$) δ1.03 (3H, t, J=7.4 Hz, CH$_3$), 1.15 (3H, d, J=6.8 Hz, CH$_3$), 1.46 (3H, d, J=6.3 Hz, CH$_3$), 1.47 (3H, s, CH$_3$), 1.51 (3H, s, CH$_3$) 1.66 (2H, m, CH$_2$), 1.93 (1H, m, H$_{11}$), 2.89 (2H, m, CH$_2$), 3.50 (1H, d, J=2.9 Hz, OH), 3.92 (1H, m, H$_{10}$), 4.72 (1H, dd, J=7.8 Hz, J=2.7 Hz, H$_{12}$), 5.54 (1H, d, J=10.0 Hz, H$_7$), 5.94 (1H, s, H$_3$), 6.62 (1H, d, J=10.0 Hz, H$_8$); $^{13}$C NMR (CDCl$_3$) δ13.99 (CH$_3$), 15.10 (CH$_3$), 18.93 (CH$_3$), 23.36 (CH$_2$), 27.38 (CH$_3$), 28.02 (CH$_3$), 38.66 (CH$_2$), 40.42 (CH), 67.19 (CH—OH), 77.15 (CH—O), 77.67 (C—O), 104.04 (C$_{4a}$), 106.36 (C$_{8a}$ and C$_{12a}$), 110.14 (C$_3$), 116.51 (C$_8$), 126.97 (C$_7$), 151.14 (C$_{4b}$), 153.11 (C$_{8b}$), 154.50 (C$_{12b}$), 158.90 (C$_4$), 160.44 (C=O); CIMS: 371 (95.2, M+1), 370 (41.8,M$^+$), 353 (100, M-OH); IR: 3443 (m, broad, OH), 1732 (vs, C=O), 1643 (m), 1606 (m) and 1584 (vs) cm$^{-1}$; UV λ$_{max}$ (methanol): 200 (20,500), 230 (19,400), 283 (22, 500), 326 (12,500) nm; Anal. calcd. for (C$_{22}$ H$_{26}$O$_5$1/4H$_2$O: C, 70.47; H, 7.12; Found: C, 70.27; H, 7.21.

EXAMPLE 14

Enzymatic Resolution of (±)-Calanolide A

To a magnetically stirred suspension of (±)-calanolide A, prepared by the method of the present invention, and vinyl butyrate (0.1 mL) in hexane (0.5 mL) at ambient temperature was added 1 mg of lipase PS-13 (Pseudomonas Species) (Sigma Corporations, St. Louis, Mo., USA). The reaction mixture was stirred and monitored by conventional means such as TLC analysis. At 10 days, an additional 1 mg of lipase PS-13 was added. After stirring for a total of 20 days, the reaction was stopped because there was no obvious increase in ester formation. The enzyme was filtered out and the filtrate was concentrated to dryness. The residue was analyzed by HPLC (see Example 13), which showed that 21% of (−)-calanolide A had been converted into its butyrate ester form. The enriched (+)-calanolide A and the butyrate ester of (−)-calanolide A can be easily separated by conventional means such as column chromatography. The enriched (+)-calanolide A may be repeatedly treated with vinyl butyrate and lipase PS-13 as described above so as to obtain high e.e. of (+)-calanolide A.

EXAMPLE 15

Aldol Reaction (Scheme III) of Chromene 4 in the Presence of LDA

To a stirring solution of chromene 4 (1.0 g, 2.9 mmol) in THF (15 mL) at -78 ° C. under N$_2$ was added 2 M LDA in THF (3.2 mL, 6.4 mmol). After 1 h at the same temperature, acetaldehyde (1.0 mL, 17.5 mmol) was added via syringe. The reaction was monitored by TLC analysis. After 1 h, the reaction mixture was quenched with a precooled 2 N HCl in methanol (15 mL) and extracted with ethyl acetate (30 mL×3). The combined extracts were washed with brine and dried over Na$_2$SO$_4$. Removal of solvents in vacuo afforded a reddish oil, which was purified by silica gel column chromatography eluting with a discontinuous gradient of 5%, 10%, 15%, 25% and 30% of ethyl acetate in hexane to obtain 780 mg (70% yield) of a mixture of (±)-8a and (±)-8b in a ratio of 1:1, as indicated by $^1$H NMR. Pure samples of (±)-8a and (±) -8b were obtained by carefully collecting the front fractions and later fractions from column chromatography, analytical data of which were described below:

6,6-Dimethyl-9-hydroxy-10-[2(S*)-methyl-3(R*)-hydroxybutyro]-4-propyl -2H,6H-benzo[1,2-b:3,4b'] dipyran-2-one

[syn-(±) 8a]. m.p. 66–67° C.; $^1$H NMR (CDCl$_3$): 1.05 (3H, t, J=7.3 Hz, CH$_3$), 1.30 (3H, d, J=6.0 Hz, CH$_3$), 1.33 (3H, d, J=6.6 Hz, CH$_3$), 1.54 (6H, s, 2 CH$_3$), 1.67 (2H, m, CH$_2$), 2.62 (1H, broad-s, OH), 2.91 (2H, t, J=7.7 Hz, CH$_2$), 3.98 (1H, dq, J=2.7 Hz, J=7.0 Hz, H$_2$·), 4.29 (1H, m, H$_3$·), 5.59 (1H, d, J=10.0 Hz, H$_7$), 6.01 (1H, s, H$_3$), 6.73 (1H, d, J=10.0 Hz, H$_8$), 14.11 (1H, s, OH); 1H NMR (DMSO-d$_6$): 1.00 (3H, t, J=7.3 Hz, CH$_3$), 1.13 (3H, d, J-6.6 Hz, CH$_3$), 1.16 (3H, d, J=6.8 Hz, CH$_3$), 1.49 (3H, s, CH$_3$), 1.50 (3H, s, CH$_3$), 1.60 (2H, apparent sextet, J=7.6 Hz, CH$_2$), 2.88 (2H, apparent dd, J=6.3 Hz, J=9.0 Hz, CH$_2$), 3.39 (1H, broad-s, OH), 3.68 (1H, dq, J=5.2 Hz, J=6.7 Hz, H$_2$·), 3.97 (1H, apparent quintet, J=5.8 Hz, H$_3$·), 5.78 (1H, d, J=10.1 Hz, H$_7$), 6.11 (1H, s, H$_3$), 6.63 (1H, d, J=10.1 Hz, H$_8$), 13.25 (1H, s, OH); MS (CI): 388 (36.5, M+2), 387 (100, M+1), 386 (6.6, M$^+$), 369 (21.6, M -OH), 343 (50.7, M-C$_3$H$_7$); UV λ$_{max}$ (methanol) nm: 199 (41,000), 270 (25,700), 306 (21, 900); IR (KBr) cm$^{-1}$: 3395 (broad, m, OH), 1734 (s) and 1707 (vs) (C=O), 1644 (m), 1608 (vs), 1578 (vs) and 1547 (vs); Anal. Calcd. for C$_{22}$H$_{26}$O$_6$.1/3H$_2$O: C, 67.33; H, 6.84; Found: C, 67.43; H, 6.93.

6,6-Dimethyl-9-hydroxy-10-[2(S*)-methyl-3(S*)-hydroxybutyro]-4-propyl -2H,6H-benzo[1,2-b:3,4-b'] dipyran-2-one

[anti-(±)8b]. m.p. 115° C.; $^1$H NMR (CDCl$_3$): 1.05 (3H, t, J=7.3 Hz, CH$_3$), 1.25 (3H, d, J=6.4 Hz, CH$_3$), 1.29 (3H, d, J=6.9 Hz, CH$_3$), 1.54 (6H, s, 2 CH$_3$), 1.66 (2H, apparent sextet, J=7.6 Hz, CH$_2$), 2.92 (2H, t, J=7.8 Hz, CH$_2$), 2.95 (1H, d, J=5.5 Hz, OH), 3.98 (1H, dq, J=6.1 Hz, J=6.8 Hz, H$_2$·), 4.22 (1H, apparent sextet, J=6.2 Hz, H$_3$·), 5.59 (1H, d, J=10.1 Hz, H$_7$), 6.03 (1H, s, H$_3$), 6.73 (1H, d, J=10.1 Hz, H$_8$), 14.25 (1H, s, OH); $^1$H NMR (DMSO-d$_6$): 1.00 (3H, t, J=7.3 Hz, CH$_3$), 1.11 (6H, d, J=6.7 Hz, 2 CH$_3$), 1.49 (3H, s, CH$_3$), 1.60 (2H, apparent sextet, J=7.3 Hz, CH$_2$), 2.85, 2.90 (2H, t-AB type, J=7.7 Hz, J$_{AB}$=21.4 Hz, CH$_2$), 3.59 (1H, apparent quintet, J=7.1 Hz, H$_2$·), 3.96 (1H, apparent quintet, J=7.0 Hz, H$_3$·), 4.97 (1H, broad-s, OH), 5.78 (1H, d, J=10.1 Hz, H$_7$), 6.1 (1H, s, H$_3$), 6.63 (1H, d, J=10.0 Hz, H$_8$), 12.69

(1H, s, OH); MS (EI): 387 (2.8, M+1), 386 (9.4, M+), 371(5.3, M-CH$_3$), 369 (1.5, M—OH), 353 (54.0, M-CH$_3$-H$_2$O), 342 (22.5, M-C$_3$H$_7$-1), 327 (100, M-C$_3$H$_7$-OH+1), UV $\lambda_{max}$ (methanol) nm: 199 (41,000), 270 (25,700), 306 (21,900); IR (KBr) cm$^{-1}$:3478 (broad, m, OH), 1736 (vs) and 1707 (vs) (C=O), 1645 (m), 1603 (vs), 1584 (vs, sh); Anal. Calcd. for C$_{22}$H$_{26}$O$_6$·1/3H$_2$O: C, 67.33; H, 6.84; Found: C, 67.34; H, 6.45.

EXAMPLE 16

Aldol Reaction (Scheme III) of Chromene 4 in the Presence of LDA/TiCl$_4$

In this Example, two procedures are provided for effecting the Aldol reaction. Procedure B was found to be more suitable for scale-up because of simplification of temperature control.

Procedure A. To a stirring solution of chromene 4 (200 mg, 0.58 mmol) in dry methylene chloride (10 mL) at −78° C. under N$_2$ was added 2 M solution of LDA in heptane/TBF/ethyl benzene (0.64 mL, 1.28 mmol). The reaction mixture was stirred at −78° C. for 30 min and then TiC$_4$, (0.13 mL, 1.17 mmol) was added. The resulting yellow solution was warmned to −40° C. and stirred for 45 min. The mixture was recooled to −78° C. , and acetaldehyde (150 mg, 3.5 mmol) was added via syringe. After 4 h, the reaction was quenched by slow addition of pre-cooled saturated NH$_4$Cl (10 mL). Water (3 mL) was added to dissolve the oily solid. The mixture was extracted with ethyl actate (50 mL×3). The combined extracts were washed with brine (100 mL) and dried over MgSO$_4$. The crude product obtained by evaporation was purified by silica gel column chromatography, eluting with hexane/ethyl acetate (5:1) to afford unreacted chromene 4 (30 mg, 15% yield) and syn-(±)-8a (140 mg, 61% yield), which contained 7% of anti-(±)-8b as shown by HPLC.

Procedure B. To a stirring solution of chromene 4 (20 g, 58.4 mmol) in dry methylene chloride (300 mL) at −40° C. under N$_2$ was added TiCl$_4$ (19 mL, 175 mmol). The mixture was then cooled to −78° C. , followed by slow addition of 2 M solution of LDA in heptane/THF/ethyl benzene (64 mL, 128 mmol). After 30 min at the same temperature, acetaldehyde (9 mL, 175 mmol) was added via syringe. The reaction mixture was stirred at −78° C. for 2 h. TLC analysis (hexane/ethyl acetate, 5:1) indicated that approximately 90% chromene 4 had been converted. The mixture was then poured into pre-cooled saturated NH$_4$Cl (240 mL). Water (120 mL) was added to dissolve the oily solid and the mixture was stirred for 20 min. Layers were separated and the aqueous solution was extracted with ethyl acetate (600 mL×3). The combined extracts were washed with brine (600 mL) and dried over MgSO$_4$. Removal of solvents in vacuo afforded a reddish oil (23 g), which was taken up into ether (250 mL). The undissolved residue was filtered and the etheral solution was concentrated to half volume and then slowly added into rapidly stirring hexane cooled at −78° C. Precipitates thus formed were collected by filtration to afford syn-(±)-8a (11.1 g, 49% yield), which contained 4% of (±)8b as shown by HPLC.

EXAMPLE 17

Enzymatic Resolution of syn-(±)-8a (Scheme III)

Into a stirring solution of syn-(±)-8a (7.6 g, 19.7 mmol) in tert-butyl methyl ether (130 mL) at ambient temperature under N$_2$ were added successively vinyl acetate (33 mL), 4 Å molecular sieves (17 g) and Lipase PS-30 (3.8 g) (Amano Enzyme U.S.A. Co., Ltd., Troy, Va.). The resulting mixture was vigorously stirred at ambient temperature for 4 days, whereupon it was filtered through celite and the celite was washed with ethyl acetate (20 mL). The crude product obtained from evaporation was subjected to silica gel column chromatography eluting with a discontinuous gradient of 5%, 10%, 15%, 25%, 30% and 40% of ethyl acetate in hexane to afford 4.8 g (63% yield) of the acetate (9), which was contaminated by over-acylation product of (+)-8a, and 2.8 g (37% yield) of pure syn-(+)-8a.

6,6-Dimethyl-9-hydroxy-10-[2(R)-methyl-3(S)-hydroxybutyro]4-propyl-2H,6H-benzo [1,2-b:3,4-b'] dipyran-2-one

[syn-(+)-8a]. m.p. 82–85° C.; $[\alpha]^{25}_D$=0° (CHCl$_3$, c 0.7; $[\alpha]^{25}_D$=0° (CHCl$_3$, c 0.35); $^1$H NMR (CDCl$_3$): 1.05 (3H, t, J=7.4 Hz, CH$_3$), 1.31 (3H, d, J=5.6 HZ, CH$_3$), 1.33 (3H, d, J=6.9 Hz, CH$_3$), 1.54 (6H, s, 2 CH$_3$), 1.67 (2H, apparent sextet, J=7.6 Hz, CH$_2$), 2.75 (1H, broad-s, OH), 2.91 (2H, t, J=7.8 Hz, CH$_2$), 3.98 (1H, dq, J=2.7 Hz, J=7.0 Hz, H$_2$), 4.30 (1H, dq, J=2.7 Hz, J=6.5 Hz, H$_3$), 5.59 (1H, d, J=10.2 Hz, H$_7$), 6.01 (1H, s, H$_3$), 6.72 (1H, d, J=10.3 Hz, H$_8$), 14.10 (1H, s, OH); $^{13}$C NMR (CDCl$_3$): 10.42 (CH$_3$), 14.00 (CH$_3$), 20.61 (CH$_3$), 23.32 (CH$_2$), 28.31 (2 CH$_3$), 39.05 (CH$_2$), 50.93 (CHCO), 68.03 (CH—O), 79.92 (C—O), 102.95 (C$_{8a}$), 103.69 (C$_4$), 106.12 (C$_{10}$), 110.60 (C$_3$), 115.80 (C$_8$), 126.51 (C$_7$), 157.03 and 157.11 (C$_9$ and C$_{10a}$), 158.58 (C$_{4b}$), 159.01 (C$_4$), 163.13 (CO$_2$), 210.61 (C=O); MS (CI:) 388 (33.4, M+2), 387 (100, M+1), 386 (8.5, M+), 369 (36.3, M-OH), 343 (97.2, M-C$_3$H$_7$); Anal. calcd. for C$_{22}$H$_{26}$O$_6$: C, 68.38; H, 6.78; Found: C, 68.02; H, 6.62.

EXAMPLE 18

10(R),11(R)trans-Dihydro-6,6,1 0,11-tetramethyl4-propyl -2H,6H,12H-benzo-[1,2-b:3,4-b':5,6-b"] tripyran-2,12-dione [Scheme III, (+)-71]

Into a stirring solution of syn-(+)-8a (2.0 g, 5.2 mmol) in THF (50 mL) were added triphenylphosphine (1.9 g, 7.2 mmol) and diethyl azodicarboxylate (DEAD, 1.2 mL, 7.6 mmol). The resulting reddish solution was stirred at ambient temperature under N$_2$ for 5 h, after which the reaction mixture was quenched with saturated aqueous NH$_4$Cl (20 mL) and extracted with ethyl acetate (50 mL×3). The combined extracts were washed with brine (50 mL) and dried over Na$_2$SO$_4$. The crude product (5.8 g) obtained by evaporation was purified by column chromatography on silica gel eluting with a discontinuous gradient of 10%, 20%, 30% and 40% of ethyl acetate in hexane to afford 1.2 g (63% yield) of pure (+)-7. mp 171–175° C.; $[\alpha]^{25}_D$=+37.90° (CHCl$_3$, c 0.73); $^1$H NMR [CDCl$_3$/CD$_3$OD (3:1)]: 1.06 (3H, t, J=7.3 Hz, CH$_3$), 1.22 (3H, d, J=7.0 Hz, CH$_3$), 1.54 (3H, s, CH$_3$), 1.57 (3H, d, J=6.0 Hz, CH$_3$), 1.58 (3H, s, CH$_3$), 1.67 (2H, apparent sextet, J=7.6 Hz, CH$_2$), 2.59 (1H, dq, J=6.9 Hz, J=11.1 Hz, H$_{11}$), 2.92 (2H, t, J=7.8 Hz, CH$_2$), 4.37 (1H, dq, J=6.3 Hz, J=11.1 Hz, H$_{10}$), 5.66 (1H, d, J=10.1 Hz, H$_7$), 6.05 (1H, s, H$_3$), 6.67 (1H, d, J=10.1 Hz, H$_8$); $^{13}$C NMR [CDCl$_3$/CD$_3$OD (3:1)]: δ9.87 (CH$_3$), 13.34 (CH$_3$), 18.97 (CH$_3$), 22.85 (CH$_2$), 27.40 and 27.73 (2 CH$_3$), 38.38 (CH$_2$), 46.82 (CHCO), 79.17 (CH—O and C—O), 102.91 (C$_{8a}$), 104.11 (C$_{4a}$), 105.46 (C$_{12a}$), 111.09 (C$_3$), 115.21 (C$_8$), 126.90 (C$_7$), 154.83 and 155.86 (C$_{8b}$and C$_{12b}$), 157.89 (C$_{4b}$), 158.99 (C$_4$), 160.27 (CO$_2$), 190.50 (C=O); MS (CI): 370 (49.0, M+2), 369 (100, M+1), 368 (17.2, M+); Anal. Calcd. for C$_{22}$H$_{24}$O$_5$: C, 71.72; H, 6.57; Found: C, 71.46; H, 6.60.

(+)-Calanolide A: To a stirring solution of (+)-7 (660 mg, 1.79 mmol) in ethanol (18 mL) were added CeCl$_3$(H$_2$O)$_7$ (2.7 g, 7.17 mmol) and triphenylphosphine oxide (2.0 g, 7.17 mmol). The mixture was stirred for 1 h at ambient temperature under $N_2$ and then cooled to −30° C. with an ethylene glycol/$H_2O$ (1:2 w/w) dry ice bath. After the temperature was equilibrated to −30° C., $NaBH_4$ (271 mg, 7.17 mmol) was added and stirred at the same temperature for 5.5 h, at which time the reaction was quenched with saturated $NH_4Cl$ (20 mL) and extracted with ethyl acetate (30 mL×3). The combined extracts were washed with brine (50 mL) and dried over $Na_2SO_4$. The crude product obtained by removal of solvent under reduced pressure was purified by column chromatography on silica gel eluting with 20% of ethyl acetate in hexane to afford 520 mg (78% yield) of a mixture containing 90% of (+)-calanolide A [(+)-1] and 10% of (+)-calanolide B. (+)-Calanolide A [(+)-1] was further separated from (+)-calanolide B by normal phase HPLC and was identical with an authentic sample.

EXAMPLE 19

Enzymatic Resolution (Scheme IV) of anti-(±)-8b

Into a stirring solution of anti-(±)8b (3.0 g, 7.8 mmol) in tert-butyl methyl ether (78 mL) at ambient temperature under $N_2$ were added successively vinyl acetate (26 mL), 4 Å molecular sieves (3.0 g) and Lipase PS-30 (1.5 g) (Amano Enzyme U.S.A. Co., Ltd., Troy, Va.). The resulting mixture was vigorously stirred at ambient temperature for 41 h, whereupon it was filtered through the celite and the celite was washed with ethyl acetate (20 mL). The crude yellowish solid product (3.2 g) obtained from evaporation was purified by silica gel column chromatography eluting with a discontinuous gradient of 5%, 10%, 15%, 25%, 30% and 40% of ethyl acetate in hexane to afford 1.68 g (50% yield) of the acetate (10) and 1.37 g (46% yield) of anti-(+)-8b. 6,6Dimethyl-9-hydroxy-10-[2(S)-methyl-3(S)-hydroxybutyro]-4-propyl-2H, 6H-benzo -[1,2-b:3,4b'] dipyran-2-one

[anti-(+)-8b]. m.p. 131–134° C.; $[\alpha]^{25}_D$=+45.3° ($CHCl_3$, c 0.72); $^1$H NMR ($CDCl_3$): 1.06 (3H, t, J=7.3 Hz, $CH_3$), 1.25 (3H, d, J=6.6 Hz, $CH_3$), 1.29 (3H, d, J=6.7 Hz, $CH_3$), 1.55 (6H, s, 2 $CH_3$), 1.67 (2H, apparent sextet, J=7.6 Hz, $CH_2$), 2.92 (2H, t, J=7.8 Hz, $CH_2$), 2.96 (1H, d, J=7.1 Hz, OH), 3.98 (1H, apparent quintet, J=6.1 Hz, $H_2$), 4.22 (1H, apparent sextet, J=6.0 Hz, $H_3$), 5.60 (1H, d, J=10.1 Hz, H7), 6.03 (1H, s, $H_3$), 6.73 (1H, d, J=10.1 Hz, $H_8$), 14.25 (1H, s, OH); MS (CI): 388 (41.4, M+2), 387 (100, M+1), 386 (13.0, M$^+$), 369 (42.8, M-OH), 343 (63.8, M-$C_3H_7$); Anal. calcd. for $C_{22}H_{26}O_6$: C, 68.38; H, 6.78; Found: C, 68.50; H, 6.91.

6,6Dimethyl-9-hydroxy-10-[2(R)-methyl-3(R)-acetoxybutyro]4-propyl-2H,6H-benzo -[1,2-b:3,4-b'] dipyran-2-one

[anti-(+)-10]. m.p. 61–64° C.; $[\alpha]^{25}_D$=+30.0 ° ($CHCl_3$, c 0.73); $^1$H NMR ($CDCl_3$): 1.06 (3H, t, J=7.2 Hz, $CH_3$), 1.29 (3H, d, J=6.2 Hz, $CH_3$), 1.32 (3H, d, J=6.7 Hz, $CH_3$), 1.54 (6H, s, 2 $CH_3$), 1.67 (2H, apparent sextet, J=7.6 Hz, $CH_2$), 1.93 (3H, s, $CH_3CO$), 2.91 (2H, m, $CH_2$), 4.18 (1H, dq, J=8.3 Hz, J=6.9 Hz, $H_2$), 5.34 (1H, dq, J=8.2 Hz, J=6.4 Hz, $H_3{'}$), 5.59 (1H, d, J=10.1 Hz, $H_7$), 6.02 (1H, s, $H_3$), 6.73 (1H, d, J=10.1 Hz, $H_8$), 14.02 (1H, s, OH); MS (CI): 430 (37.1, M+2), 429 (95.2, M+1), 428 (7.2, M$^+$), 369 (100, M-AcO); Anal. calcd. for $C_{24}H_{28}O_7$: C, 67.28; H, 6.59; Found: C, 67.75: H, 6.90.

EXAMPLE 20

5,7-Dihydroxy4trifluoromethylcoumarin (Scheme V, 11a, $R_1$=$CF_3$, $R_2$=H)

Into a mixture of anhydrous phloroglucinol (8 g, 63.0 mmol) and ethyl 4,4,4-trifluoroacetoacetate (12 g, 65.0 mmol) was added concentrated $H_2SO_4$ (11 mL). The resulting mixture was heated at 100° C. and stirred for 2h, whereupon the reaction mixture was cooled to room temperature. Ice (100 g) and $H_2O$ (150 mL) were then added while cooling with ice bath. The precipitated product was collected and dissolved in AcOEt (100 mL), which was washed with $H_2O$ and dried over $Na_2SO_4$. The crude product (16 g) obtained by evaporation under vacuum was chromatographed in methylene chloride-ethanol (95:5) to furnish 11a (6 g, 39% yield) along with another unidentified product. 11a: mp 250–252° C. after recrystallization from methylene chloride-hexane. $^1$H NMR (DMSO-$d_6$): 6.30 (1H, s, $H_3$), 6.33 and 6.54 (2H, 2 s, $H_7$ and $H_8$), 10.68 and 10.99 (2H, 2 s, 2 OH); MS (CI) m/z: 246 (100, M$^+$), 226 (14.6, M—HF), 218 (10.0, M-CO), 198 (59.6, M-HF-CO); IR (KBr) cm$^{-1}$: 3537(m, sh) and 3384 (s, broad, OH), 1709 (s, C=O), 1618 (s, C=C—C=O), 1154 (s, C—F); Anal. Calcd. for $C_{10}H_5F_3O_4$: C, 48.80; H, 2.05; Found, C, 48.83; H, 2.10.

EXAMPLE 21

5,7-Dihydroxy-8isobutyryl4-propylcoumarin (Scheme V, 12a, $R_1$=n-Pr, $R_2$=H, $R_3$=$R_4$=Me)

Into a flame-dried 500 mL 3-necked round-bottom flask was placed 5,7-dihydroxy-4-propylcoumarin (2, 10.0 g, 48.1 mmol) and $AlCl_3$ (12.0 g, 90 mmol) under $N_2$. Dichloroethane (120 mL) was then added, and the solution warmed to 75° C. with a water bath with mechanical stirring. After stirring 15 min at 75° C., a homogenous solution was obtained. To this solution was added a mixture of isobutyric anhydride (7.61 g, 48.1 mmol) and $AlCl_3$ (12.0 g) in dichloroethane (60 mL) dropwise over 1 h. After addition was completed, the solution was stirred for an additional 1 h at 75° C., then cooled to room temperature. The solution was poured into a mixture of crushed ice (100 g) and 2 N HCl (100 mL), at which point a white precipitate formed. The mixture was diluted with ethyl acetate (1.8 L), and the organic layer separated. The organic solution was washed sequentially with 1 N HCl (500 mL) and saturated brine (500 mL), dried over magnesium sulfate, filtered and evaporated to provide an orange powder. The powder was triturated with acetone (80 mL), collected on a Büchner funnel, rinsed with diethyl ether (80 mL) and dried to provide a cream colored solid (4.22 g). The product was further purified via recrystallization from ethanol (200 mL) to give colorless plates (3.63 g, 26.0%); mp 263–265° C., with softening at 250° C. (Lit.$^{15}$272–273° C.); $^1$H NMR (DMSO-d6): 0.95 (3H, t, J=7.4 Hz, $CH_3$), 1.08 (6H, d, J=6.9 Hz, 2 $CH_3$), 1.59 (2H, sextet, J=7.4 Hz, $CH_2$), 2.87 (2H, t, J=7.4 Hz, $CH_2$), 3.24 (1H, heptet, J=6.9 Hz, CH), 5.93 (1H, s, $H_3$), 6.37 (1H, s, $H_6$), 11.16 and 11.44 (2H, 2 s, 2 OH); EIMS: 290 (23.2, M$^+$), 247 (100, M-$C_3H_7$), 219 (11.1, M-$C_3H_7CO$); IR (KBr) cm$^{-1}$: 3216 (s, OH), 1684 (s, C=O); Anal. calcd. for $C_{16}H_{18}O_5$: C, 66.20; H, 6.25. Found: C, 66.15; H, 6.21.

EXAMPLE 22

6,6-Dimethyl-9-hydroxy-10-isobutyryl-4propyl-2H, 6H-benzo [1,2-b:3,4-b']dipyran-2-one (Scheme V, 13a, $R_1$=n-Pr, $R_2$=$R_7$=H, $R_3$=$R_4$=$R_5$=Me)

To a solution of 12a (2.90 g, 10.0 mmol) in pyridine (5 mL) was added 4,4-dimnethoxy-2-methylbutan-2-ol (1.49 g, 10.1 mmol), and the solution heated to reflux. After heating for 40 h, TLC indicated complete consumption of starting material. The reaction was cooled to room temperature and the pyridine removed in vacuo. The dark colored residue was dissolved in ethyl acetate (50 mL) and washed sequentially with 2 N HCl (50 mL×2), 5% NaHCO$_3$ (50 mL) and saturated brine (50 mL). The solution was dried over magnesium sulfate, filtered and evaporated to provide a dark orange solid, which was chromatographed on a silica gel column (125 g) and eluted with ethyl acetate/hexane (1:4) to afford the pure product as a bright orange crystalline solid (2.51 g, 70.5%); mp 70–72° C.; $^1$H NMR (CDCl$_3$): 1.05 (3H, t, J=7.3 Hz, CH$_3$), 1.26 (6H, d, J=6.7 Hz, 2 CH$_3$), 1.54 (6H, s, 2 CH$_3$), 1.66 (2H, sextet, J=7.7 Hz, CH$_2$), 2.91 (2H, t, J=7.7 Hz, CH$_2$), 4.06 (1H, heptet, J=6.7 Hz, CH), 5.58 (1H, d, J=9.9 Hz, H$_7$), 6.01 (1H, s, H$_3$), 6.73 (1H, d, J=9.9 Hz, H$_8$), 14.45 (1H, s, OH); EIMS: 356 (48.0, M$^+$), 341 (100, M-CH$_3$), 313 (65.0, M-C$_3$H$_7$); IR (KBr) cm$^{-1}$:1732; Anal. calcd. for C$_{21}$H$_{24}$O$_5$: C, 70.77; H, 6.79. Found: C, 70.73; H, 6.78.

EXAMPLE 23

(±)6,6-Dimethyl-10-(2,2-dimethyl-3-hydroxybutyro)-9-hydroxy-4-propyl-2H,6H-benzo[1,2-b:3,4-b']dipyran-2-one (Scheme V, 14a, R$_1$=n-Pr, R$_2$=R$_7$=R$_8$=H, R$_3$=R$_4$=R$_5$=R$_6$R$_9$=Me)

To a solution of 13a (1.25 g, 3.51 mmol) in anhydrous THF (20 mL) under N$_2$ at −78° C. was added LDA (2.0 M in heptane/THF/ethyl benzene, 4.39 mL, 8.78 mmol) dropwise, and the resulting red solution stirred for 1 h. A solution of acetaldehyde (1.54 g, 35.1 mmol) in THF (6 mL) was added dropwise, and the reaction mixture stirred at −78° C. for 3 hours whereupon the reaction was quenched by slowly adding 2.5 M ethanolic HCl (10 mL), and the solution then allowed to warm to room temperature. The solvent was evaporated in vacuo and the residue partitioned between ethyl acetate (100 mL) and saturated NaHCO$_3$ (100 mL). The organic layer was collected and washed with saturated brine (100 mL), dried over magnesium sulfate, filtered and evaporated to provide a brown solid. The product was triturated with ethyl acetate/hexane (1:1, 15 mL), collected on a Büchner funnel, rinsed with fresh solvent and air dried to give the desired product as a white powder (654 mg, 46.6%). An analytical sample was obtained via recrystallization from ethyl acetate/hexane (1:1); mp 190–191° C. ; $^1$H NMR (CDCl$_3$): 1.04 (3H, t, J=7.4 Hz, CH$_3$), 1.25 (3H, s, CH$_3$), 1.29 (3H, d, J=6.4 Hz, CH$_3$), 1.33 (3H, s, CH$_3$), 1.48 (3H, s, CH$_3$), 1.52 (3H, s, CH$_3$), 1.66 (2H, sextet, J=7.5 Hz, CH$_2$), 2.39 (1H, broad-s, OH), 2.88 (m, 2H, CH$_2$), 4.47 (1H, q, J=6.4 Hz, CH), 5.56 (1H, d, J=10.0 Hz, H$_7$), 5.92 (1H, s, H$_3$), 6.64 (1H, d, J=10.0 Hz, H$_8$), 8.99 (1H, s, OH): EIMS: 400 (1.1, M$^+$), 356 (37.5, M—C$_2$H$_4$O), 341 (100, M-CH$_3$—C$_2$H$_4$O), 313 (68.2, M-C$_3$H$_7$—C$_2$H$_4$O); IR (KBr) cm$^{-1}$:3246 (broad-s, OH), 1686 (s, C=O); Anal. calcd. for C$_{23}$H$_{28}$O$_6$: C, 68.98; H, 7.05. Found. C, 69.03; H, 6.99.

EXAMPLE 24

(±)-6.6-Dimethyl-10-(2,3-dimethyl-3-hydroxybutyro)-9-hydroxy-4-propyl-2H,6H-benzo[1,2-b:3,4-b']dipyran-2-one (Scheme V, 14b, R$_1$=n-Pr, R$_2$=R$_3$=R$_7$=H, R$_4$=R$_5$=R$_6$=R$_8$=R$_9$=Me)

To a suspension of 4 (1.2 g, 3.50 mmol) in THF (16 mL) at −78° C. was added a solution of LDA in heptane/THF/ethyl benzene (2 M, 5.0 mL, 10.0 mmol) dropwise under N$_2$. The solution was stirred at −78° C. for 1 h and acetone (2.0 mL, 27.2 mmol) was added quickly via syringe. The solution was stirred at −78° C. for 3 h, quenched with methanolic HCl (2 M, 15 mL) at −78° C. , then allowed to warm to room temperature. The reaction mixture was concentrated and partitioned between ethyl acetate (150 mL) and saturated NaHCO$_3$ (100 mL). The organic layer was collected and washed with saturated brine (50 mL), dried over magnesium sulfate, filtered and concentrated to provide a red oil (1.36 g), an analytical sample of which was obtained via silica gel column chromatography (ethyl acetate/hexane, 1:4) as an off-white solid: mp 99–102° C.; $^1$H NMR (CDCl$_3$): 1.05 (3H, t, J=7.3 Hz, CH$_3$), 1.29 (3H, s, CH$_3$), 1.32 (3H, s, CH$_3$), 1.39 (3H, d, J=6.8 Hz, CH$_3$), 1.55 (6H, s, 2 CH$_3$), 1.67 (2H, sextet, J=7.7 Hz, CH$_2$), 2.91 (2H, t, J=7.7 Hz, CH$_2$), 3.52 (1H, broad-s, OH), 4.03 (1H, q, J=6.8 Hz, CH), 5.60 (1H, d, J=9.9 Hz, H$_7$), 6.03 (1H, s, H$_3$), 6.73 (1H, d, J=10.1 Hz, H$_8$), 13.81 (1H, s, OH); EIMS: 401 (5.1, M+1), 400 (21.5, M$^+$), 385 (6.2, M-CH$_3$), 342 (38.9, M-C$_3$H$_7$O+1), 327 (100, M-CH$_3$—C$_3$H$_7$O+1); IR (KBr) cm$^{-1}$:3547 (w, OH), 3449 (vw, broad, OH), 1734 (vs, C=O); Anal. calcd. for C$_{23}$H$_{28}$O$_6$: C, 68.98; H, 7.04. Found: C, 68.98; H, 7.04.

EXAMPLE 25

(±)-syn and (±)and-6,6-Dimethyl-9-hydroxy-10-(2-methyl-3-hydroxypentanoyl)-4-propyl-2H,6H-benzo[1,2-b :3,4-b']dipyran-2-one (Scheme V, 14c, R$^1$=n-Pr, R$_2$=R$_3$=R$_7$=R$_8$=H, R$_4$=R$_5$=R$_6$=Me, R$_9$=Et)

To a solution of 4 (1.75 g, 5.11 mmol) in THF (27.0 mL) at −78° C. was added dropwise a solution of LDA in heptane/THF/ethyl benzene (2 M, 7.0 mL, 14.0 mmol) under N$_2$. The solution was stirred at −78° C. for 1 h, and propionaldehyde (2.2 mL, 31.2 mmol) was added quickly via syringe. The solution was stirred at −78° C. for 3 h, quenched with methanolic HCl (2 M, 25 mL) at −78° C., then warmed to room temperature. The mixture was extracted with ethyl acetate (350 mL), washed sequentially with 150 mL each of saturated NaHCO$_3$ and saturated brine, dried over magnesium sulfate, filtered and concentrated to provide a diastereomeric mixture of the product as a red oil (2.44 g, 100%), which was not further purified and used for the next step.

EXAMPLE 26

(±)-10,11-Dihydro-6,6,10,11,11-pentamethyl4-propyl-2H,6H, 12H-benzo[1,2-b:3,4-b':5,6-b"]tripyran-2,12-dione (Scheme V, 15a, R$_1$=n-Pr, R$_2$=R$_7$=R$_8$=H, R$_3$=R$_4$=R$_5$=R$_6$=R$_9$=Me)

To a solution of 14a (0.5 g, 1.25 mmol) and triphenylphosphine (492 mg, 1.88 mmol) in THF (10 mL) was added a solution of diethyl azodicarboxylate (327 mg, 1.88 mmol) in THF (2 mL) dropwise under N$_2$. The reaction mixture was stirred for 2.5 h, after which it was poured into saturated NH$_4$Cl (100 mL). The solution was extracted with ethyl acetate (100 mL), and the separated organic layer washed sequentially with H$_2$O (100 mL) and saturated brine (100 mL). After drying over magnesium sulfate, the solution was filtered and concentrated in vacuo to provide a yellow oil. Column chromatography through 75 g silica gel (ethyl acetate/hexane, 1:2) provided the desired product as a white crystalline solid (449 mg, 94.0%). An analytical sample was obtained via recrystallization from ethyl acetate/hexane (2:1): mp 157° C.; $^1$H NMR (CDCl$_3$): 1.03 (3H, t, J=7.3 Hz, CH$_3$), 1.09 (3H, s, CH$_3$), 1.19 (3H, s, CH$_3$), 1.43 (3H, d, J=6.5 Hz, CH$_3$), 1.53 (3H, s, CH$_3$), 1.55 (3H, s, CH$_3$), 1.64 (2H, sextet, J=7.7 Hz, CH$_2$), 2.88 (2H, t, J=7.7 Hz, CH$_2$), 4.34 (1H, q, J=6.4 Hz, H$_{10}$), 5.60 (1H, d, J=10.0 Hz, H$_7$), 6.04 (1H, s, H$_3$), 6.66 (1H, d, J=10.0 Hz, H$_8$); EIMS: 382

(60.8, M·), 367 (100, M-CH$_3$), 312 (50.3 (M-C$_5$H$_{10}$), 297 (74.5, M-CH$_3$—C$_5$H$_{10}$); IR (KBr) cm$^{-1}$:1730 (vs, C=O); Anal. calcd. for C$_{23}$H$_{26}$O$_5$: C, 72.23; H, 6.85. Found: C, 72.35; H, 6.90.

EXAMPLE 27

(±)-10,11-Dihydro-6,6,10,10,11-pentamethyl4-propyl-2H, 6H, 12H-benzo[1,2-b:3,4-b':5,6-b"]tripyran-2,12-dione (Scheme V, 15b, R$_1$= n-Pr, R$_2$=R$_3$=R$_7$=H, R$_4$=R$_5$=R$_6$=R$_8$=R$_9$=Me)

To a solution of crude 14b (980 mg, 2.19 mmol) and triphenylphosphine (859.0 mg, 3.28 mmol) in THF (15 mL) was slowly added diethyl azodicarboxylate (DEAD, 0.50 mL, 3.17 mmol) under N$_2$. The red solution was stirred for 2.5 h at room temperature, then quenched with saturated NH$_4$Cl (10 mL). The solution was extracted with ethyl acetate (200 mL), washed sequentially with 50 mL each of H$_2$O and saturated brine, dried over magnesium sulfate, filtered and concentrated to provide a yellow residue (2.37 g). Purification by silica gel column chromatography (ethyl acetate/hexane, 1:10) provided, after overnight drying under high vacuum in the presence of P$_2$O$_5$, the desired product as an off-white solid (373.7 mg, 44.6%): mp 140–141° C.; $^1$H NMR (CDCl$_3$): 1.03 (3H, t, J=7.3 Hz, CH$_3$), 1.19 (3H, d, J=7.0 Hz, CH$_3$), 1.34 (3H, s, CH$_3$), 1.53 (6H, s, 2 CH$_3$), 1.55 (3H, s, CH$_3$), 1.65 (2H, sextet, J=7.8 Hz, CH$_2$), 2.72 (1H, q, J=7.0 Hz, H$_{11}$), 2.85–2.91 (2H, m, CH$_2$), 5.60 (1H, d, J=10.1 Hz, H$_7$), 6.03 (1H, s, H$_3$), 6.65 (1H, d, J=10.0 Hz, H$_8$); EIMS: 382 (61.2, M$^+$), 367 (82.0, M-CH$_3$), 312 (46.0, M-C$_5$H$_{10}$), 297 (100, M-CH$_3$-C$_5$H$_{10}$); IR (KBr) cm$^{-1}$:1728 (vs, C=O); Anal. calcd. for C$_{23}$H$_{26}$O$_5$: C, 72.23; H, 6.85. Found: C, 71.95; H, 6.88.

EXAMPLE 28

(±)-10,11-trans-10,11-Dihydro-10-ethyl-4-propyl-6,6,11-trimethyl-2H, 6H, 12H-benzo[1,2-b:3,4-b"]tripyran-2,12-dione (15c) and (±)-10,11-cis-10,11-dihydro-10-ethyl4 -propyl-6,6, 11-trimethyl-2H, 6H, 12H-benzo[1,2-b:3,4b':5,6-b"] tripyran-2,12-dione (15d, Scheme V)

To a solution of 14c (2.44 g, 5.11 mmol) and triphenylphosphine (1.96 mg, 7.48 mmol) in THF (30.0 mL) was slowly added diethyl azodicarboxylate (DEAD, 1.16 mL, 7.37 mmol) under N$_2$. The red solution was stirred for 2.5 h at room temperature, then quenched with saturated NH$_4$Cl (22 mL). The solution was warmed to room temperature and extracted with ethyl acetate (400 mL), washed with H$_2$O (100 mL) and brine (100 mL) and dried over magnesium sulfate. After filtration, the solution was concentrated in vacuo to provide a yellow residue (5.75 g). The crude product was purified by repetitive silica gel column chromatography (3×) using ethyl acetate/hexane (1:4.5) as eluent. The desired fractions were combined, concentrated in vacuo and dried under high vacuum overnight in the presence of P$_2$O$_5$ to afford 15c (765.4 mg, 39.2%) and 15d (350.4 mg, 17.9%).

15c (R$^1$=n-Pr, R$_2$=R4=R$_7$=R$_8$=H, R$_3$=R$_5$=R$_6$=Me, R$_9$ =Et): mp 155–158° C.; $^1$H NMR (CDCl$_3$): 1.03 (3H, t, J=7.4 Hz, CH$_3$), 1.13 (3H, t, J=7.4 Hz, CH$_3$), 1.22 (3H, d, J=6.9 Hz, CH$_3$), 1.53 (3H, s, CH$_3$), 1.56 (3H, s, CH$_3$), 1.64 (2H, sextet, J=7.6 Hz, CH$_2$), 1.78–1.95 (2H, m, CH$_2$), 2.62 (1H, dq, J=10.4 Hz, J=7.0 Hz, H$_{11}$), 2.88 (2H, t, J=7.7 Hz, CH$_2$), 4.14 (1H, ddd, J=3.5 Hz, J=7.8 Hz, J=10.7 Hz, H$_{10}$), 5.61 (1H, d, J=10.0 Hz, H$_7$), 6.04 (1H, s, H$_3$), 6.66 (1H, d, J=10.0 Hz, H$_8$); EIMS: 382 (37.2, M$^+$), 367 (100, M-CH$_3$), 297 (47.2, M-CH$_3$-C$_5$H$_{10}$); IR (KBr) cm$^{-1}$:1738 (vs, C=O); Anal. calcd. for C$_{23}$H$_{26}$O$_5$: C, 72.23; H, 6.85. Found: C, 71.75; H, 7.02.

15d (R$_1$=n-Pr, R$_2$=R$_3$=R$_7$=R$_8$=H, R$_4$=R$_5$=R$_6$=Me, R$_9$=Et): mp 100–102° C.; $^1$H NMR (CDCl$_3$): 1.03 (3H, t, J=7.3 Hz, CH$_3$), 1.07 (3H, t, J=7.4 Hz, CH$_3$), 1.14 (3H, d, J=7.3 Hz, CH$_3$), 1.54 (3H, s, CH$_3$), 1.55 (3H, CH$_3$), 1.65 (2H, sextet, J=7.6 Hz, CH$_2$), 1.83–1.98 (2H, m, CH$_2$), 2.70 (1H, dq, J=3.2 Hz, J=7.3 Hz, H$_{11}$), 2.88 (2H, t, J=7.6 Hz, CH$_2$),4.39 (1H, ddd, J=3.4 Hz, J=5.3 Hz, J=8.8 Hz, H$_{10}$), 5.60 (1H, d, J=10.0 Hz, H$_7$), 6.05 (1H, s, H$_3$), 6.66 (1H, d, J=10.0 Hz, H$_8$); EIMS: 382 (55.0, M$^+$), 367 (100, M-CH$_3$), 297 (52.7, M-CH$_3$—C$_5$H$_{10}$); IR (KBr) cm$^{-1}$:1732 (vs, C=O); Anal. calcd. for C$_{23}$H$_{26}$O$_5$: C, 72.23; H, 6.85. Found: C, 71.80; H, 6.97.

EXAMPLE 29

(±)-10,12-cis-10,11-Dihydro-12-hydroxy-6,6,10,11,11-pentamethyl-4propyl-2H, 6H, 12H-benzo[1,2-b:3,4-b':5,6-b"]tripyran-2-one (16a) and (±)-10,12-trans-10,11-dihydro -12-hydroxy-6,6, 10,11,11-pentamethyl14propyl-2H,6H,12H -benzo[1,2-b:3,4-b':5,6-b"]tripyran-2-one (16b, Scheme V)

To a solution of 15a (252 mg, 0.661 mmol) in ethanol/THF (1:1, 8 mL) was added sodium borohydride (25.1 mg, 0.661 mmol) and the solution stirred at room temperature for 30 minutes. The reaction was quenched by the addition of water (1 mL), and the solvent then removed in vacuo. The residue was partitioned between 20 mL each of ethyl acetate and 1 M HCl, and the organic phase separated and washed sequentially with 5% NaHCO$_3$ and saturated brine. After drying over magnesium sulfate, the solution was evaporated to give the product as a pale-yellow foam. TLC analysis (ethyl acetate/hexane, 1:2) showed the two epimeric alcohols 16a and 16b at R$_f$ 0.30 and 0.25, as well as a minor impurity at R$_f$ 0.55. Separation via column chromatography (75 g silica gel, ethyl acetate/hexane, 1:2) provided 16a (127.7 mg, 50.3%) and 16b (18.8 mg, 7.4%) as a white foam and an off-white waxy solid, drespectively.

16a (R$_1$=n-Pr, R$_2$=R$_7$=R$_8$=H, R$_3$=R$_4$=R$_5$=R$_6$=R$_9$=Me): $^1$H NMR (CDCl$_3$): 1.04 (3H, t, J=7.3 Hz, CH$_3$), 1.06 (6H, s, 2 CH$_3$), 1.40 (3H, d, J=6.7 Hz, CH$_3$), 1.47 (3H, s, CH$_3$), 1.50 (3H, s, CH$_3$), 1.66 (2H, sextet, J=7.3 Hz, CH$_2$), 2.80–2.99 (2H, m, CH$_2$), 3.39 (1H, d, J=3.2 Hz, OH), 3.99 (1H, q, J=6.7 Hz, H$_{10}$), 4.70 (1H, d, J=3.2 Hz, H$_{12}$), 5.54 (1H, d, J=9.9 Hz, H$_7$), 5.94 (1H, s, H$_3$), 6.63 (1H, d, J=9.9 Hz, H$_8$); EIMS: 384 (59.0, M$^+$), 369 (100, M-CH$_3$), 314 (44.7, M-C$_5$H$_{10}$), 299 (88.8, M-CH$_3$C$_5$H$_{10}$); IR (KBr) cm$^{-1}$:3432 (broad-s, OH), 1734 (vs, C=O); Anal. calcd. for C$_{23}$H$_{28}$O$_5$: C, 71.85; H, 7.34. Found: C, 71.74; H, 7.43.

16b (R$_1$=n-Pr, R$_2$=R$_7$=R$_8$=H, R$_3$=R$_4$=R$_5$=R$_6$=R$_9$=Me): $^1$H NMR (CDCl$_3$): 0.78 (3H, s, CH$_3$), 1.04 (3H, t, J=7.3 Hz, CH$_3$), 1.11 (3H, s, CH$_3$), 1.36 (3H, d, J=6.5 Hz, CH$_3$), 1.49 (6H, s, 2 CH$_3$), 1.64 (2H, m, CH$_2$), 2.47 (1H, broad-s, OH), 2.89 (2H, m, CH$_2$), 4.35 (1H, q, J=6.5 Hz, H$_{10}$), 4.63 (1H, broad-s, H$_{12}$), 5.54 (1H, d, J=9.8 Hz, H$_7$), 5.96 (1H, s, H$_3$), 6.65 (1H, d, J=9.8 Hz, H$_8$); EIMS: 384 (40.7, M$^+$), 369 (100, M-CH$_3$), 314 (13.5, M-C$_5$H$_{10}$), 299 (48.4, M-CH$_3$—C$_5$H$_{10}$); Anal. calcd. for C$_{23}$H$_{28}$O$_5$: C, 71.85; H, 7.34. Found: C, 71.79; H, 7.49.

EXAMPLE 30

(±)-11,12-cis-10,11-Dihydro-12-hydroxy-6,6,10,10,11-pentamethyl-4-propyl-2H, 6H, 12H-benzo[1,2-b:3,4-b':5,6-b"]tripyran-2-one (16c) and (±)-11,12-trans-10,11-dihydro -12-hydroxy-6,6, 10,10,11-pentamethyl4-propyl-2H,6H,12H -benzo[1, 2-b:3,4-b':5,6-b"]tripyran-2-one (16d, Scheme V)

To a solution of 15b (289.7 mg, 0.75 mmol), triphenylphosphine oxide (927.0 mg, 3.33 mmol) and CeCl$_3$ ($H_2O$)$_7$ (842.0 mg, 2.25 mmol) in ethanol (15 mL) at 0° C. was slowly added $NaBH_4$ (195.0 mg, 5.15 mmol) under $N_2$. The suspension was stirred for 1 h at room temperature, then quenched with saturated $NH_4Cl$ (30 mL). The solution was extracted with ethyl acetate (200 mL), washed with brine (50 mL), dried over magnesium sulfate, filtered and concentrated to afford a pink crystalline solid (1.38 g). Silica gel column chromatography (ethyl acetate/hexane, 1:5) provided 16c (100.0 mg, 34.3%) as off-white foam and 16d which was further purified by preparative TLC (silica gel, diethyl ether/hexane, 2:1) as off-white foam (56.0 mg, 19.2%).

16c ($R_1$=n-Pr, $R_2$=$R_3$=$R_7$=H, $R_4$=$R_4$=$R_6$=$R_8$=$R_9$=Me): mp 44–45° C.; $^1$H NMR (CHCl$_3$): 1.04 (3H, t, J=7.3 Hz, CH$_3$), 1.24 (3H, d, J=7.1 Hz, CH$_3$), 1.38 (3H, s, CH$_3$), 1.45 (3H, s, CH$_3$), 1.47 (3H, s, CH$_3$), 1.51 (3H, s, CH$_3$), 1.66 (2H, sextet, J=7.3 Hz, CH$_2$), 1.96–2.04 (1H, m, H$_{11}$), 2.8–3.0 (2H, m, CH$_2$), 3.02 (1H, d, J=4.0 Hz, OH), 4.94 (1H, t, J=4.2 Hz, H$_{12}$), 5.53 (1H, d, J=10.0 Hz, H$_7$), 5.94 (1H, s, H$_3$), 6.65 (1H, d, J=9.9 Hz, H$_8$); EIMS: 385 (22.1, M+1), 384 (61.8, M$^+$), 369 (71.1, M-CH$_3$), 351 (29.5, M-CH$_3$-H$_2$O), 299 (100, M-CH$_3$-C$_5$H$_{10}$); IR (KBr) cm$^{-1}$:3451 (broad-m, OH), 1709 (s, C=O); Anal. calcd. for C$_{23}$H$_{28}$O$_5$: C, 71.85; H, 7.33. Found: C, 71.63; H, 7.64.

16d ($R_1$=n-Pr, $R_2$=$R_4$=$R_7$=H, $R_3$=$R_5$=$R_6$=$R_8$=$R_9$=Me): mp 40–42° C.; $^1$H NMR (CDCl$_3$): 1.04 (3H, t, J=7.3 Hz, CH$_3$), 1.13 (3H, d, J=7.0 Hz, CH$_3$), 1.21 (3H, s, CH$_3$), 1.46 (3H, s, CH$_3$), 1.48 (3H, s, CH$_3$), 1.52 (3H, s, CH$_3$), 1.67 (2H, sextet, J=7.6 Hz, CH$_2$), 2.03 (1H, quintet, J=7.2 Hz, H$_{11}$), 2.8–3.0 (2H, m, CH$_2$), 3.66 (1H, s, OH), 4.69 (1H, d, J=7.4 Hz, H$_{12}$), 5.54 (1H, d, J=10.0 Hz, H$_7$), 5.94 (1H, s, H$_3$), 6.63 (1H, d, J=9.9 Hz, H$_8$); EIMS: 385 (8.7, M+1), 384 (36.0, M$^+$), 369 (65.8, M-CH$_3$), 351 (17.6, M-CH$_3$-H$_2$O), 299 (100, M-CH$_3$-C$_5$H$_{10}$); IR (KBr) cm$^{-1}$:3437 (w, OH), 1734 (s, C=O); Anal. calcd. for C$_{23}$H$_{28}$O$_5$: C, 71.85; H, 7.33. Found: C, 71.70; H, 7.56.

EXAMPLE 31

(±)-10,11-trans-11,12-cis-10,11-Dihydro-10-ethyl-12-hydroxy4-propyl-6,6,11-trimethyl-2H,6H,12H-benzo[1,2-b:3,4-b':5,6-b"]tripyran-2-one (16e) and (±)-10,11-trans -11,12-trans-10,11-dihydro-10-ethyl-12-hydroxy-4-propyl -6,6,11-trimethyl-2H,6H,12H-benzo[1,2-b:3,4-b':5,6-b"] tripyran-2-one (16f, Scheme V)

To a suspension of 15c (454.7 mg, 1.19 mmol), triphenylphosphine oxide (1.38 g, 4.96 mmol) and CeCl$_3$(H$_2$O)$_7$ (1.21 g, 3.25 mmol) in ethanol (10 mL) at 0° C. was slowly added NaBH$_4$ (312.0 mg, 8.25 mmol) under N$_2$. The suspension was stirred for 3 h at room temperature. The reaction mixture was quenched with saturated NH$_4$Cl (15 mL), extracted with ethyl acetate (100 mL×3), washed with brine (50 mL), dried over magnesium sulfate, filtered and concentrated to provide pink crystals (1.97 g). Silica gel column chromatography (ethyl acetate/hexane, 1:4) afforded a yellow oil, which consisted of mixture of 16e and 16f (261.0 mg). The compounds were separated using preparative HPLC (normal phase, ethyl acetate/hexane, 3:7). The desired fractions were combined and concentrated in vacuo and dried overnight under high vacuum in the presence of P$_2$O$_5$ to afford 16e (yellow oil, 46.5 mg, 10.1%) and 16f (white solid, 137.6 mg, 30.1%).

16e ($R_1$=n-Pr, $R_2$=$R_4$=$R_7$=$R_8$=H, $R_3$=$R_5$=$R_6$=Me, $R_9$=Et): $^1$H NMR (CDCl$_3$): 1.03 (3H, t, J=7.3 Hz, CH$_3$), 1.10 (3H, t, J=7.6 Hz, CH$_3$). 1.13 (3H, d, J=6.8 Hz, CH$_3$), 1.48 (3H, s, CH$_3$), 1.49 (3H, s, CH$_3$), 1.65 (2H, sextet, J=7.4 Hz, CH$_2$), 1.76–1.98 (3H, m, CH$_2$+H$_{11}$), 2.80–2.92 (3H, m, CH$_2$+OH), 4.10 (1H, ddd, J=2.9 Hz, J=7.9 Hz, J=10.7 Hz, H$_{10}$), 4.98 (1H, d, J=3.3 Hz, H$_{12}$), 5.54 (1H, d, J=9.9 Hz, H$_7$), 5.94 (1H, s, H$_3$), 6.63 (1H, d, J=9.9 Hz, H$_8$); EIMS: 385(10.5, M+1), 384 (35.8,M$^+$), 369 (78.4, M-CH$_3$), 366 (43.1, M—H$_2$O), 351 (39.0, M-CH$_3$-H$_2$O), 337 (100, M-H$_2$O-C$_2$H$_5$), 299 (37.7, M-CH$_3$-C$_5$H$_{10}$); IR (neat, thin film) cm$^{-1}$:3432 (w, OH), 1709 (s, C=O); Anal. calcd. for C$_{23}$H$_{28}$O$_5$.1/4H$_2$O: C, 71.02; H, 7.38. Found: C, 71.10; H, 7.40.

16f ($R_1$=n-Pr, $R_2$=$R_4$=$R_7$=$R_8$=H, $R_3$=$R_5$=$R_6$=Me, $R_9$=Et): mp 103–105° C.; $^1$H NMR (CDCl$_3$): 1.04 (3H, t, J=7.3 Hz, CH$_3$), 1.07 (3H, t, J=7.4 Hz, CH$_3$), 1.13 (3H, d, J=6.9 Hz, CH$_3$), 1.47 (3H, s, CH$_3$), 1.51 (3H, s, CH$_3$), 1.66 (2H, sextet, J=7.6 Hz, CH$_2$), 1.79–1.90 (2H, m, CH$_2$), 2.05 (1H, m, H$_{11}$), 2.90 (2H, m, CH$_2$), 3.53 (1H, s, OH), 3.78 (1H, dt, J=4.1 Hz, J=8.1 Hz, H$_{10}$), 4.73 (1H, d, J=6.7 Hz, H$_{12}$),5.54 (1H, d, J=10.0 Hz, H$_7$), 5.95 (1H, s, H$_3$), 6.63 (1H, d, J=9.9 Hz, H$_8$); EIMS: 385 (7.6, M+1), 384 (31.1, M$^{+1}$), 369 (100, M-CH$_3$), 351 (9.5, M-CH$_3$-H$_2$O), 337 (11.5, M-H$_2$O-C$_2$H$_5$), 299 (36.9, M-CH$_3$-C$_5$H$_{10}$); IR (KBr) cm$^{-1}$:3493, 3435 and 3250 (w, OH), 1699 (s, C=O); Anal. calcd. for C$_{23}$H$_{28}$O$_5$: C, 71.85; H, 7.33. Found: C, 71.46; H, 7.34.

EXAMPLE 32

(±)-10,11-cis-11,12-trans-10,11-Dihydro-10-ethyl-12-hydroxy-4-propyl-6,6,11-trimethyl-2H,6H,12H-benzo[1,2-b:3,4-b':5,6-b"] tripyran-2-one (16g) and (±)-10,11,12-cis-10,11-dihydro-10-ethyl-12-hydroxy-4-propyl-6,6,11-trimethyl-2H,6H, 12H-benzo[1,2-b:3,4-b':5,6-b"]tripyran-2-one (16h, Scheme V)

To a solution of 15d (290.5 mg,0.76 mmol) in ethanol (15 mL) at 25° C. was added NaBH$_4$ (269.0 mg, 7.11 mmol) portionwise under N$_2$. The suspension was stirred for 1 h at room temperature, then quenched with saturated NH$_4$Cl (6 mL). The solution was extracted with ethyl acetate (200 mL), washed with brine (80 mL), dried over magnesium sulfate, filtered and concentrated to provide a pink residue (455.8 mg). The crude product was purified by silica gel preparative TLC (ethyl acetate/hexane, 2:1). The desired bands were scraped, combined, extracted, concentrated in vacuo and dried under high vacuum overnight in the presence of P$_2$O$_5$ to afford the desired products 16g (229 mg, 78% yield) with 95% purity as indicated by HPLC) and 16h (55.9 mg, 19% yield) with 92% purity. The analytical samples were obtained by further purification via preparative HPLC (normal phase, ethyl acetate/hexane, 3:7).

16g ($R_1$=n-Pr, $R_2$=$R_3$=$R_7$=$R_8$=H, $R_4$=$R_5$=$R_6$=Me, $R_9$=Et): $^1$H NMR (CDCl$_3$): 1.03 (3H, t, J=7.4 Hz, CH$_3$), 1.04 (3H, t, J=7.3 Hz, CH$_3$),1.12 (3H, d, J=7.1 Hz, CH$_3$), 1.49 (3H, s, CH$_3$), 1.66 (2H, sextet, J=7.3 Hz, CH$_2$), 1.8–2.0 (2H, m, CH$_2$), 2.3–2.4 (1H, m, H$_{11}$), 2.8–3.0 (2H, m, CH$_2$), 3.30 (1H, s, OH), 4.06 (1H, dt, J=10.1 Hz, J=3.3 Hz, H$_{10}$), 5.10 (1H, d, J=5.2 Hz, H$_{12}$), 5.55 (1H, d, J=10.0 Hz, H$_7$), 5.94 (1H, s, H$_3$), 6.63 (1H, d, J=10.0 Hz, H$_8$); EIMS: 385 (6.3, M+1), 384 (27.3, M$^+$), 369 (100, M-CH$_3$), 351 (6.8, M-CH$_3$-H$_2$O), 337 (4.2, M-H$_2$O-C$_2$H$_5$), 299 (34.7, M-CH$_3$-C$_5$H$_{10}$); IR (KBr) cm$^{-1}$;3449 (m, OH), 1734 (vs, C=O); Anal. calcd. for C$_{23}$H$_{28}$O$_5$: C, 71.85; H, 7.33. Found: C, 71.79; H, 7.39.

16h ($R_1$=n-Pr, $R_2$=$R_3$=$R_7$=$R_8$=H, $R_4$=$R_5$=$R_6$=Me, $R_9$=Et): $^1$H NMR (CDCl$_3$): 0.79 (3H, d, J=7.3 Hz, CH$_3$), 1.04 (3H, t, J=7.3 Hz, CH$_3$), 1.11 (3H, t, J=7.3 Hz, CH$_3$), 1.49 (3H, s, CH$_3$), 1.51 (3H, s, CH$_3$), 1.67 (2H, sextet, J=7.4 Hz, CH$_2$), 1.92 (2H, m, CH$_2$), 2.10 (1H, tq, J=2.0 Hz, J=7.3 Hz, H$_{11}$), 2.79 (1H, s, OH), 2.81–2.90 (2H, m, CH$_2$), 4.23 (1H, ddd, J=1.9 Hz, J=5.4 Hz, J=8.7 Hz, H$_{10}$), 4.87 (1H, d, J=1.9 Hz, H$_{12}$), 5.54 (1H, d, J=10.0 Hz, H$_7$), 5.96 (1H, s, H$_3$), 6.66 (1H, d, J=9.9 Hz, H$_8$); EIMS: 385 (6.1, M+1), 384 (26.0, M$^+$), 369 (100, M-CH$_3$), 351 (9.8, M-CH$_3$-H$_2$O), 337 (8.2, M-H$_2$O-C$_2$H$_5$), 299 (17.6, M-CH$_3$-C$_5$H$_{10}$); IR (neat, thin film) cm$^{-1}$: 3410 (w, OH), 1732 (s, C=O).

EXAMPLE 33

(±)-10,11-trans-4-Propyl-7,8,10,11-tetrahydro-6,6,10,11-tetramethyl-2H,6H,12H-benzo[1,2-b:3,4-b':5,6-b"]tripyran-2,12-dione (Scheme VI, 18a, R$_1$=n-Pr, R$_2$=R$_4$=R$_7$=R$_8$=H, R$_3$=R$_5$=R$_6$=R$_9$=Me)

To a solution of (±)-7 (534 mg, 1.45 mmol) in ethanol/methylene chloride (1:1, 50 mL, Parr apparatus) under N$_2$ was added 10% palladium/carbon (53.4 mg) at ambient temperature. The mixture was shaken under hydrogen (2 atm) for 1 h, then gravity filtered through Whatmann filter paper. The solvent was evaporated to give a white crystalline solid which was filtered through a short plug of silica gel, eluting with methylene chloride/methanol (97:3). The pure compound (±)-18a (441 mg, 82.2%) was obtained as white plates by recrystallization from ethyl acetate: mp 165° C.; $^1$H NMR (CDCl$_3$): 1.01 (3H, t, J=7.3 Hz, CH$_3$), 1.21 (3H, d, J=6.8 Hz, CH$_3$), 1.42 (3H, s, CH$_3$), 1.44 (3H, s, CH$_3$), 1.53 (3H, d, J=6.2 Hz, CH$_3$), 1.61 (2H, sextet, J=7.5 Hz, CH$_2$), 1.84 (2H, apparent dt, J=2.4 Hz, J=6.7 Hz, CH$_2$), 2.53 (1H, dq, J=11.2 Hz, J=6.8 Hz, H$_{11}$), 2.69 (2H, apparent dt, J=3.4 Hz, J=6.7 Hz, CH$_2$), 2.88 (2H, t, J=7.5 Hz, CH$_2$), 4.28 (1H, dq, J=11.2 Hz, J=6.2 Hz, H$_{10}$), 6.02 (1H, s, H$_3$); EIMS: 371 (40.8, M+1); 370 (100, M$^+$), 314 (99.3, M-C$_4$H$_8$), 299 (21.6, M-C$_5$H$_{10}$-1), 286 (65.0, M-CH$_3$-C$_5$H$_{10}$+1), 271 (20.5, M-CH$_3$13 C$_5$H$_8$O), 259 (47.5, M-C$_4$H$_8$-C$_3$H$_4$O+1); IR (KBr) cm$^{-1}$; 1740 (vs, C=O); Anal. calcd. for C$_{22}$H$_{26}$O$_5$: C, 71.33; H, 7.07. Found: C, 71.00; H, 7.22.

EXAMPLE 34

(±)-10,11-trans-10,11-DihydroApropyl-6,6,10,11-tetramethyl-2H, 6H, 12H-benzo[1,2-b:3,4-b':5,6-b"]tripyran-2,12-dione-12-oxime (Scheme VI, 19a, R$_1$=n-Pr, R$_2$=R$_4$=R$_7$=R$_8$=H, R$_3$=R$_5$=R$_6$=R$_9$=Me, R$_{10}$=H)

Into a 100 mL one-necked round-bottom flask was placed (±)-7 (1.47 g, 4.00 mmol) and NH$_2$OHHCl (1.39 g, 20.0 mmol). To this mixture was added methanol (60 mL), and the solution heated to reflux with magnetic stirring until the ketone dissolved. Solid K$_2$CO$_3$ powder (1.38 g, 10.0 mmol) was then carefully added, and the reaction allowed to stir at reflux for 4 hours. The solution was cooled at room temperature, filtered to remove the K$_2$CO$_3$ and evaporated in vacuo, to provide a yellow solid. The residue was partitioned between 150 mL each of H$_2$O and ethyl acetate. The organic phase was collected and washed sequentially with 1 N HCl and saturated brine, then dried over magnesium sulfate, filtered and evaporated to afford a thick yellow syrup, which was purified via silica gel column chromatography (75 g), eluting with methylene chloride/methanol (97:3) to afford the desired product as a white solid (657 mg, 43%). An analytical sample was obtained via recrystallization from acetone/hexane (1:3) as colorless prisms; mp 200–201° C. ; $^1$H NMR (CDCl$_3$): 1.04 (3H, t, J=7.4 Hz, CH$_3$), 1.23 (3H, d, J=7.0 Hz, CH$_3$), 1.33 (3H, d, J=6.5 Hz, Ch$_3$), 1.51 (3H, s, CH$_3$), 1.54 (3H, s, CH$_3$), 1.67 (2H, sextet, J=7.4 Hz, CH$_2$), 2.83–3.01 (2H, m, CH$_2$), 3.79 (1H, dq, J=2.0 Hz, J=7.0 Hz, H$_{11}$), 4.46 (1H, dq, J=2.0 Hz, J=6.5 Hz, H$_{10}$), 5.57 (1H, d, J=9.9 Hz, H$_7$), 6.02 (1H, s, H$_3$), 6.67 (1H, d, J=9.9 Hz, H$_8$). 9.46 (1H, broad-s, OH); EIMS: 384 (12.9,M+1), 383 (49.22, M$^+$), 368 (100, M-CH$_3$), 366 (21.1, M-OH), 352 (15.2, M-NOH); IR (KBr) cm$^{-1}$: 3223 (broad, OH), 1740 (C=O); Anal. calcd. for C$_{22}$H$_{25}$NO$_5$.1/4H$_2$O): C, 68.11; H, 6.63; N, 3.61. Found: C, 68.40; H, 6.59; N,3.58.

EXAMPLE 35

(±)-10,11-trans-10,11-Dihydro-4-propyl-6,6,10,11-tetramethyl-2H, 6H, 12H-benzo[1,2-b:3,4-b':5,6 -b"]tripyran-2,12-dione-12-methoxime (Scheme VI, 19b, R$_1$=n-Pr, R$_2$=R$_4$=R$_7$=R$_8$=H, R$_3$=R$_5$=R$_6$=R$_9$=Me, R$_{10}$=Me)

Into a one-necked 100 mL round-bottom flask was placed (±)-7 (1.47 g, 4.00 mmol) and NH$_2$OCH$_3$HCl (1.67 g, 20.0 mmol). To this mixture was added methanol (60 mL), and the solution heated to reflux with magnetic stirring until the ketone dissolved. Solid K$_2$CO$_3$ powder (1.38 g, 10.0 mmol) was then carefully added, and the reaction allowed to stir at reflux for 4 hours. The solution was cooled to room temperature, filtered to remove the K$_2$CO$_3$ and evaporated in vacuo, to provide a yellow oil. The residue was partitioned between 150 mL H$_2$O and 150 mL ethyl acetate. The organic phase was collected and washed sequentially with 1 N HCl and saturated brine, then dried over magnesium sulfate, filtered and evaporated to afford a thick yellow syrup. The product was purified via silica gel column chromatography (75 g), eluting with ethyl acetate/hexane (1:3) to afford the desired product as a faintly yellow oil which, upon standing, formed a white solid (598 mg, 38%). An analytical sample was obtained via recrystallization from acetone/hexane (1:3) as white plates; mp 143–144° C.; $^1$H NMR (CDCl$_3$): 1.01 (3H, t, J=7.3 Hz, CH$_3$), 1.16 (3H, d, J=7.0 Hz, CH$_3$), 1.28 (3H, d, J=6.4 Hz, CH$_3$), 1.49 (3H, s, CH$_3$), 1.50 (3H, s, CH$_3$), 1.64 (2H, sextet, J=7.3 Hz, CH$_2$), 2.79–2.99 (2H, m, CH$_2$), 3.57 (H, dq, J=1.9 Hz, J=7.0 Hz, H$_{11}$), 4.06 (3H, s, OCH$_3$), 4.37 (1H, dq, J=1.9 Hz, J=6.4 Hz, H$_{10}$), 5.54 ($_{H, d,}$ $_{J=}$10.0 Hz, H$_7$), 6.00 (1H, s, H$_3$), 6.62 (1H, d, J=10.0 Hz, H$_8$); EIMS: 397 (61.2, M$^+$), 382 (100, M-CH$_3$), 366 (12.9, M-OCH$_3$); IR (KBr) cm$^{-1}$: 1728 (vs, C=O); Anal. calcd. for C$_{23}$H$_{27}$NO$_5$: C, 69.50; H, 6.85; N, 3.52. Found: C, 69.39; H, 6.90; N, 3.59.

EXAMPLE 36

Conversion of (−)-Calanolide A into (−)-Calanolide B

To a solution of (−)-calanolide A (341 mg, 0.922 mmol) in anhydrous methylene chloride (5 mL) at −78° C. under N$_2$ was added a solution of diethylamidosulfur trifluoride (DAST, 178 mg, 1.11 mmol) in methylene chloride (1 mL) and the resulting yellow solution stirred at −78° C. for 4 hours. The reaction was quenched with 0.5 mL methanol, then allowed to warm to room temperature. The solution was diluted with methylene chloride (20 mL), then washed with water (50 mL) and saturated brine (50 mL). After drying over magnesium sulfate, the solution was filtered and evaporated to provide a light yellow solid. TLC analysis (silica gel, 3% methanol in methylene chloride) showed two components, one fast-moving and one slow. The material was chromatographed through 80 g silica gel, eluting with 1% methanol in CH$_2$Cl$_2$, and the fractions containing the respective components combined and evaporated to afford 198 mg (61% yield) of compound 22 and 75.3 mg (22%) of (−)-calanolide B.

10(S)4-propyl-6,6,10,11-tetramethyl-2H,6H,10H-benzo[1,2-b:3,4-b':5,6b"]tripyran-2-one (22): $^1$H NMR (CDCl$_3$): 1.03 (3H, t, J=7.4 Hz, CH$_3$), 1.39 (3H, d, J=6.6 Hz, CH$_3$), 1.47 (3H, s, CH$_3$). 1.51 (3H, s, CH$_3$), 1.66 (2H, sextet, J=7.4 Hz CH$_2$), 1.85 (3H, s, CH$_3$), 2.88 (2H, m, CH$_2$), 4.89 (1H, q, J=6.6 Hz, H$_{10}$), 5.55 (1H, d, J=10.0 Hz, H$_7$), 5.93 (1H, s, H$_3$), 6.62 (1H, d, J=10.0 Hz, H$_8$), 6.64 (1H, s, H$_{12}$); EIMS: 353 (15.5, M+1), 352 (53.2, M$^+$), 337 (100, M-CH$_3$). IR (KBr) cm$^{-1}$:1724 (s, C=O); Anal. calcd. for $C_{22}H_{24}O_4$: C, 74.98; H, 6.86. Found: C, 74.87; H, 7.00.

(−)-Calanolide B: $^1$H NMR (CDCl$_3$): 1.03 (3H, t, J=7.3 Hz, CH$_3$), 1.14 (3H, d, J=7.0 Hz, CH$_3$), 1.43 (3H, d, J=6.4 Hz, CH$_3$), 1.48 (3H, s, CH$_3$), 1.49 (3H, CH$_3$), 1.66)2H, sextet, J=7.6 Hz, CH$_2$), 1.72–1.79 (1H, m, H$_{11}$), 2.60 (1H, d, J=3.8 Hz, OH), 2.89 (2H, m, CH$_2$), 4.26 (1H, dq, J=10.7 Hz, 6.3 Hz, H$_{10}$), 4.97 (1H, J=3.8 Hz, H$_{12}$5.53 (1H, d, J=10.0 Hz, H$_7$), 5.95 (1H, s, H$_3$), 6.63 (1H, d, J=10.0 Hz, H$_8$); EIMS: 370 (31.1, M$^+$), 355 (100, M-CH$_3$), 299 (29.7, M-CH$_3$-C$_4$H$_8$); IR (KBr) cm$^{-1}$:3478 (s, sharp, OH), 1703 (s, C=O).

EXAMPLE 37

In Vitro evaluation of (+)-, (±)- and (−)-calanolide A

Figure 1B:
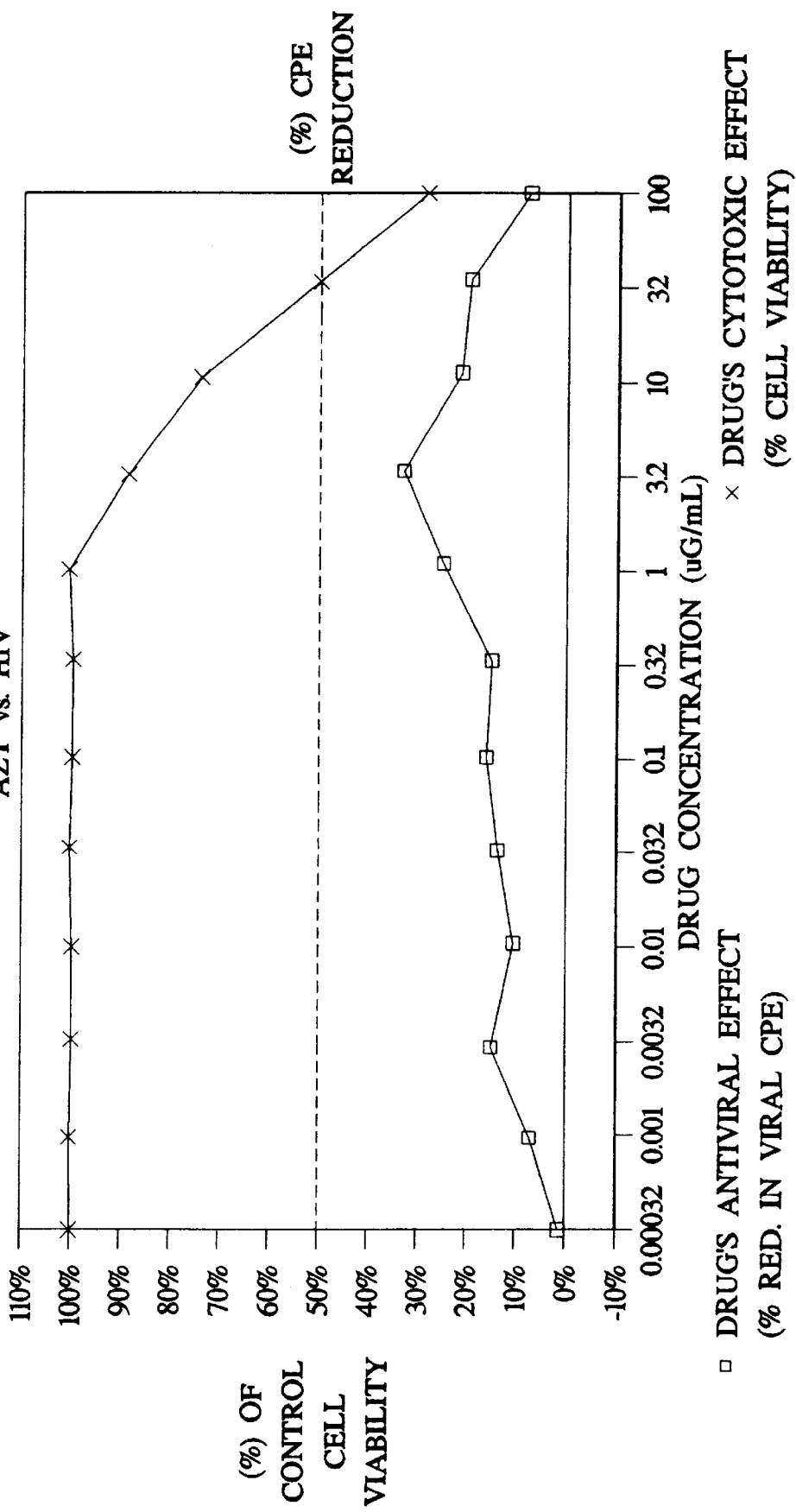
Figure 1C:
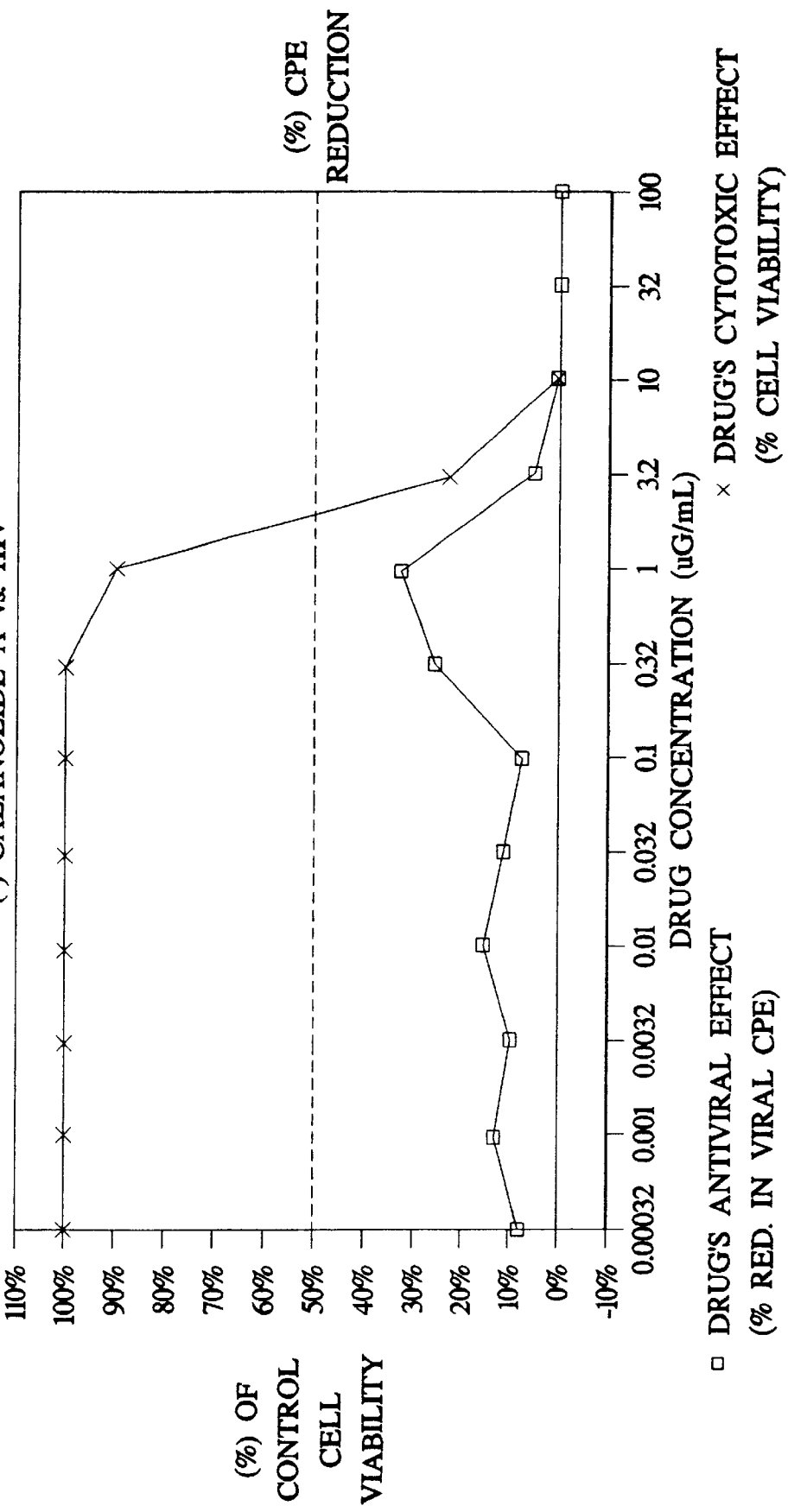
Figure 1D:
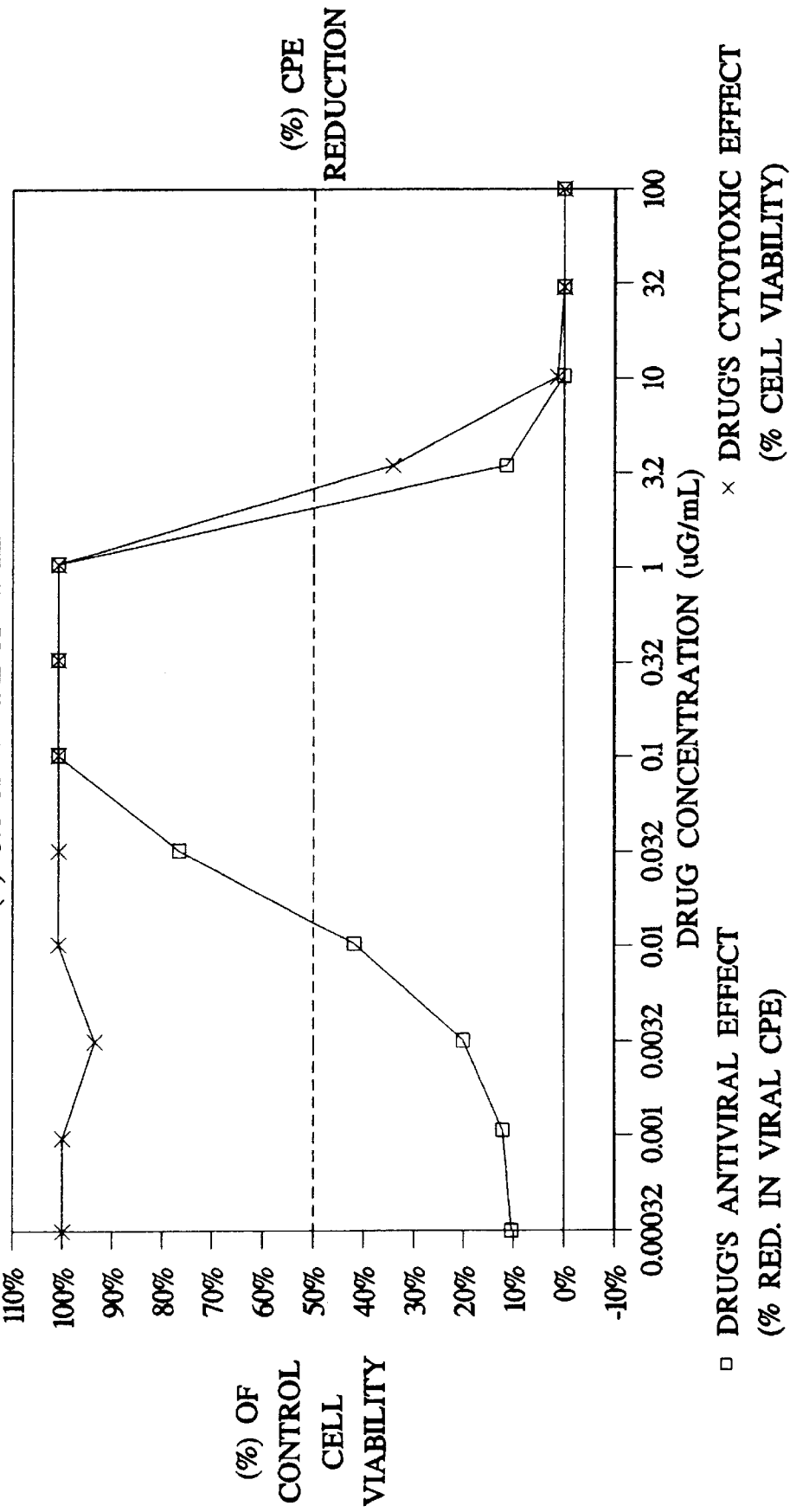
Figure 1E:
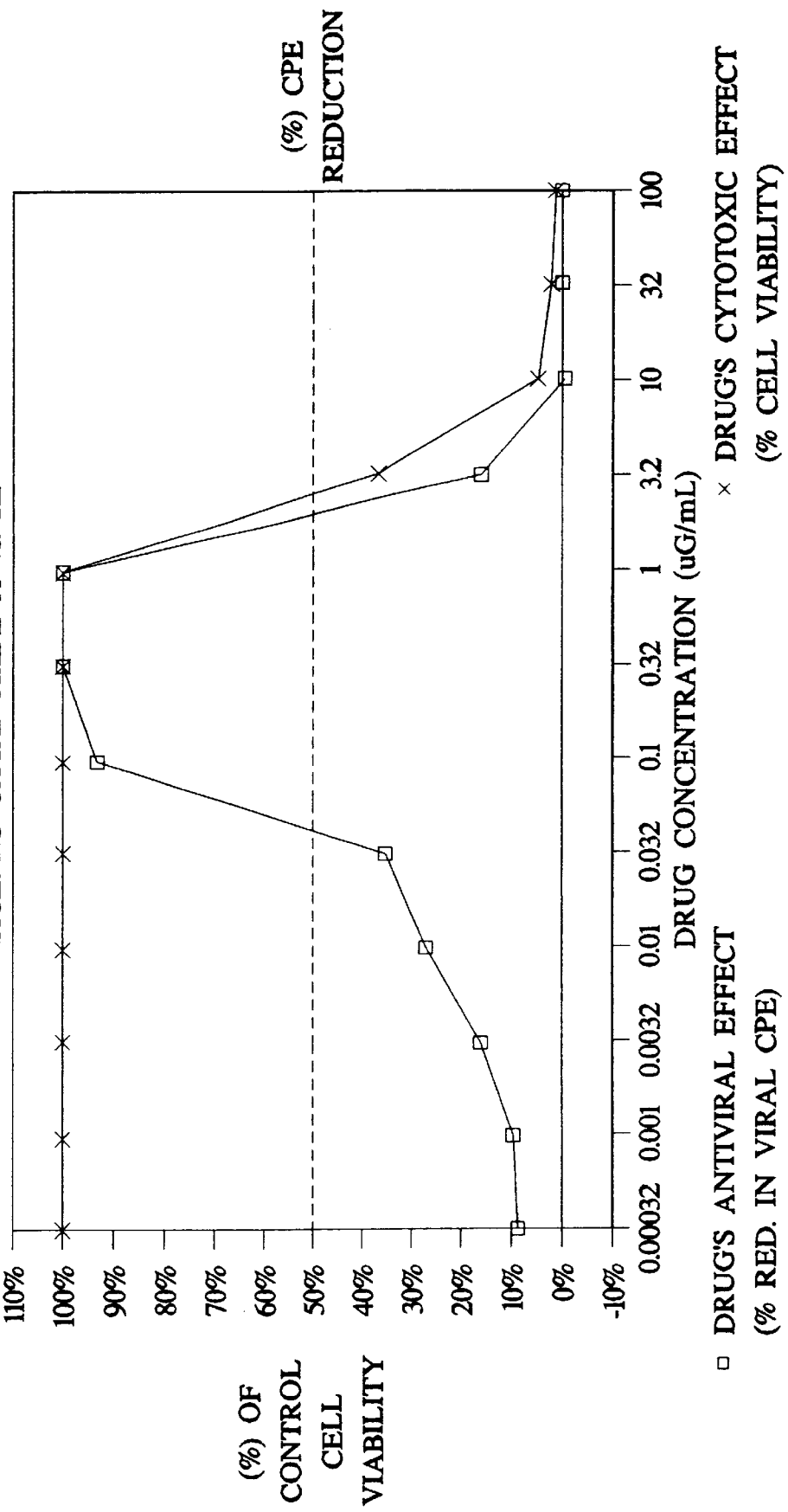

This example illustrates the anti-HIV viral activity of the synthetic (±)-calanolide A and its pure enantiomers, (+)-calanolide A and (−)-calanolide A, which were evaluated using the published MTT-etrazolium method[18]. Retroviral agents AZT and DDC were used as controls for comparison purposes. The cells used for screening were the MT-2 and the human T4-lymphoblastoid cell line, CEM-SS, and were grown in RPMI 1640 medium supplemented with 10% fetal (v/v) heat-inactivated fetal calf serum and also containing 100 units/mL penicillin, 100 µg/mL streptomycin, 25 mM HEPES and 20 µg/mL gentamicin. The medium used for dilution of drugs and maintenance of cultures during the assay was the same as above. The HTLV-IIIB and HTLV-RF were propagated in CEM-SS. The appropriate amounts of the pure compounds for anti-HIV evaluations were dissolved in DMSO, then diluted in medium to the desired initial concentration. The concentrations (µg drug/mL medium) employed were 0.0032 µg/mL; 0.001 µg/mL; 0.0032 µg/mL; 0.01 µg/mL; 0.032 µg/mL; 0.1 µg/mL; 0.32 µg/mL; 1 µg/mL; 3.2 µg/mL; 10 µg/mL; 32 µg/mL; and 100 µg/mL. Each dilution was added to plates in the amount of 100 µL/well. Drugs were tested in triplicate wells per dilution with infected cells while in duplicate wells per dilution with uninfected cells for evaluation of cytotoxicity. On day 6 (CEM-SS cells) and day 7 (MT-2 cells) post-infection, the viable cells were measured with a tetrazolium salt, MTT (5 mg/mL), added to the test plates. A solution of 20% SDS in 0.001 N HCl is used to dissolve the MTT formazan produced. The optical density value was a function of the amount of formazan produced which was proportional to the number of viable cells. The percent inhibition of CPE per drug concentration was measured as a test over control and expressed in percent (T/C%). The data is summarized in FIGS. 1 (a–e), 2 (a–e), 3 (a–e), 4 (a–d), and 5 (a–d).

FIGS. 1(a) to 1(e) illustrate in vitro MTT assay results using an isolate, G910-6 HIV viral strain[19], which is AZT-resistant. The data shows that (−)-calanolide A was relatively non-toxic at concentrations of 1 µg/mL but exhibited very little antiviral effect. Moreover, (±)-calanolide A and (+)-calanolide A were effective in reducing viral CPE. As expected, AZT had little to no effect in reducing viral CPE and enhancing cell viability.

Figure 2A:
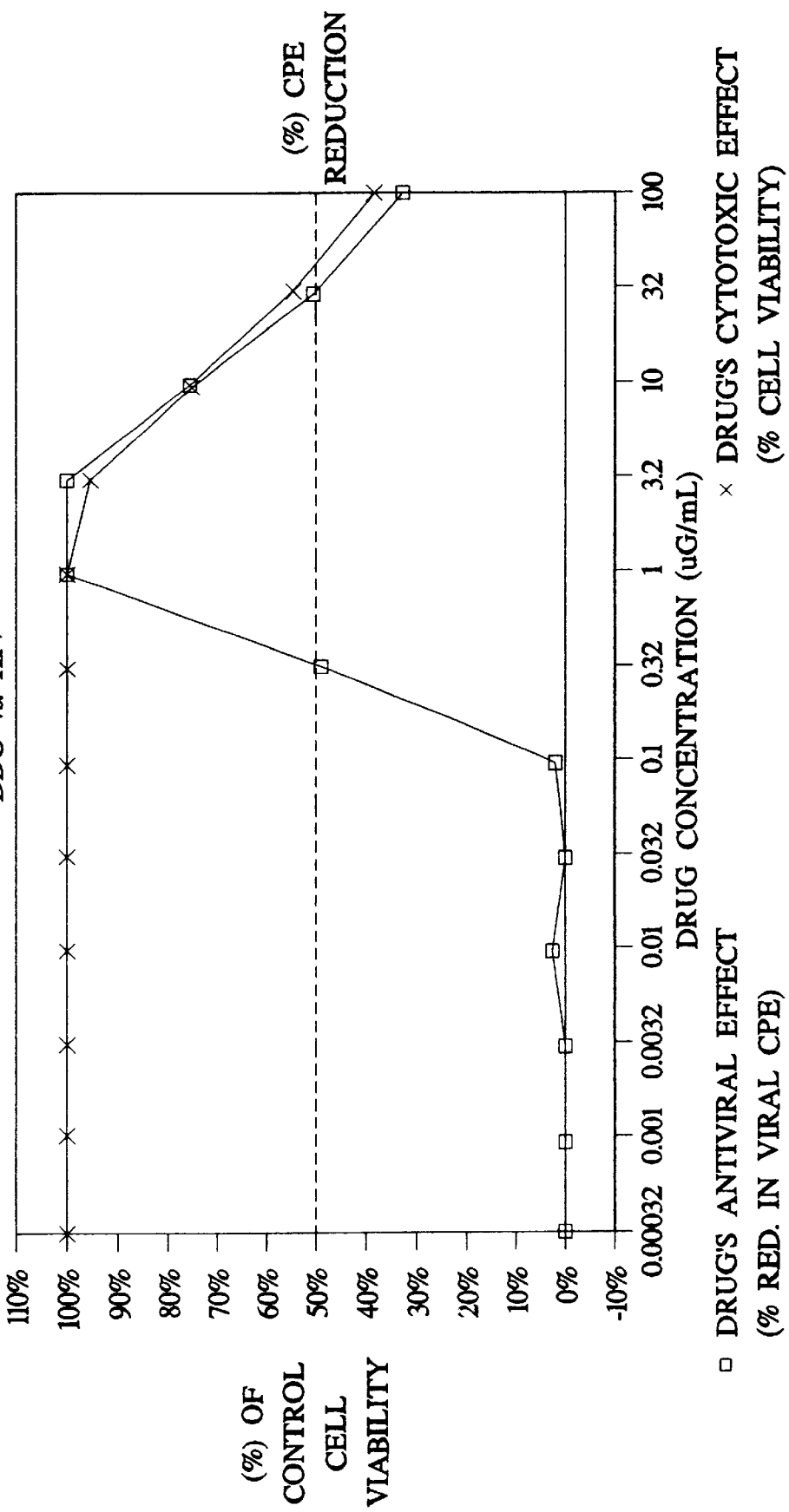
FIGS. 2(a) to 2(e) illustrate in vitro MTT assay results, as described in Example 37, using H112-2 HIV viral strain which was not pre-treated with AZT.
Figure 2B:
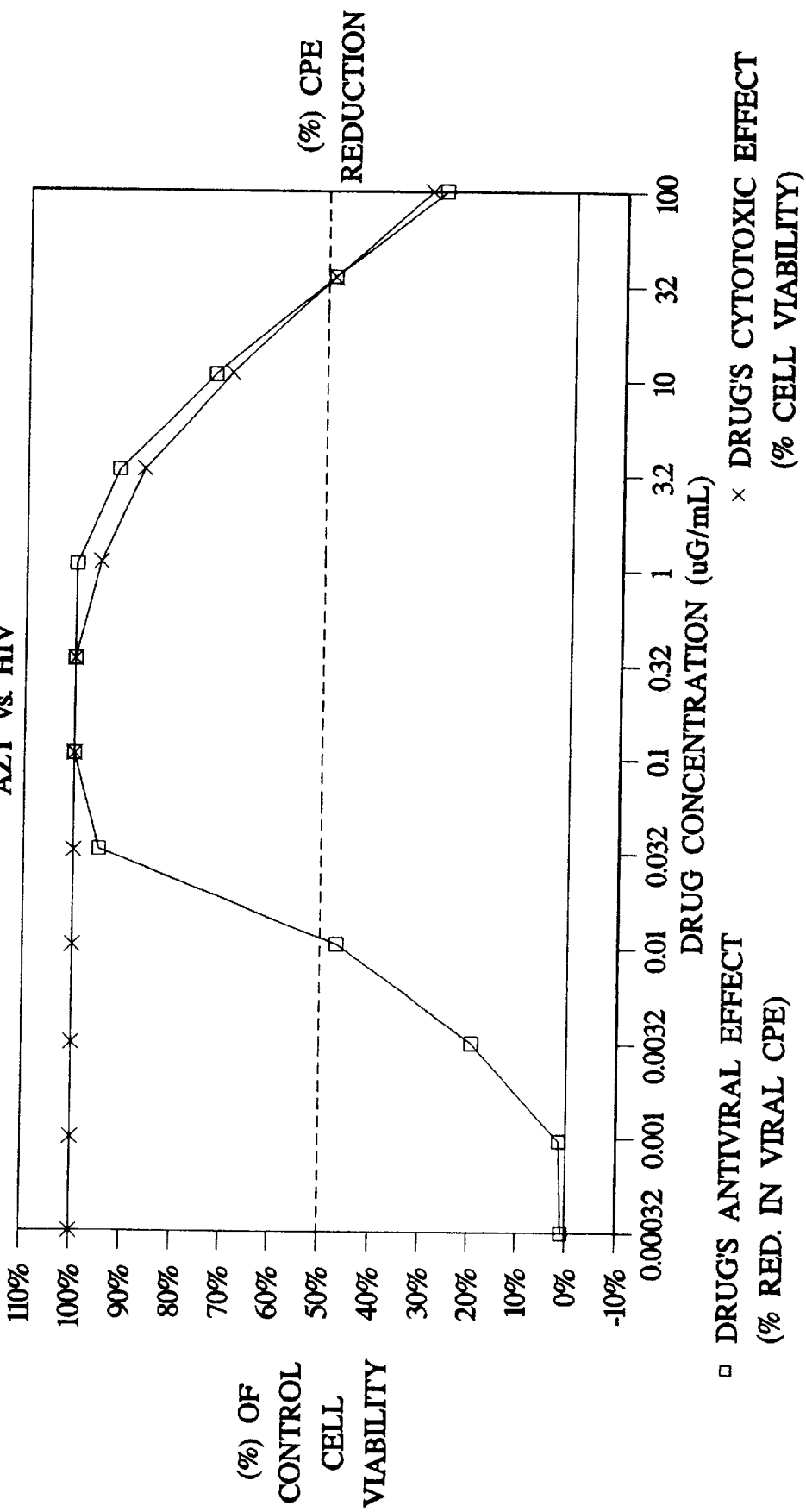
Figure 2C:
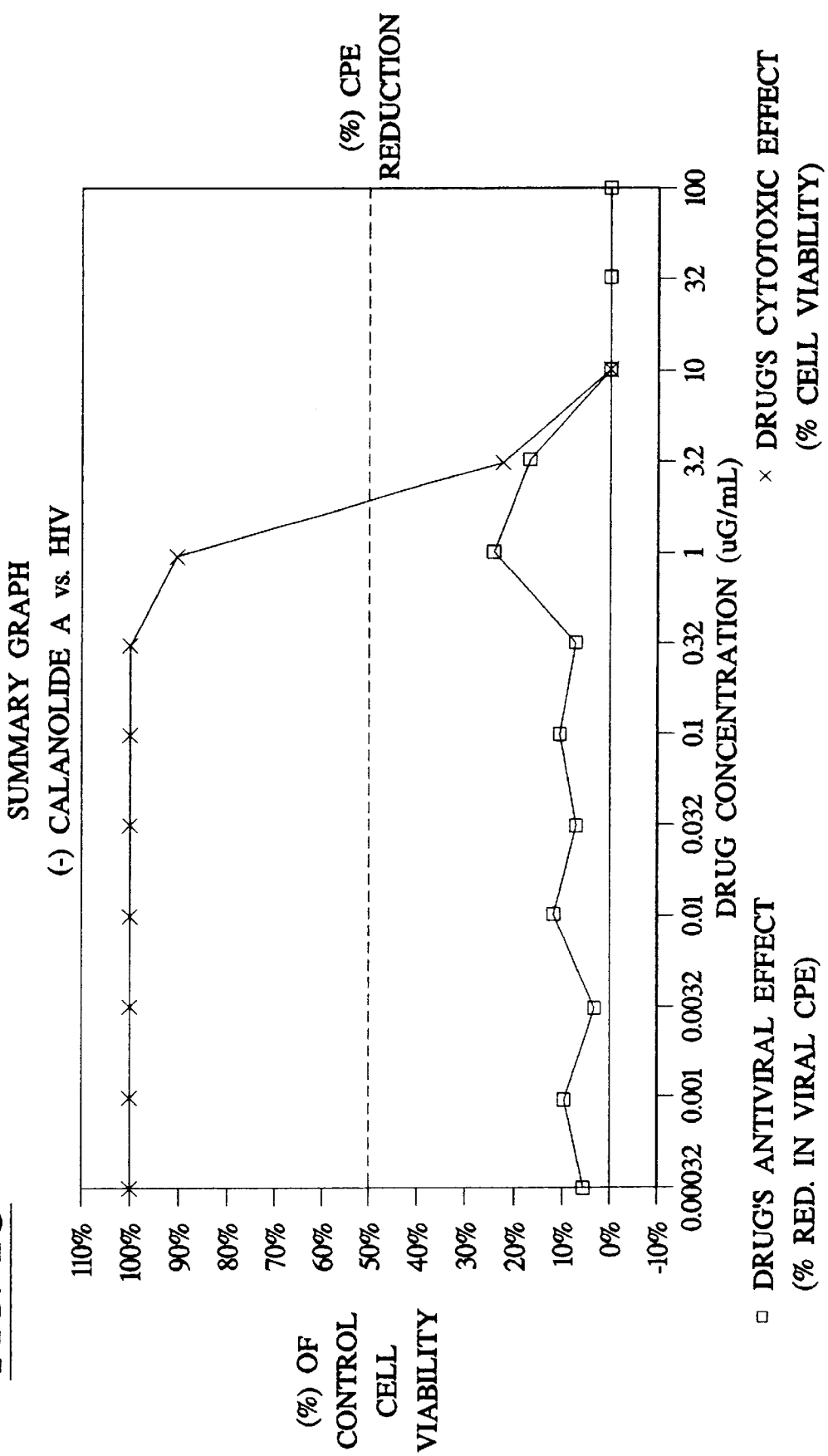
Figure 2D:
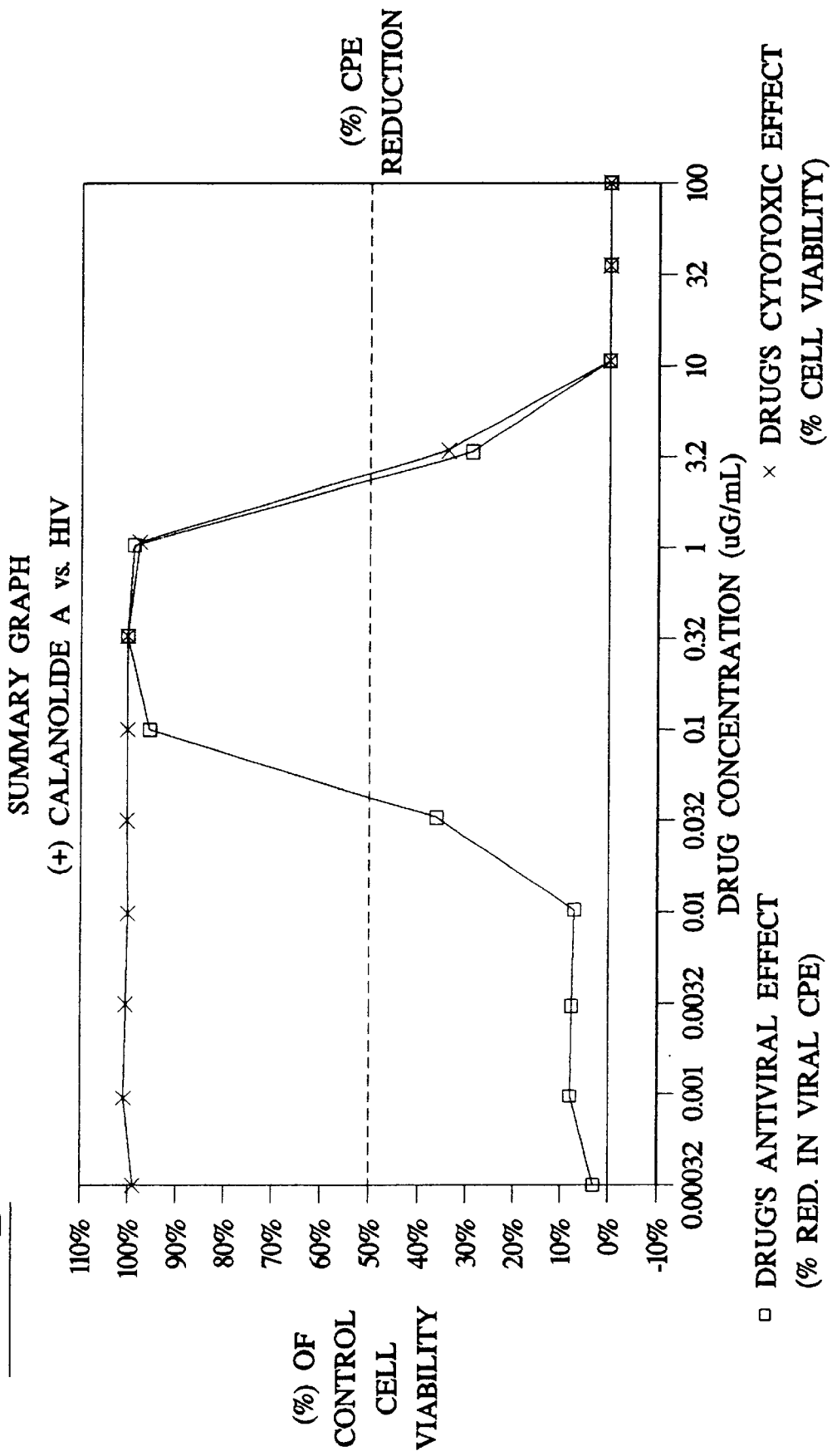
Figure 2E:
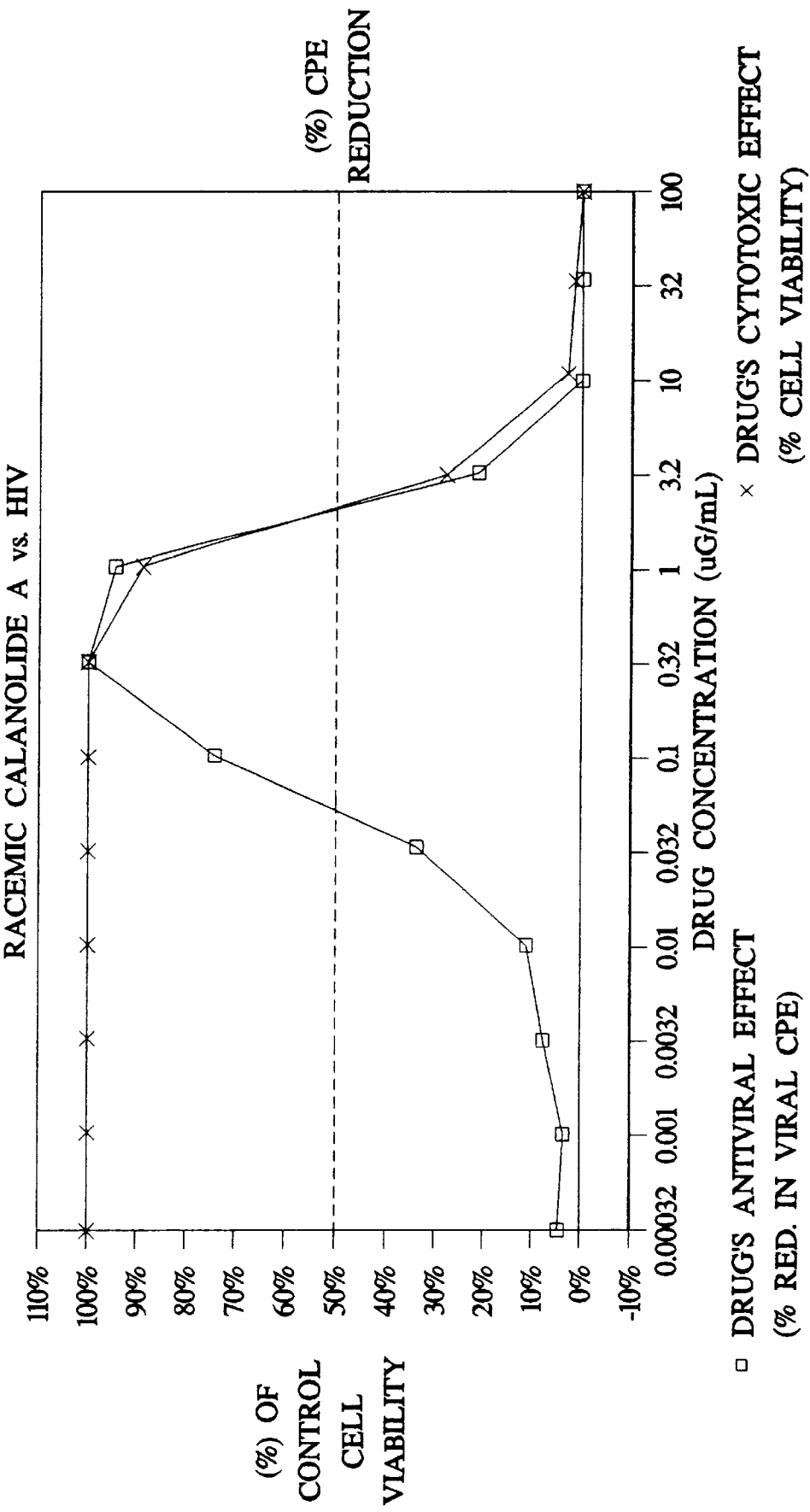

FIGS. 2(a) to 2(e) illustrate in vitro MTT assay results using H112-2 HIV viral strain[19] which was not pre-treated with AZT. As expected, the viral strain was sensitive to AZT. The data also showed that (−)-calanolide A was relatively non-toxic at concentrations of 1 g/mL but exhibited very little antiviral effect. (±)-Calanolide A was nearly as effective as (+)-calanolide A in reducing viral CPE.

Figure 3A:
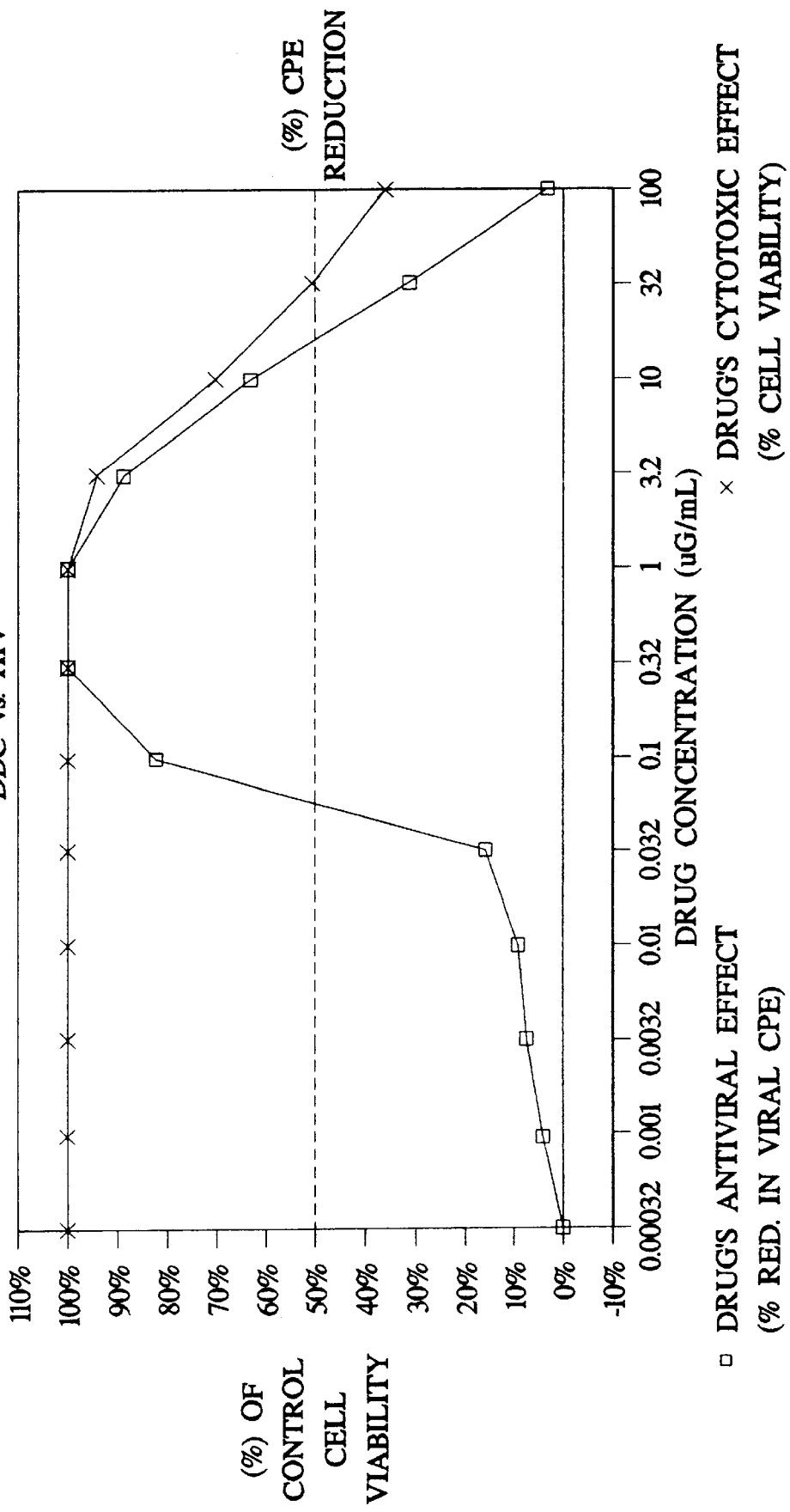
FIGS. 3(a) to 3(e) illustrate in vitro MTT assay results, as described in Example 37, using A-17 HIV viral strain which is resistant to non-nucleoside inhibitors such as TIBO but is sensitive to AZT.
Figure 3B:
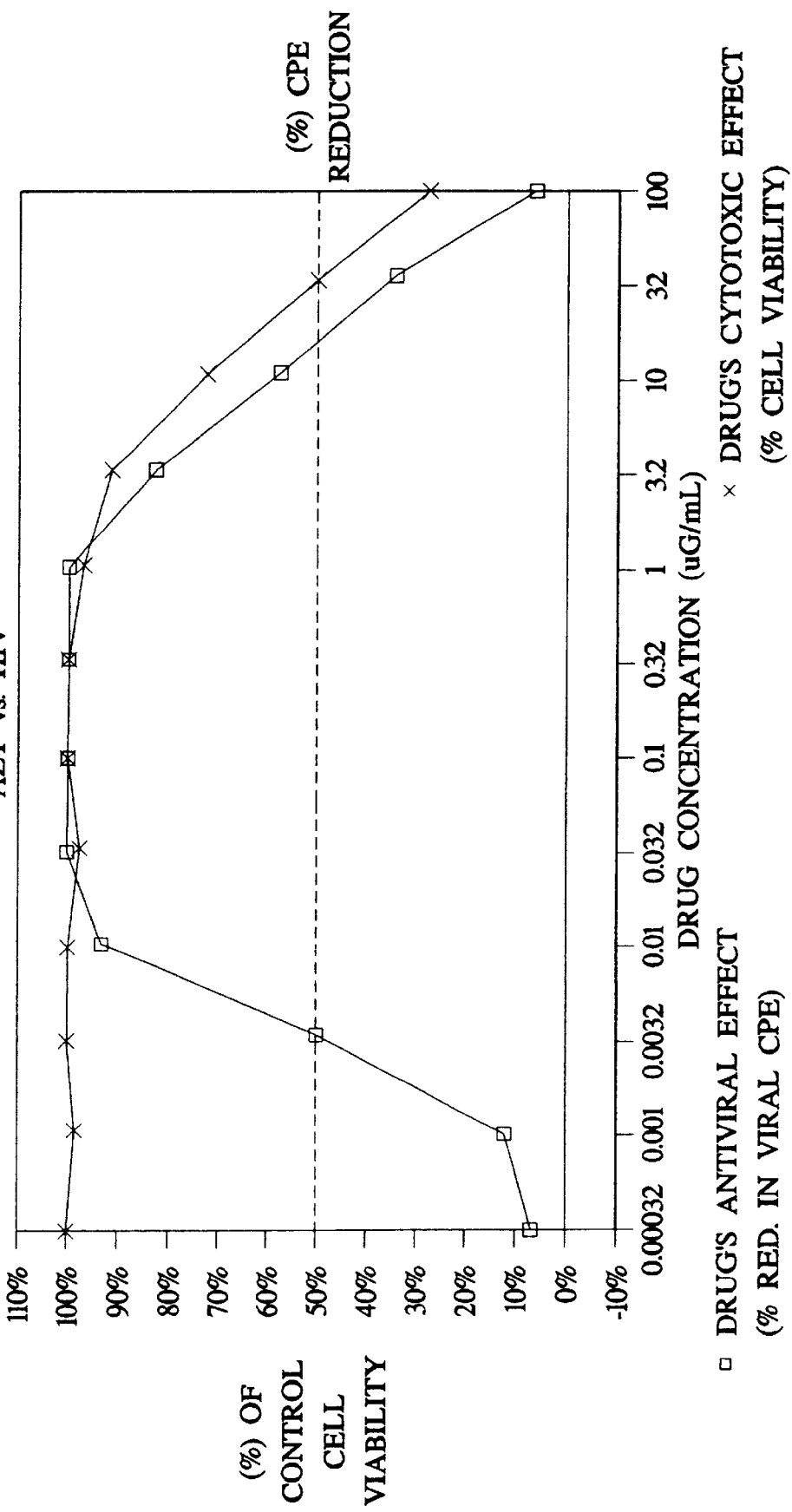
Figure 3C:
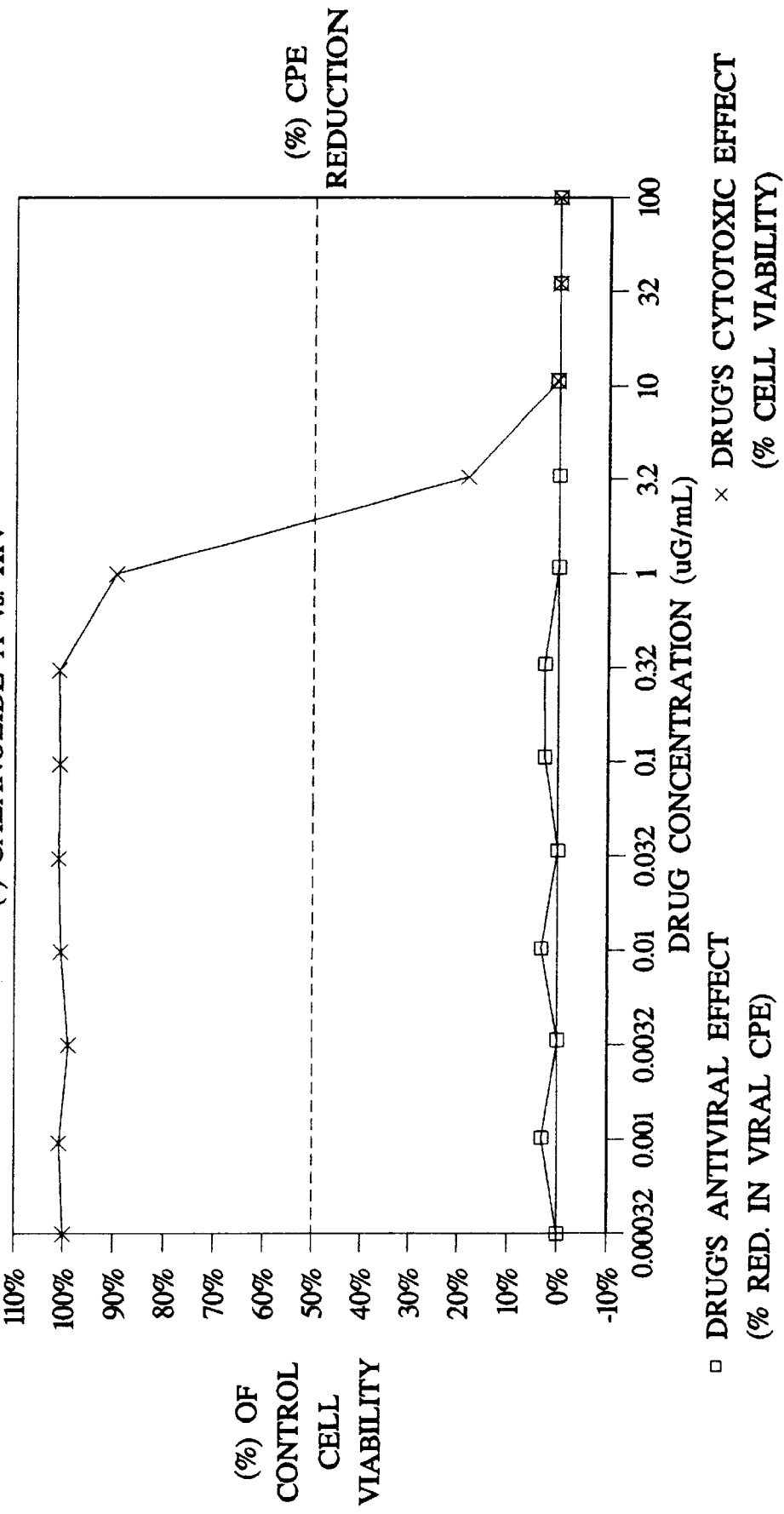
Figure 3D:
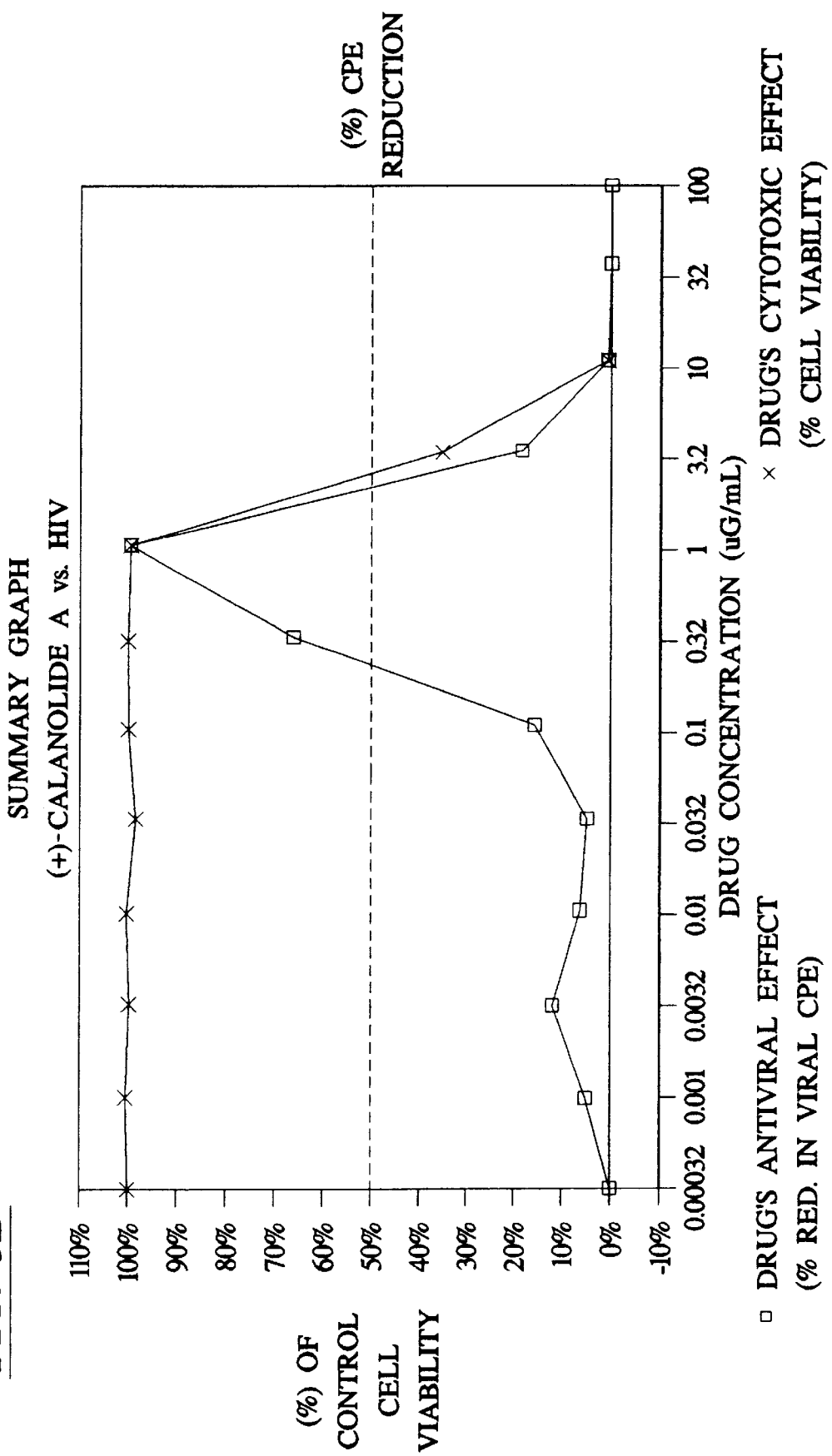
Figure 3E:
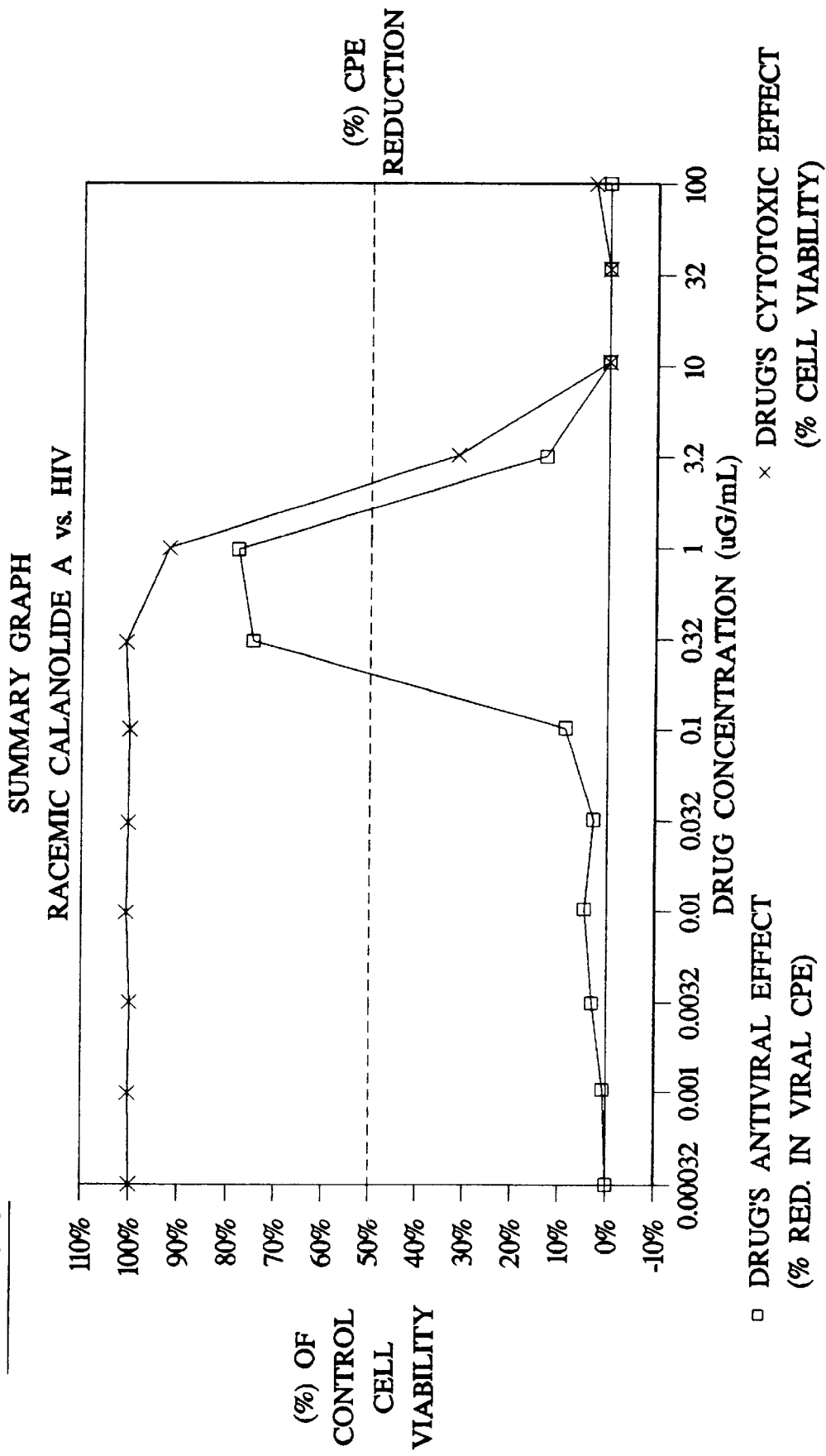

FIGS. 3(a) to 3(e) illustrate in vitro MTT assay results using A-17 HIV viral strain[20] which is resistant to non-nucleoside inhibitors such as TIBO but is sensitive to AZT. The results here parallel those shown in FIGS. 2(a)–2(e).

Figure 4A:
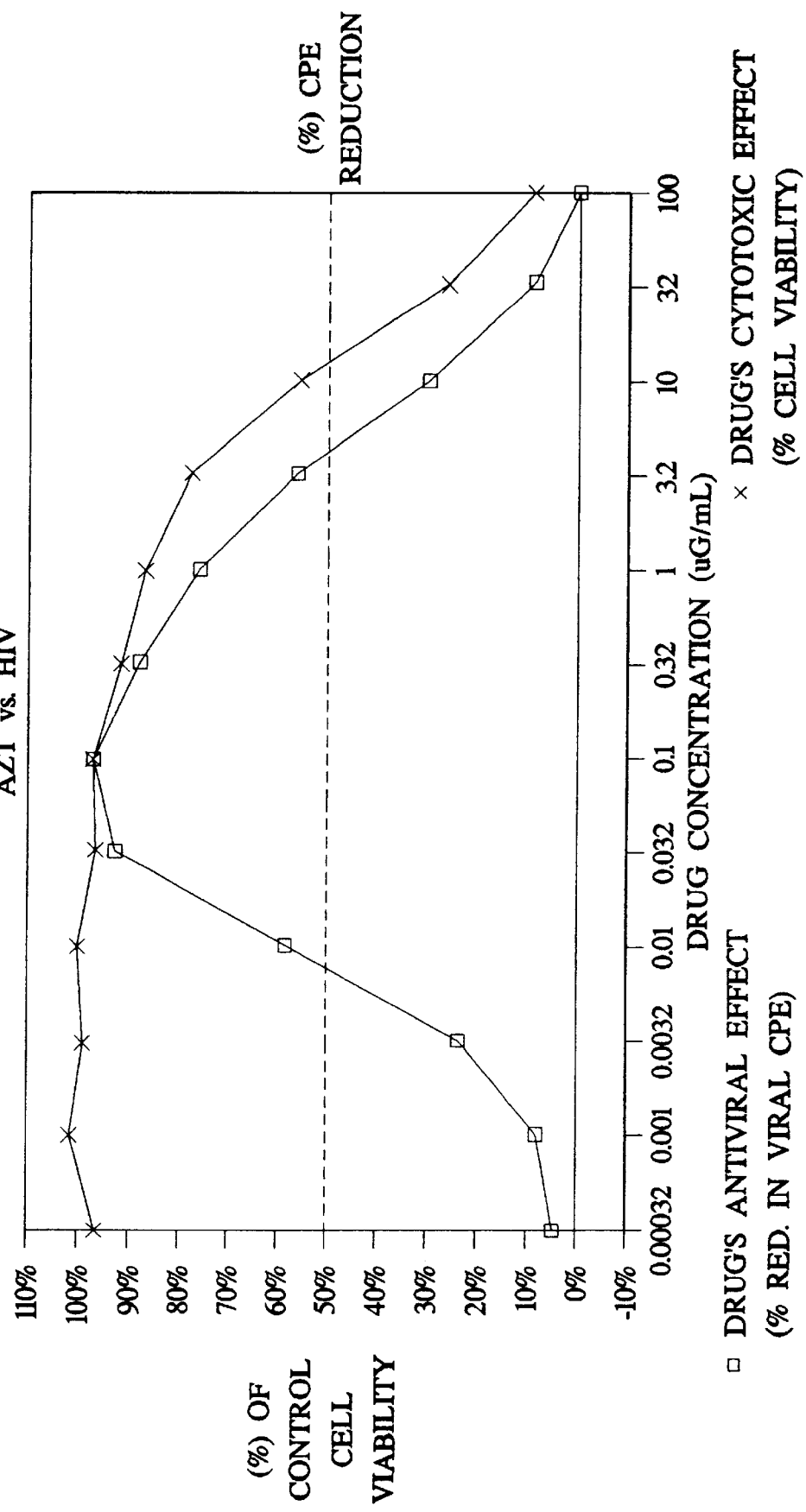
FIGS. 4(a) to 4(d) illustrate in vitro MTT assay results, as described in Example 37, using IIIB cultivated HIV viral strain.
Figure 4B:
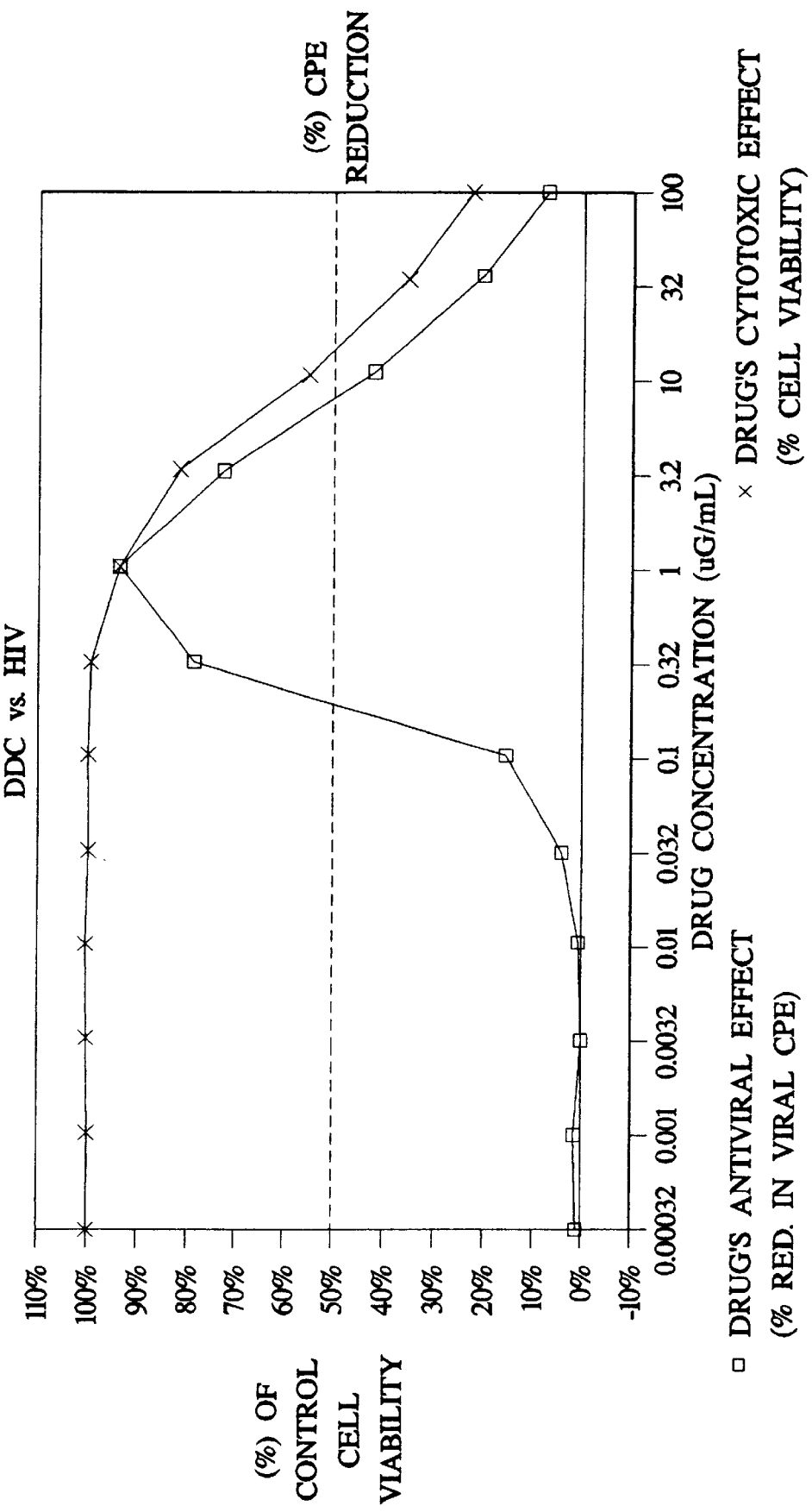
Figure 4C:
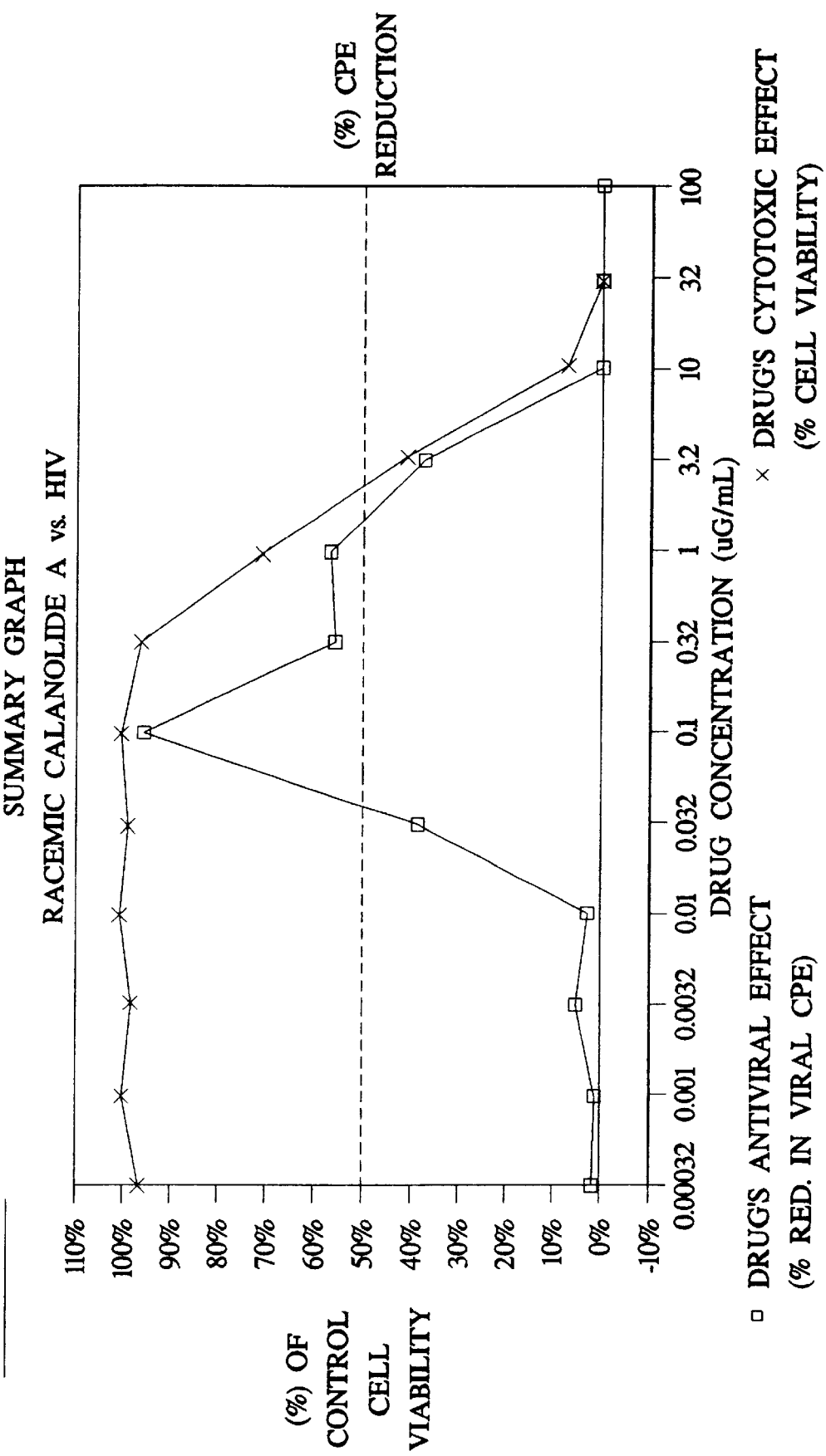
Figure 4D:
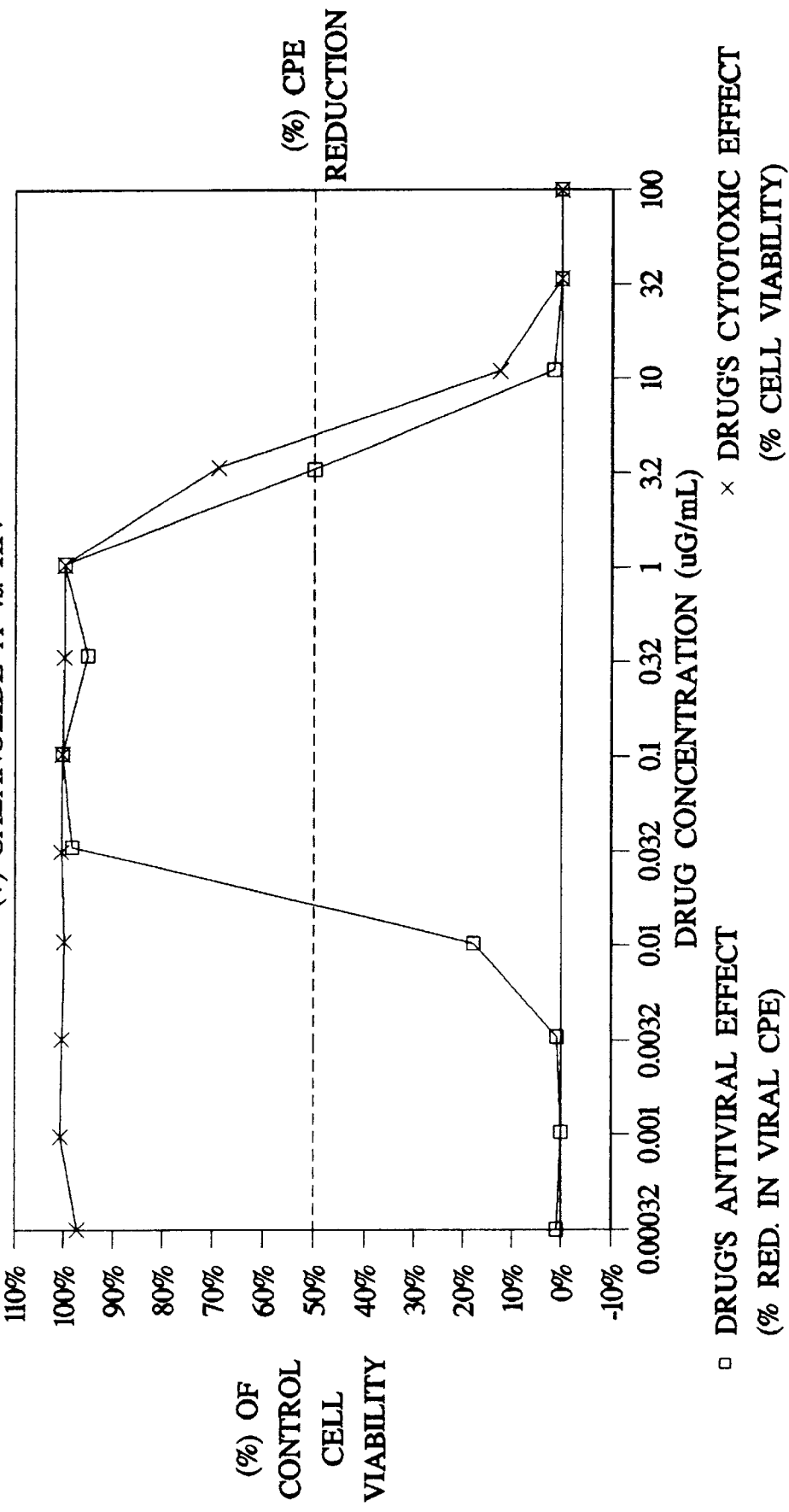
Figure 5A:
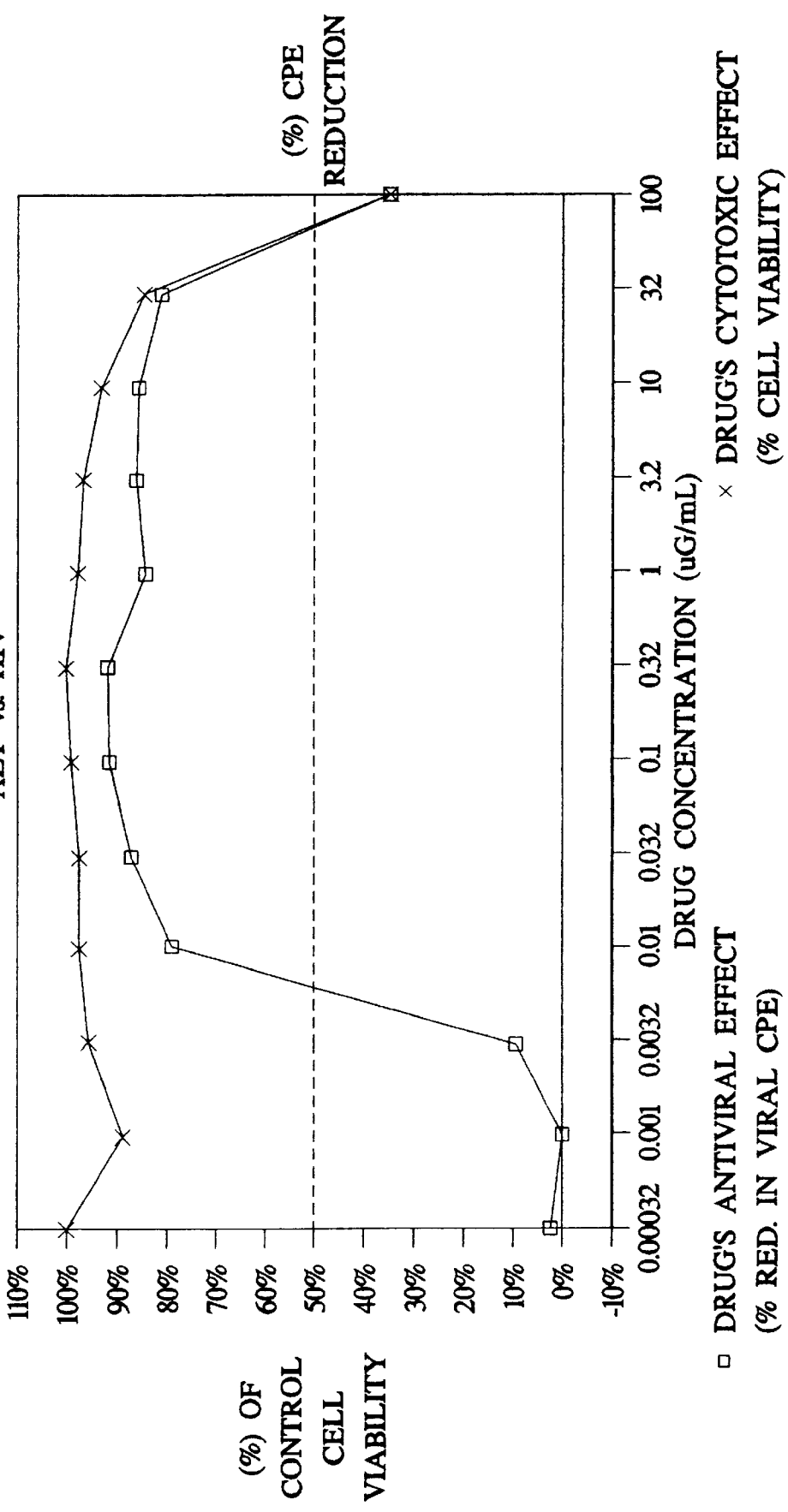
FIGS. 5(a) to 5(d) illustrate in vitro MTT assay results, as described in Example 37, using RF cultivated HIV viral strain.
Figure 5B:
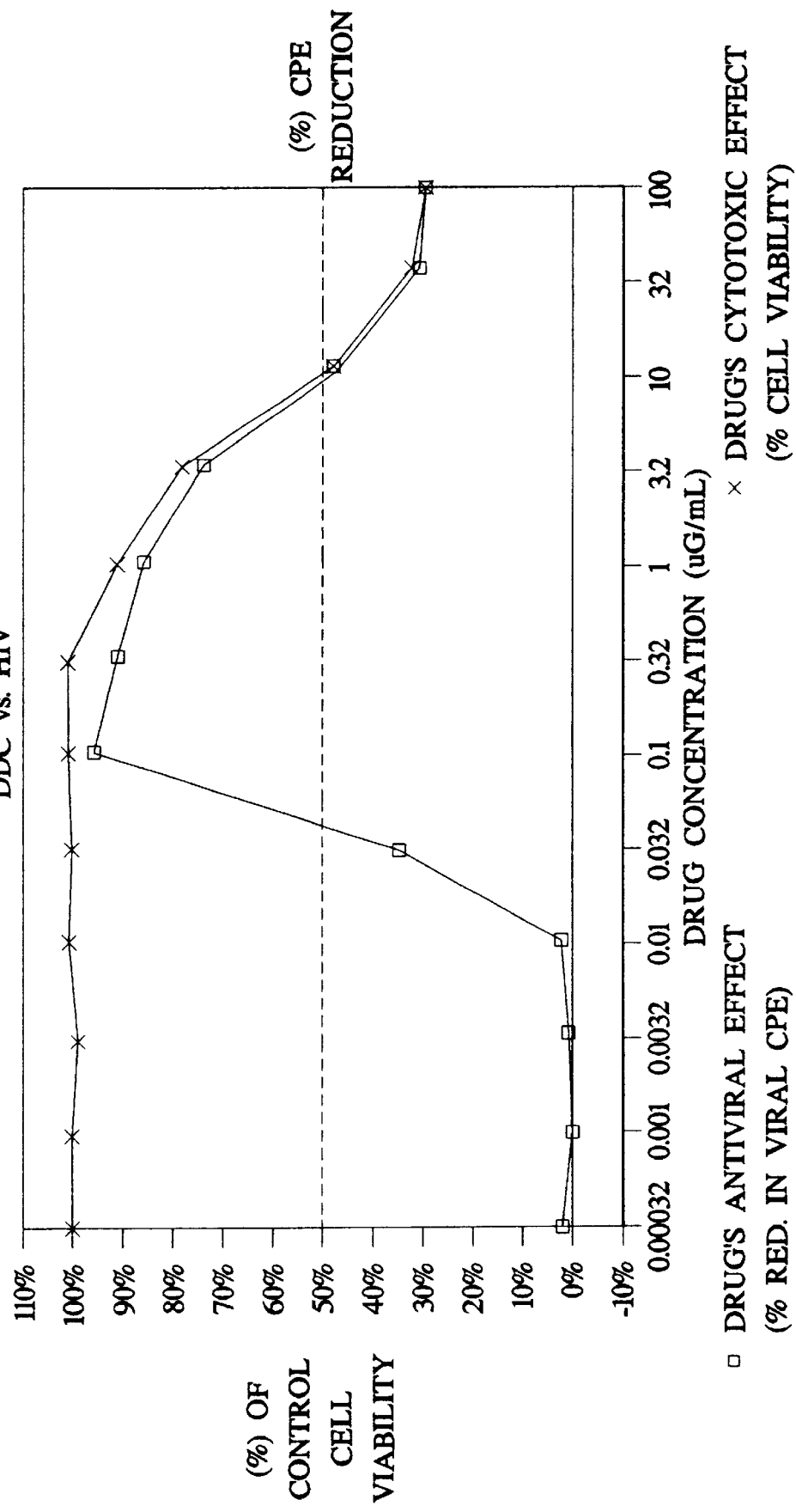
Figure 5C:
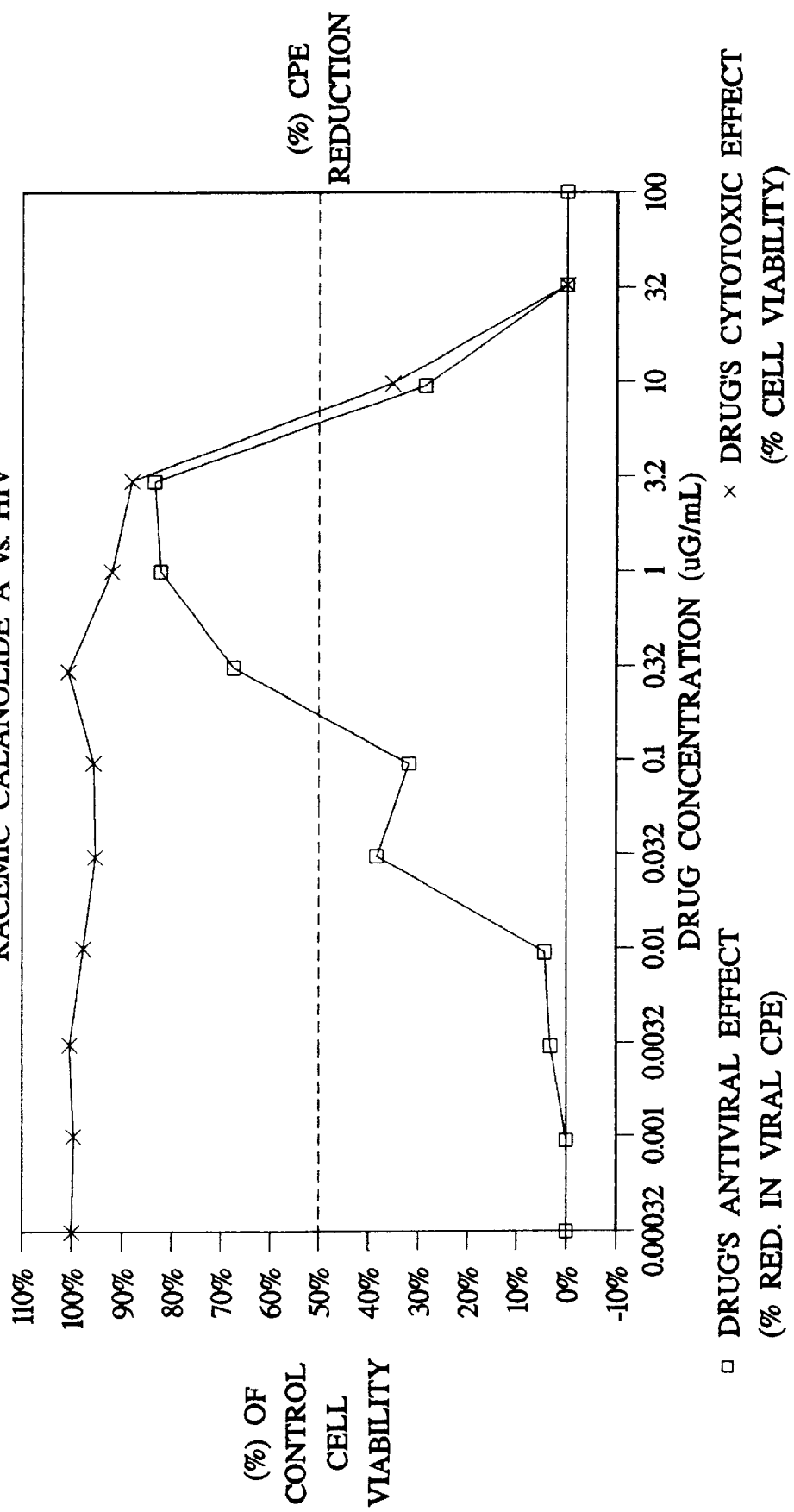
Figure 5D:
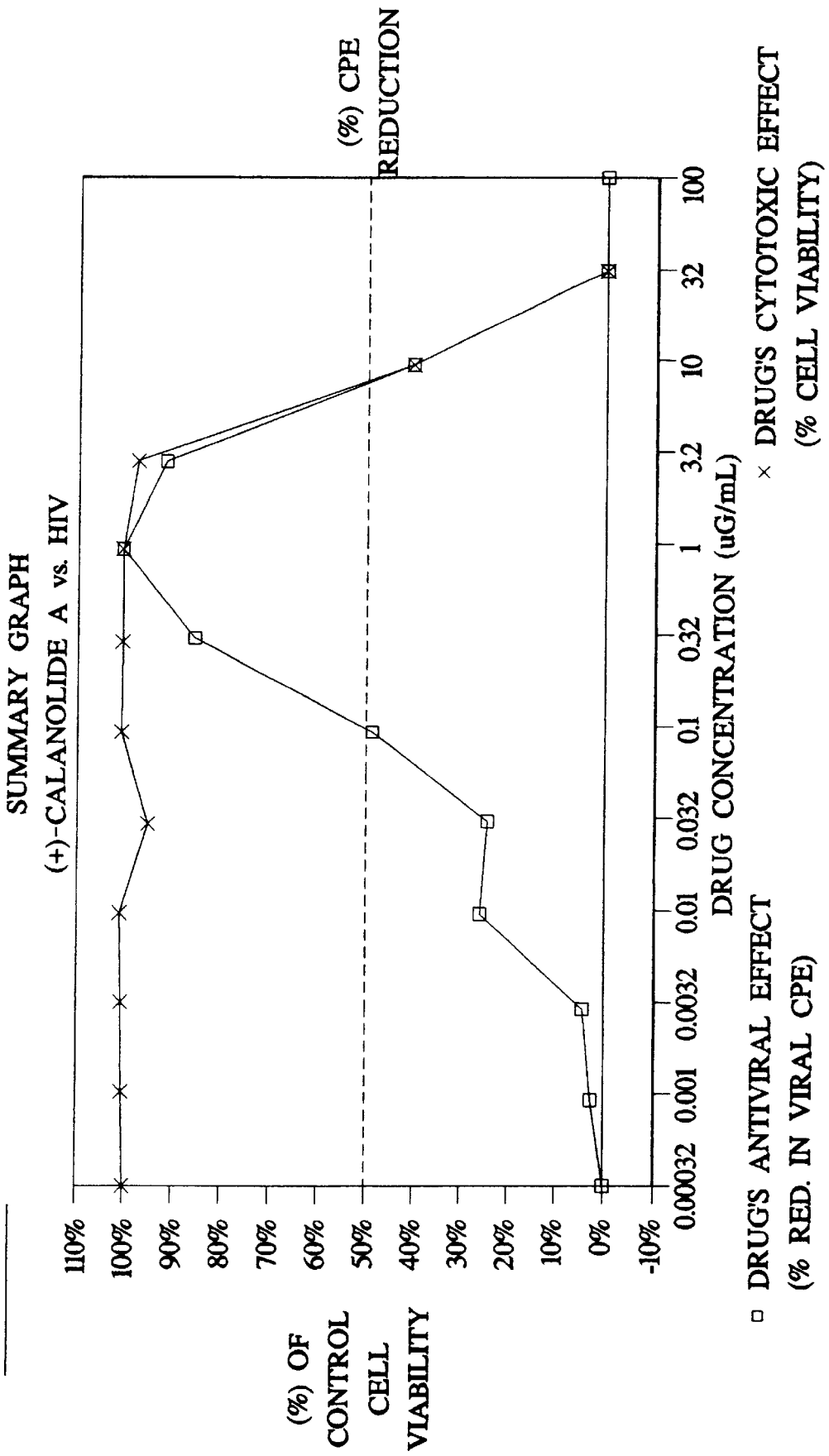
Figure 7:
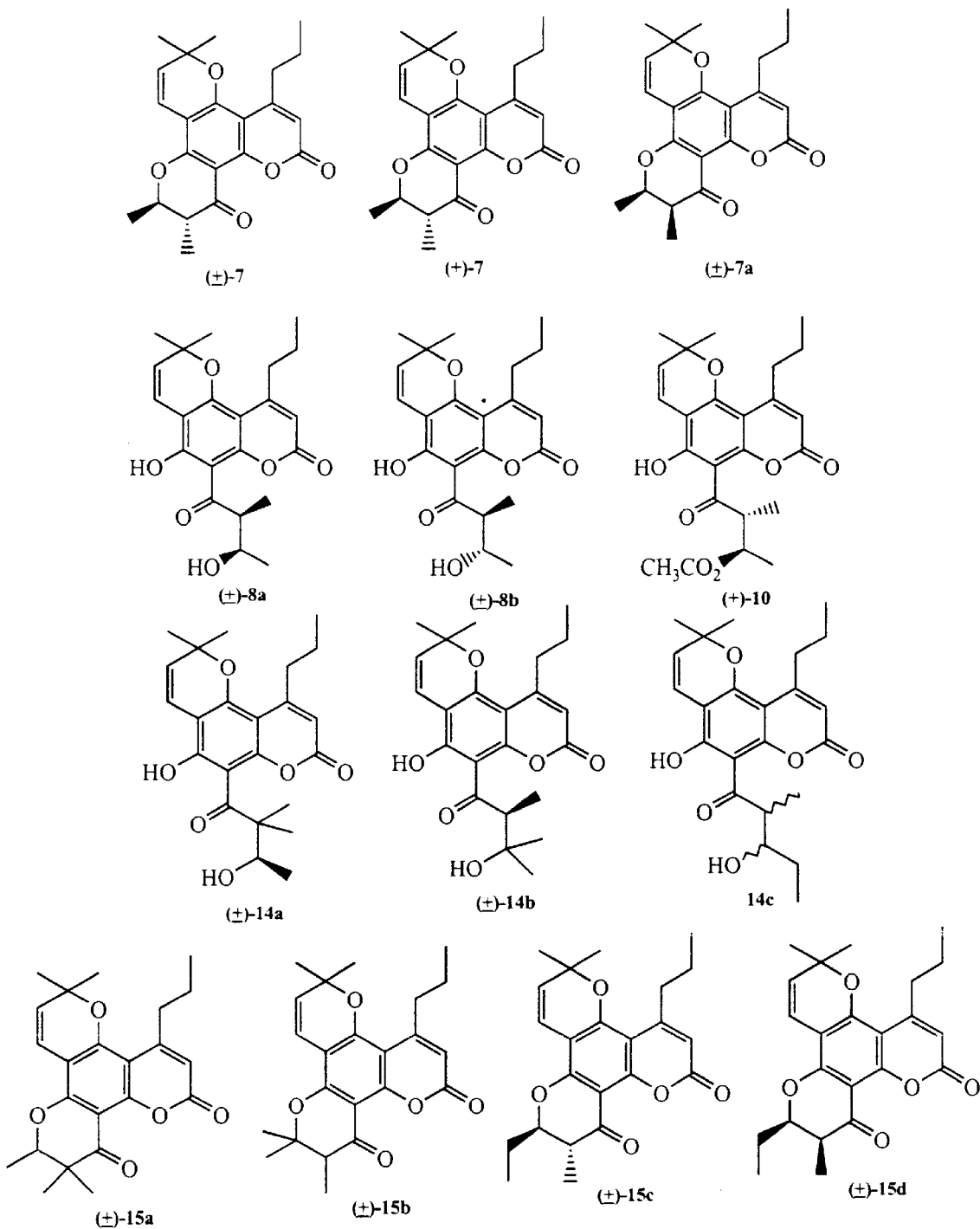
FIG. 7 illustrates representative examples of inventive compounds that were evaluated in the in vitro MTT assay of Example 38.
Figure 7:
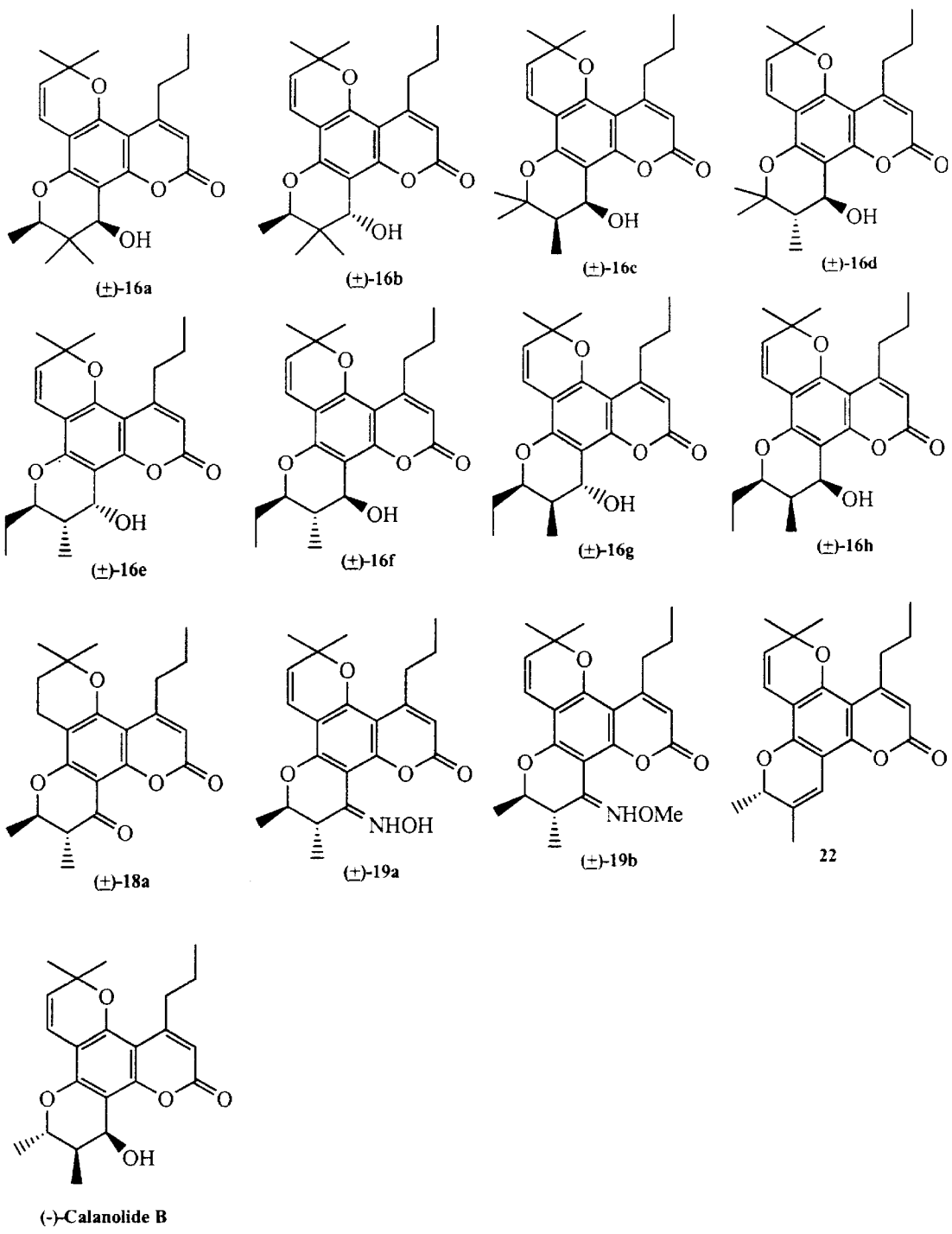
Figure 8:
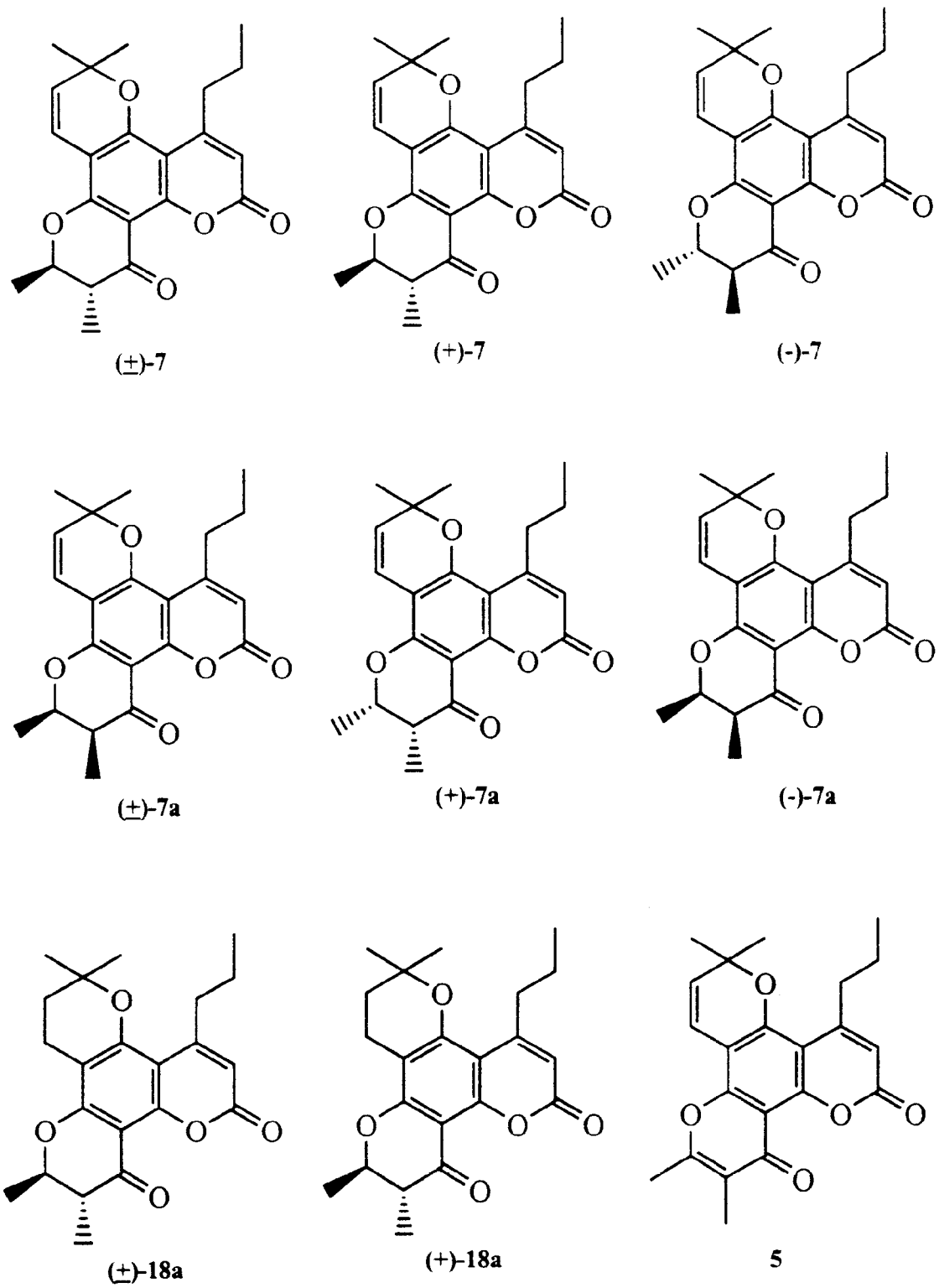
FIG. 8 illustrates representative examples of inventive compounds that were evaluated in the in vitro assays of Examples 39–41.
Figure 8:
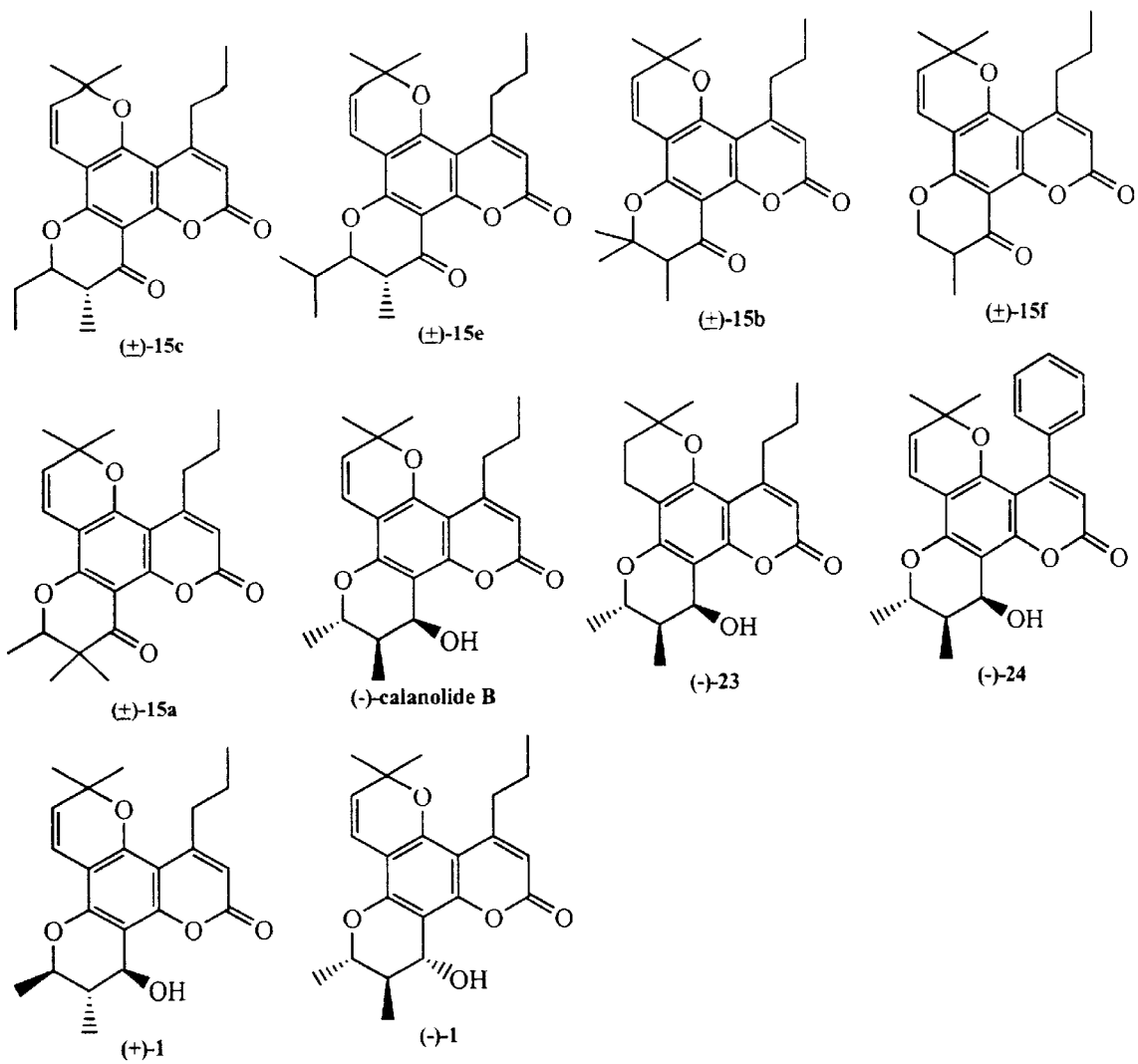

FIGS. 4(a)–(d) and 5(a)–(d) illustrate in vitro MTT assay results using lab cultivated HIV viral strains IIIB and RF, respectively. The results here also parallel those shown in FIGS. 2(a)–2(e).

EXAMPLE 38

In Vitro Evaluation of Calanolide Analogues

Selected calanolide A intermediates and analogues, prepared as described above, were evaluated using the in vitro MTT-tetrazolium assay described in Example 37. As shown in Table I below, compounds (±)-7, (±)-7, (±)-8a, (±)-8b, (+)-10, (±)-16b, (±)-16d, (±)-16e, and (±)-16f were highly efficacious in protecting cells against HIV infection.

TABLE I

| | In Vitro Anti-HIV-1 Activity of Analogues[a] | | | |
|---|---|---|---|---|
| Compound | Maximum Protection (%) | EC$_{50}$ (µM) | IC$_{50}$ (µM) | TI[b] |
| (±)-7 | 90 | 1.18 | 19.10 | 16 |
| (±)-7 | 90 | 0.68 | 72.80 | 107 |
| (±)-7a | 55 | 2.82 | 12.00 | 4 |
| (±)-8a | 84 | 6.16 | 23.8 | 4 |
| (±)-8b | 81 | 2.28 | 21.50 | 9 |
| (±)-10 | 88 | 0.89 | 9.27 | 11 |
| (±)-14a | c | c | 37.00 | c |
| (±)-14b | c | c | 27.10 | c |
| (±)-15a | c | c | 19.30 | c |
| (±)-15b | c | c | 21.00 | c |
| (±)-15c | 47 | c | 6.80 | c |
| (±)-16a | c | c | 20.30 | c |
| (±)-16b | 78 | 2.36 | 16.90 | 7 |
| (±)-16c | c | c | 21.30 | c |
| (±)-16d | 88 | 5.66 | 21.00 | 4 |
| (±)-16e | 88 | 1.67 | 14.00 | 8 |
| (±)-16f | 86 | 1.97 | 17.70 | 9 |
| (±)-16g | c | c | 11.60 | c |
| (±)-16h | c | c | 20.90 | c |
| (±)-18a | 60 | 2.47 | 9.19 | 4 |
| (±)-19a | c | c | 15.80 | c |
| (±)-19b | c | >100 | >100 | c |
| 22 | c | c | 24.70 | c |

[a]CEM-SS MTT assay
[b]IC$_{50}$/EC$_{50}$
[c]not measurable

EXAMPLE 39

Antiviral Aaticities of Calanolide Analogues Against Viruses Other than HIV

Selected calanolide analogues, prepared as described above, were evaluated against hepatitis B virus, herpes viruses (HSV-1, HSV-2, HCMV, VZV, and EBV), and respiratory viruses (influenza A, influenza B, parainfluenza, adenovirus, measles, and respiratory syncytial virus). Laboratory procedures for determining antiviral efficacy and toxicity, as well as test design, are described more fully below. Several compounds were found to be active against various viruses and the results are summarized in Table II below. Compound (+)-7 in particular was very potent against HCMV and EBV, and potent against HBV and measles.

TESTING DESIGN DETERMINING IN VITRO ACTIVITY AND TOMCITY OF POTENTIAL ANTMRAL DRUGS FOR HERPES VIRUS INFECTION

A. Primary Screening System - Human Foreskin Fibroblast Cells

1. Antiviral
   - HSV-1 or 2: Semi-automated CPE-inhibition assay (HSV-1 E-377 strain; HSV-2 MS strain)
   - CMV: Semi-automated CPE-inhibition assay (AD169 strain)
   - VZV: Plaque reduction assay (Ellen strain)
   - EBV: Superinfection of Raji or Daudi cells with P3HR-1; assay for early antigen (EA) and viral capsid antigen (VCA) production
2. Toxicity: Neutral red uptake - stationary cells; Cell proliferation assay - rapidly growing cells B. Confirmatory Assay Systems - Human Foreskin Fibroblast Cells 1. Antiviral
   - HSV-1 or 2: Plaque reduction assay - liquid overlay
   - CMV: Plaque reduction assay - liquid overlay
   - VZV: Plaque reduction assay or yield reduction assay
   - EBV: P3HR-1 infection of other B-lymphocyte cell lines. Inhibition of EBV DNA synthesis - Hybridization assay
2. Toxicity: MTT assay for cytotoxicity - stationary cells.

C. Additional Follow-up Studies

1. Antiviral: Determine activity in cell lines from other species, i.e. mice, rabbits, guinea pigs. Test sensitivity of other virus strains and clinical isolates. Determine activity against ACV and GCV resistant mutants. Determine mechanism of action
2. Toxicity: Bone marrow assays - Human CFU-GM and BFU-E clonogenic assays II. Description of Virus Isolates Used For Antiviral Evaluation A. Herpes simplex virus type 1 (HSV-I)

1. E-377 - laboratory passaged standard strain
2. E-115 - laboratory passaged standard strain
3. HL-3 - low passaged clinical isolate from herpes labialis
4. HL-34 - low passaged clinical isolate from herpes labialis
5. 4E - clinical isolate from herpes encephalitis
6. SC16 - ACV sensitive, TK positive
7. SC 16-SI - ACV resistant, TK altered
8. DM 2. 1 - ACV resistant, TK deficient
9. PAAr - PAA and PFA resistant, polymerase mutant
10. 11893 - ACV resistant, TK altered
11. 11359 - ACV resistant, TK deficient
12. 11360 - ACV resistant, TK deficient
13. B-2006 - ACV resistant, TK deficient B. Herpes simplex virus type 2 (HSV-2)

1. MS - laboratory passaged standard strain
2. X-79 - laboratory passaged standard strain
3. Jensen - low passaged clinical isolate from herpes genitalis
4. Heeter - low passaged clinical isolates from herpes genitalis
5. SR - recent clinical isolate from neonatal herpes
6. 8705 - ACV sensitive, TK positive
7. 8707 - ACV resistant, TK altered
8. 11680 - ACV resistant, TK altered
9. 12247 - ACV resistant, TK altered
10. 11575 - ACV- resistant, TK partial (low producers)
11. 11572 - ACV resistant, TK partial (low producers)
12. 11785 - ACV resistant, TK partial (low producers)
13. 8711 - ACV resistant, TK deficient
14. 11361 - ACV resistant, TK deficient
15. AG-3 - ACV resistant, TK deficient C. Human cytomegalovirus (HCMV)

1. AD109 - standard laboratory strain
2. Davis - standard laboratory strain
3. Towne - standard laboratory strain
4. EC - recent low passaged clinical isolate
5. LA - recent low passaged clinical isolate
6. CH - recent low passaged clinical isolate
7. Mann - recent low passaged clinical isolate
8. Coffman - recent low passaged clinical isolate
9. C8708/17-1-1 - clinical isolate
10. C9207 3-3-1 - ganciclovir sensitive
11. C8704 9-4-1 - ganciclovir resistant
12. C9208 5-4-2 - ganciclovir sensitive
13. C9209 1-4-4 - ganciclovir resistant
14. C8912-3 - ganciclovir sensitive
15. C8914-6 - ganciclovir resistant
16. C8805 37-1-1 - ganciclovir resistant
17. C8706 13-1-1 - ganciclovir resistant
18. AD169 $177^R$ - ganciclovir resistant and HPMPC resistant D. Murine Cytomegalovirus (MCMV)

1. Smith strain - standard laboratory strain
2. JS strain

E. Varicella Zoster Virus (VZV)

1. Ellen - standard laboratory strain
2. Oka - varicella vaccine strain
3. GLM - recent clinical isolate
4. DKG - recent clinical isolate
5. KS 1027 - recent clinical isolate
6. V8907 - clinical isolate
7. V8908 - Acyclovir resistant mutant of V8907
8. V8602 5-1-1 - clinical isolate
9. V8602 7-1-3 - ACV resistant, TK deficient
10. V8602 24-3-1 - ACV resistant, polymerase mutant
11. 40 $A^2$ - ACV resistant F. Epstein-Barr Virus (EBV)

1. P3HR-1 - standard laboratory strain

Laboratory Procedures for Determining Antiviral Efficacy and Toxicity

A. Preparation of Human Foreskin Fibroblast Cells

Newborn human foreskins were obtained as soon as possible after circumcisions were performed and placed in minimal essential medium containing vancomycin, fungizone, penicillin, and gentamycin, at the usual concentrations, for four hours. The medium was then removed, the foreskin minced into small pieces and washed repeatedly until red cells were no longer present. The tissue was then trypsinized using trypsin at 0.25% with continuous stirring for 15 minutes at 37° C. in a $CO_2$ incubator. At the end of each 15 minute period the tissue was allowed to settle to the bottom of the flask. The supernatant containing cells was poured through sterile cheesecloth into a flask containing MEM and 10% fetal bovine serum. The flask containing the medium was kept on ice throughout the trypsinizing procedure. After each addition of cells, the cheesecloth was washed with a small amount of MEM containing serum. Fresh trypsin was added each time to the foreskin pieces and the procedure repeated until no more cells became available. The cell-containing medium was then centrifuged at 1000 RPM at 4° C. for ten minutes. The supernatant liquid was discarded and the cells resuspended in a small amount of MEM with 10% FBS. The cells were then placed in an appropriate number of 25 $cm^2$ tissue culture flasks. As cells became confluent and needed trypsinization, they were gradually expanded into larger flasks. The cells were kept on vancomycin and fungizone to passage four.

B. Cytopathic Effect Inhibition Assay—HSV, HCMV, VZV

Low passage human foreskin fibroblast cells were seeded into 96-well tissue culture plates 24h prior to use at a cell concentration of $2.5 \times 10^4$ cells per mL in 0.1 mL of minimal essential medium (MEM) supplemented with 10% fetal bovine serum (FBS). The cells were then incubated for 24h at 37° C. in a $CO_2$ incubator. After incubation, the medium was removed and 100 µl of MEM containing 2% FBS was added to all but the first row. In the first row, 125 µL of experimental drug was added in triplicate wells. Medium alone was added to both cell and virus control wells. The drug in the first row of wells was then diluted serially 1:5 throughout the remaining wells by transferring 25 µL using the Cetus Liquid Handling Machine. After dilution of drug, 100 µL of the appropriate virus concentration was added to each well, excluding cell control wells, which received 100 µL of MEM. For HSV-1 and HSV-2 assays, the virus concentration utilized was 1000 PFU's per well. For CMV and VZV assays, the virus concentration added was 2500 PFU per well. The plates were then incubated at 37° C. in a $CO_2$ incubator for three days for HSV-1 and HSV-2, 10 days for VZV, or 14 days for CMV. After the incubation period, media was aspirated and the cells stained with a 0.1% crystal violet solution for 30 minutes. The stain was then removed and the plates rinsed using tap water until all excess stain was removed. The plates were allowed to dry for 24h and then read on a Skatron Plate Reader at 620 nm.

C. Plaque Reduction Assay for HSV-1 and HSV-2 using Semi-Solid Overlay

Two days prior to use, HFF cells are plated into six-well plates and incubated at 37° C. with 5% $CO_2$ and 90% humidity. On the date of assay, the drug is made up at twice the desired concentration in 2×MEM and then serially diluted 1:5 in 2×MEM using six concentrations of drug. The initial starting concentration is usually 200 µg/mL down to 0.06 µg/mL. The virus to be used is diluted in MEM containing 10% FBS to a desired concentration which will give 20–30 plaques per well. The media is then aspirated from the wells and 0.2 mL of virus is added to each well in duplicate with 0.2 mL of media being added to drug toxicity wells. The plates are then incubated for one hour with shaking every fifteen minutes. After the incubation period, an equal amount of 1% agarose was added to an equal volume of each drug dilution. This will give final drug concentrations beginning with 100 µg/mL and ending with 0.03 µg/mL and a final agarose overlay concentration of 0.5%. The drug agarose mixture is applied to each well in 2 mL volume and the plates then incubated for three days, after which the cells were stained with a 1.5% solution of neutral red. At the end of 4–6hr incubation period, the stain is aspirated, and plaques counted using a stereomicroscope at 10×magnification.

$EC_{50}$ (50% effective concentration) is the concentration required to inhibit viral cytopathogenicity by 50%

$IC_{50}$ (50% inhibitory concentration) is the concentration required to inhibit cell proliferation by 50%

Selective Index (S.I.) $IC_{50}EC_{50}$

D. VZV Plaque Reduction Assay—Semi-Solid overlay.

The procedure is essentially the same as for the HSV plaque assay described above with two exceptions:
1. After addition of the drug, the plates are incubated for ten days.
2. On days three and six, an additional 1 mL overlay with equal amounts of 2×MEM and 1% agarose are added.

E. CMV Plaque Assay—Semi-Solid Overlay

The procedure again is nearly the same as for HSV with a few minor changes. The agarose used for both the initial overlay and the two subsequent overlays is 0.8% rather than 1%. The assay is incubated for 14 days with the additional 1 mL overlays being applied on days four and eight.

F. Plaque Reduction Assays Using Liquid Medium Overlay

The procedure for the liquid overlay plaque assay is similar to that using the agarose overlay. The procedure for adding the virus is the same as for the regular plaque assay. The drugs are made up in a concentration to be used in MEM with 2% FBS. The drugs are not made up at 2×concentration as in the previous assays but are made up at the desired concentration. For HSV-1 and HSV-2 assays, an antibody preparation obtained from Baxter Health Care Corporation is diluted 1:500 and added to the media that the drug is diluted in. For CMV and VZV, no antibody in the overlay is utilized. For the CMV assay, additional medium without new drug is added on day five and allowed to incubate for a total of 10 days. For VZV, additional medium is added on day five and incubated for a total of 10 days. At the end of the incubation period for all of the assays, 2mL of 1:10 dilution of stock neutral is added to each well incubated for six hours. The liquid is then aspirated off and plaques enumerated using a stereomicroscope.

G. Screening and Confirmation Assays for EBV

1. Virus

There are two prototypes of infectious EBV. One is exemplified by the virus derived from supernatant fluids of the P3HR-1cell line. This cell line produces nontransforming virus that causes the production of early antigen (EA) after primary infection or superinfection of B cell lines. The other prototype is exemplified by the B-95–8 virus. This virus immortalized cord blood lymphocytes and induced tumors in marmosets. It does not, however, induce an abortive productive infection even in cell lines harboring EBV genome copies. The virus used in our assays is P3HR-1.

2. Cell Lines

Ramos is an exceptional B cell line derived from Burkitt's lymphoma tumor but containing no detectable EBV genome copies and is EBNA negative. Ramos/AW was obtained by in vitro infection of Ramos with the P3HR-1 virus and contains one resident EBV genome copy/cell. Raji is a Burkitt's lymphoma cell line containing 60 EBV genomes/cell, and will be the primary cell used for screening antiviral activity against EBV EA expression. Daudi is a low level producer that contains 152 EBV genome copies/cell. It spontaneously expresses EBV EA in 0.25%-0.5% of the cells. It will be used in follow-up studies to confirm activity. These cell lines respond to superinfection by EBV by expressing EA(D), EA(R), and VCA. All cell lines are maintained in RPMI-1640 medium supplemented by 10% FCS, L-glutamine and 100 µg/mL gentamicin. The cultures are fed twice weekly and the cell concentration adjusted to $3 \times 10^5$/mL. The cells are kept at 37° C. in a humidified atmosphere with 5% $CO_2$.

3. lnmunofluorescence Assays with Monoclonal Antibodies

Cells are infected with the P3HR-1 strain of EBV and the drugs to be tested are added after adsorption (45 minutes at 37° C.) and washing of the cell cultures. The cultures are incubated for two days in complete medium to allow viral gene expression. Following the 48 hr incubation period, the number of cells of each sample are counted and smears made. Monoclonal antibodies to the different EA components and VCA are then added to the cells incubated and washed. This is followed by a fluorescein conjugated rabbit anti-mouse Ig antibody; and the number of fluorescence positive cells in the smears are counted. The total number of cells in the cultures positive for EA or VCA are then calculated and compared.

H. Cell Proliferation Assay—Toxicity

Twenty-four hours prior to assay, HFF cells are seeded in 6-well plates at a concentration of $2.5 \times 10^4$ cells per well in MEM containing 10% FBS. On the day of the assay, drugs are diluted serially in MEM containing 10% FBS at increments of 1:5 covering a range from 100 μg/mL to 0.03 μg/mL. For drugs that have to be solubilized in DMSO, control wells receive MEM containing 10% DMSO. The media from the wells is then aspirated and 2 mL of each drug concentration is then added to each well. The cells are then incubated in a $CO_2$ incubator at 37° C. for 72h. At the end of this time, the media-drug solution is removed and the cells washed. One mL of 0.25% trypsin is added to each well and incubated until the cells start to come off of the plate. The cell-media mixture is then pipetted up and down vigorously to break up the cell suspension, and 0.2 mL of the mixture is added to 9.8 mL of Isoton III and counted using a Coulter Counter. Each sample is counted three times with three replicate wells per sample.

I. MTT Assay for Cell Cytotoxicity

Twenty-four hours prior to assay, HFF cells are plated into 96-well plates at a concentration of $2.5 \times 10^4$ cells per well. After 24 h, the media is aspirated and 125 mL of drug is added to the first row of wells and then diluted serially 1:5 using the automated Cetus Liquid Handling System in a manner similar to that used in the CPE assay. The plates are then incubated in a $CO_2$ incubator at 37° C. for seven days. At this time, each well receives 50 mL of 1 μg/mL solution of MTT in Dulbecco's Phosphate Buffered Saline. The plates are then incubated for an additional four hours. At this time, the media is removed and replaced with 100 μL of 0.04N hydrochloric acid in isopropanol. After shaking briefly, the plates are then read on a plate reader at 550 nm.

J. Neutral Red Uptake Assay—Toxicity

The procedure for plating cells and adding drug is the same as for the MTT Assay.

After drug addition, the plates are incubated for seven days in a $CO_2$ incubator at 37° C. At this time the media/drug is aspirated and 200 μL/well of 0.01% neutral red in DPBS is added. This is incubated in the $CO_2$ incubator for one hour. The dye is aspirated and the cells are washed using a Nunc Plate Washer. After removing the DPBS wash, 200 μg/well of 50% EtOH/1% glacial acetic acid (in $H_2O$) is added. The plates are rotated for 15 minutes and the optical densities are read at 550 nm on a plate reader.

ASSAY METHODS OF HBV & INFLUENZA VIRUS: ANALYSIS OF POTENTIAL ANTIVIRAL AGENTS AGAINST HBV REPLICATION IN CULTURES OF 2.2.15 CELLS

Antiviral Assays

The protocol for assaying anti-HBV compounds in cultures of 2.2.15 cells can be briefly summarized as follows (Korba and Milman, 1991, Antiviral Res. 217:217). Chronically HBV-producing human liver cells (Acs, et al., 1987, PNAS 84:4641) are seeded into 24-well tissue culture plates and grown to confluence.

Test compounds are then added daily for a continuous 9 day period. Culture medium (changed daily during the treatment period) is collected and stored for analysis of extracellular (virion) HBV DNA after 0, 3, 6, and 9 days of treatment. Treated cells are lysed 24 hours following day 9 of treatment for the analysis of intracellular HBV genomic forms. HBV DVA is then analyzed in a quantitative and qualitative manner for overall levels of HBV DNA (both extracellular and intracellular DNA) and the relative rate of HBV replication (intracellular DNA).

Toxicity Assays

The protocol for determining toxicity of compounds in cultures of 2.2.15 cells can be briefly summarized as follows. Cells of 2.2.15 were grown to confluence in 96-well flat-bottomed tissue culture plates and treated with compounds (in 0.2 mL culture medium/well) as described above. Four concentrations of each compound were assayed, each in triplicate cultures, in 3- to 10-fold steps. Untreated control cultures were maintained on each 96-well plate. On each 96-well plate, wells containing no cells were used to correct for light scattering. Toxicity was determined by the inhibition of the uptake of neutral red dye, determined by absorbance at 510 nm relative to untreated cells (Finter et al., 1969, J. Med. Chem 5:419), 24 hours following day 9 of treatment.

Assay Parameters

Both intracellular and extracellular HBV DNA are analyzed in order to (i) allow for verification of compound efficacy and (ii) provide possible data on the target site in the HBV replication pathway for the compound from examination of the pattern of viral replicative forms. The culture medium is changed daily during the treatment period to (i) prevent the buildup of potentially toxic metabolites derived from test compounds and (ii) provide an analysis of HBV virion production during discrete 24-hour intervals which enables a quantitative comparison of any effect on virion production.

The analysis of HBV DNA is performed using blot hybridization techniques (Southern and slot blot) and $[^{32}P]$-labeled HBV-specific probes. HBV DNA levels are measured by comparison to known amounts of HBV DNA standards applied to every nitrocellulose membrane (gel or slot blot). An AMBIS beta scanner, which measures the radioactive decay of the hybridized probes directly from the nitrocellulose membranes, is used for the quantitative analysis. Standard curves, generated by multiple analyses, are used to correlate CPM measurements made by the beta scanner with relative levels of target HBV DNA. The levels of HBV virion DNA released into the culture medium are analyzed by a slot blot hybridization procedure. HBV DNA levels are then compared to those at Day 0 to determine the effect of drug treatment.

A typical pattern of intracellular HBV DNA is displayed in the figure below (panel A, lanes 1 and 2). The levels of HBV DNA in each of three classes of viral genomic forms are individually quantitated in order to evaluate the replication status of the virus: episomal monomers, DNA replication intermediates [RI], and integrated HBV DNA.

The levels of RI and episomal monomers are used as an indicator of the relative level of HBV replication. Integrated HBV DNA is used to normalize the relative amounts of DNA in each lane because the levels of this class of HBV DNA would be expected to remain constant on a per cell basis. The type of changes in the intracellular HBV DNA patterns which are indicative of a decline in HBV replication are shown in lanes 3 and 4 of the figure. Inhibition of HBV DNA replication is indicated by the loss of RI without changes in the level of integrated HBV DNA.

ASSAYS FOR ANTIVIRAL ACTIVITY AGAINST RESPIRATORY VIRUSES

1. Viruses Used in Primary Screen

A. Influenza A and B

Virus strains: A/Texas/36/91 (H1N1) (Source: Center for Disease Control and Prevention [CDC]), A/Beijing/2/92 (H3N2) (Source: CDC), B/Panama/45/90 (Source: CDC), A/NWS/33 (H1N1) (Source: American Type Culture Collection [ATCC]). (All but A/NWS/33 are tested in the presence of trypsin). Cell lines: Madin Darby canine kidney (MDCK) cells.

B. Respiratory syncytial virus

Virus strain: Utah 89 (source: Utah State Diagnostic Laboratory) Cell line: African green monkey kidney (MA-104) cells.

C. Parainfluenza type 3 virus

Virus strain: C243 (Source ATCC) Cell line: African green monkey kidney (MA-104) cells.

D. Measles virus

Virus strain: CC (Source: Pennsylvania State University) Cell line: African green monkey kidney (BSC-1) cells.

E. Adenovirus type 5

Virus strain: Adenoid 75 (Source ATCC) Cell line: Human lung carcinoma (A549) cells.

2. Methods for Assay of Antiviral Activity

A. Inhibition of Viral Cytopathic Effect (CPE)

This test, run in 96-well flat-bottomed microplates, is used for the initial antiviral evaluation of all new test compounds. In this CPE inhibition test, seven one-half $\log_{10}$ dilutions of each test compound will be added to 4 cups containing the cell monolayer; within 5 minutes, the virus is then added and the plate sealed, incubated at 37° C. and CPE read microscopically when untreated infected controls develop a 3 to 4+CPE (approximately 72 hr). A known positive control drug is evaluated in parallel with test drugs in each test. This drug is ribavirin for influenza, measles, respiratory syncytial and parainfluenza viruses, and HPMPA for adenovirus. The data are expressed as 50% effective (virus-inhibitory) concentrations ($EC_{50}$).

B. Increase in Neutral Red (NR) Dye Uptake

This test is run to validate the CPE inhibition seen in the initial test, and utilizes the same 96-well microplates after the CPE has been read. Neutral red is added to the medium; cells not damaged by virus take up a greater amount of dye, which is read on a computerized microplate autoreader. An $EC_{50}$ is determined from this dye uptake.

C. Decrease in Virus Yield

Compounds considered active by CPE inhibition and by NR dye uptake will be retested using both CPE inhibition, and, using the same plate, effect on reduction of virus yield by assaying frozen and thawed eluates from each cup for virus titer by serial dilution onto monolayers of susceptible cells. Development of CPE in these cells is the indication of presence of infectious virus. As in the initial tests, a known active drug is run in parallel as a positive control. The 90% effective concentration ($EC_{90}$), which is that test drug concentration that inhibits virus yield by 1 $\log_{10}$, is determined from these data.

3. Methods for Assay of Cytotoxicity

A. Visual Observation

In the CPE inhibition tests, two wells of uninfected cells treated with each concentration of test compound are run in parallel with the infected, treated wells. At the time CPE is determined microscopically, the toxicity control cells are also examined microscopically for any changes in cell appearance compared to normal control cells run in the same plate. These changes may be enlargement, granularity, cells with ragged edges, a filmy appearance, rounding, detachment from the surface of the well, or other changes. These changes are given a designation of T (100% toxic), $P_{VH}$ partially toxic-very heavy-80%), $P_H$ (partially toxic-heavy-60%), P (partially toxic 40%), $P_{SI}$ (partially toxic-slight-20%), or 0 (no toxicity-0%), conforming to the degree of cytotoxicity seen. A 50% cell inhibitory (cytotoxic) concentration ($IC_{50}$) is determined by regression analysis of these data.

B. Neutral Red Uptake

In the neutral red dye uptake phase of the antiviral test described above, the two toxicity control wells also receive neutral red and the degree of color intensity is determined spectrophotometrically. A neutral red IC50 (NR $IC_{50}$) is subsequently determined.

C. Viable Cell Count

Compounds considered to have significant antiviral activity in the initial CPE and NR tests are retested for their effects on cell growth. In this test, 12-well tissue culture plates are seeded with cells (sufficient to be approximately 20% confluent in the well) and exposed to varying concentrations of the test drug while the cells are dividing rapidly. The plates are then incubated in a $CO_2$ incubator at 37° C. for 72 hr, at which time the media-drug solution is removed and the cells washed. Trypsin is added to remove the cells, which are then counted using a Coulter cell counter. An $IC_{50}$ is then determined using the average of three separate counts at each drug dilution.

4. Data Analysis

Each test compound's antiviral activity is expressed as a selectivity index (SI), which is the $IC_{50}$ or $IC_{90}$, divided by the $EC_{50}$. Generally, an SI of 10 or greater is indicative of positive antiviral activity, although other factors, such as a low SI for the positive control, are also taken into consideration.

TABLE II

Antiviral Activities of Calanolide Analogues against Viruses Other Than HIV

| | HBV[a] | | | HCMV[b] | | | EBV[b] | | | VZV[b] | | | Others[a] | | |
|---|---|---|---|---|---|---|---|---|---|---|---|---|---|---|---|
| | $EC_{50}$ | $IC_{50}$ | $SI^c$ | $EC_{50}$ | $IC_{50}$ | $SI^c$ | $EC_{50}$ | $IC_{50}$ | $SI^c$ | $EC_{50}$ | $IC_{50}$ | $SI^c$ | $EC_{50}$ | $IC_{50}$ | $SI^c$ |
| (±)-7 | | | | | | | | | | | | | | | |
| (+)-7 | 7.2 | 57 | 8 | 0.11 | 47.9 | 435 | 0.94 | >50 | >53 | 55.9 | <100 | 1.8 | 3[g] | 10[g] | 3.3[g] |
| (−)-7 | >10 | 327 | <32 | >20 | 23.7 | <1.2 | >20 | 23.7 | <1 | | | | | | |

TABLE II-continued

Antiviral Activities of Calanolide Analogues against Viruses Other Than HIV

| | HBV[a] | | | HCMV[b] | | | EBV[b] | | | VZV[b] | | | Others[a] | | |
|---|---|---|---|---|---|---|---|---|---|---|---|---|---|---|---|
| | $EC_{50}$ | $IC_{50}$ | $SI^c$ | $EC_{50}$ | $IC_{50}$ | $SI^c$ | $EC_{50}$ | $IC_{50}$ | $SI^c$ | $EC_{50}$ | $IC_{50}$ | $SI^c$ | $EC_{50}$ | $IC_{50}$ | $SI^c$ |
| (±)-7a | 44 | 32 | 1 | 0.15 | 19.8 | 132 | >50 | >50 | 1 | 13.7 | 33.3 | 2.4 | 13.7[g] | 33.3[g] | 2.4[g] |
| (+)-7a | 2.5 | 382 | 153[d] | >4.0 | 11.6 | <3 | >4.0 | 11.9 | <3 | | | | | | |
| (−)-7a | >10 | 86 | <8.6 | >4.0 | 11.9 | <3 | | | | | | | | | |
| (±)-18a | >10 | 88 | <9 | >4.0 | 19.5 | <5 | 24.5 | >50 | >2 | 15.4 | 33.3 | 2.2 | | | |
| (+)-13a | >10 | 88 | 1 | >100 | >100 | <1 | >50 | >50 | <1 | >100 | >100 | <1 | | | |
| 5 | >10 | 2085 | <209 | >100 | >100 | <1 | >50 | >50 | <1 | >20 | 52.2 | <3 | | | |
| (±)-15c | >10 | 152 | <15 | >20 | 77.6 | <4 | >50 | >50 | <1 | >20 | 68.0 | <3 | | | |
| (±)-15e | >10 | 86 | <8.6 | >20 | 75.3 | <4 | >50 | >50 | <1 | >100 | >100 | <1 | | | |
| (±)-15b | >10 | 307 | <31 | >20 | 52.3 | <3 | >50 | >50 | <1 | >20 | 66.7 | <3 | | | |
| (±)-15f | 0.67 | 270 | 400[e] | >100 | >100 | <1 | >50 | >50 | <1 | >20 | 60.0 | <3 | | | |
| (±)-15a | 2.0 | 1986 | 993[f] | >100 | >100 | <1 | | | | | | | | | |
| (−)-calanolide B | >10 | 1000 | <100 | 2.6 | 78.4 | 30 | >50 | >50 | <1 | >4.0 | 20.0 | <5 | | | |
| (−)-23 | 3.5 | 340 | 97 | >4.0 | 18.8 | <5 | | | | >4.0 | 16.0 | <4 | 20[h] | >100[h] | >5[h] |
| (−)-24 | >10 | 151 | <15 | >4.0 | 14.4 | <4 | >50 | >50 | <1 | >4.0 | 12.0 | <3 | 5.7[i] | >100[i] | >18[i] |
| (+)-1 | >2.6 | 175 | <67 | >20 | 86.2 | <4 | >50 | >50 | <1 | | | | | | |
| (−)-1 | >30 | 173 | <6 | >20 | 80.3 | <4 | >100 | >100 | <1 | | | | | | |

[a]The unit for $EC_{50}$ and $IC_{50}$ is μM;
[b]The unit for $EC_{50}$ and $IC_{50}$ is μg/mL;
[c]Selectivity index is expressed as $IC_{50}/EC_{50}$;
[d]$EC_{90}$ = 11 μM, and $IC_{50}/EC_{90}$ = 35;
[e]$EC_{90}$ = 4.2 μM, and $IC_{50}/EC_{90}$ = 64;
[f]$EC_{90}$ = 16 μM, and $IC_{50}/EC_{90}$ = 124;
[g]against measles;
[h]against adenovirus type-1;
[i]against influenza A(H1N1).

EXAMPLE 40

Anti-CMV Activities of Calanolide Analogues Against Various Isolates in Plaque Reduction Assay Five calanolide analogues, prepared as described above, were further evaluated for their anti-HCMV activity in plaque reduction assay against various laboratory and clinical isolates (Towne, AD 169, E. Mann, Coffinan, and C9208). Laboratory procedures were as described in Example 39. The results are summarized in Table III below. All compounds tested exhibited activity against all isolates tested.

EXAMPLE 41

Anti-HBV Activities of Calanolide Analogues in Secondary Assay

Compounds (±)-15f and (±)-15a, prepared as described above, were investigated in a secondary assay against HBV. Laboratory procedures were as described in Example 39. The results are summarized in Table IV below. Compound (±)-15a was active in primary assay (HBV virion), and compound (±)-15f was active in both primary assay and secondary assay (HBV RI).

TABLE III

Anti-CMV Activities of Calanolide Analogues against Various Isolates in Plaque Reduction Assay

| | (+)-7[a] | | | (±)-7[a] | | | (±)-7a[a] | | | (−)-calanolide B[a] | | | (−)-23a | | |
|---|---|---|---|---|---|---|---|---|---|---|---|---|---|---|---|
| Isolate | $EC_{50}$ | $MTC^b$ | $TI^c$ | $EC_{50}$ | $MTC^b$ | $TI^c$ | $EC_{50}$ | $MTC^b$ | $TI^c$ | $EC_{50}$ | $MTC^b$ | $TI^c$ | $EC_{50}$ | $MTC^b$ | $TI^c$ |
| Towne | 5.02 | >100 | >20 | 3.34 | >100 | >30 | 3.08 | 10 | 3.2 | 3.20 | <100 | <31 | 3.16 | 10 | 3.2 |
| AD169 | 3.16 | 100 | 32 | 3.16 | 100 | 32 | 3.16 | 10 | 3.2 | 3.16 | 10 | 3.2 | 3.16 | 10 | 3.2 |
| E. Mann | 4.65 | 100 | 22 | 3.16 | 100 | 32 | 3.16 | 10 | 3.2 | 3.16 | 10 | 3.2 | 3.16 | 10 | 3.2 |
| Coffman | 4.78 | >100 | >21 | 3.34 | >100 | >30 | 3.16 | 10 | 3.2 | 3.18 | <100 | <31 | 3.16 | <100 | <32 |
| C9208 | 4.91 | >100 | >20 | 7.16 | 100 | 14 | 2.60 | 10 | 3.8 | 2.01 | 10 | 3.3 | 2.99 | 10 | 3.3 |

[a]The unit for $EC_{50}$ and MTC is μM;
[b]The minimum drug concentration that reduced cell viability by 25%;
[c]TI is $MTC/EC_{50}$.

TABLE IV

Anti-HBV Activities of Calanolide Analogues in Secondary Assay

| Compound | HBV Virion[a] | | | | HBV RT[a] | | | |
|---|---|---|---|---|---|---|---|---|
| | $EC_{50}$ | $EC_{90}$ | $IC_{50}$ | SI[b] | $EC_{50}$ | $EC_{90}$ | $IC_{50}$ | SI[b] |
| (±)-15f | 0.81 | 5.0 | 303 | 61 | 5.7 | 15 | 303 | 20 |
| (±)-15a | 2.8 | 20 | 1789 | 89 | >30 | >30 | 1789 | <60 |

[a]The unit for $EC_{50}$, $EC_{90}$ and $IC_{50}$ is μM;
[b]SI is $IC_{50}/EC_{90}$.

References

1a. Brookmeyer, R., Reconstruction and Future Trends of the AIDS Epidemic in the United States, *Science*, 1991, 253, 37–42.
b. Brain, M. M.; Heyward, W. L.; Curran, J. W., The Global Epidemiology of HIV Infection and AIDS, *Annu. Rev. Microbiol.*, 1990, 44, 555–577.
2a. Weislow, O. S.; Kiser, R.; Fine, D. L.: Bader, J. Shoemaker, R. H.; Boyd, M. R., New Soluble-formazan Assay for HIV-1 Cytopathic Effects: Application to High-Flux Screening of Synthetic and Natural Products of AIDS-Antiviral Activity. *J Natl. Cancer Inst.*, 1989, 81, 577–586.
b. Mitsuya, H.; Yarchoan, R.; Broder, S., Molecular Targets for AIDS Therapy. *Science*, 1990, 249, 1533–1544.
c. Petteway, S. R., Jr.; Lambert, D. M.; Metcalf, B. W., The Chronically Infected Cells: A Target for the Treatment of HIV Infection and AIDS. Trends *Pharmacol. Sci.*, 1991, 12, 28–34.
d. Richman, D. D., Antiviral Therapy of HIV Infection, *Annu. Rev. Med.*, 1991, 42, 69–90.
e. Haden, J. W., Immunotherapy of Human Immunodeficiency Virus Infection. *Trends Pharmacol Sci.*, 1991, 12, 107–111.
f. Huff, J. R., HV Protease: A Novel Chemotherapeutic Target for AIDS. *J Med. Chem.*, 1991, 34, 2305–2314.
g. De Clercq, E., HV Inhibitors Targeted at the Reverse Transcriptase. *AIDS Research and Human Retroviruses*, 1992, 8, 119–134.
3. Kashman, Y.; Gustafson, K. R.; Fuller, R. W.; Cardellina, J. H., II; McMahon; J. B.; Currens, M. J.; Buckheit, R. W., Jr.; Hughes, S. H.; Cragg, G. M.; Boyd, M. R., The Calanolides, a Novel HIV-Inhibitory Class of Coumarin Derivatives from the Tropical Rainforest Tree, *Calophyllum lanigerum*. *J Med. Chem.* 1992, 35, 2735–2743.
4. Boyd, M. R., National Cancer Institute, Personal Communication.
5. Chenera, B.; West, M. L.; Finkelstein, J. A.; Dreyer, G. B., Total Synthesis of (±)-Calanolide A, a Non-Nucleoside Inhibitor of HIV-1 Reverse Transcriptase. *J Org. Chem.* 1993,58, 5605–5606.
6. Sethna, S.; Phadke, R., The Pechlnanm Reaction. *Org. React.*, 1953, 7, 1–58 and references cited therein.
7a. Hughes, D. L., The Mitsunobu Reaction. *Org. React.*, 1992, 42, 335–656 and references cited therein.
7b. Mitsunobu, O., The Use of Diethyl Azodicarboxylate and Triphenylphosphine in Synthesis and Transformation of Natural Products. *Synthesis*, 1981, 1–28.
7c. Castro, B. R., Replacement of Alcoholic Hydroxyl Groups by Halogens and Other Nucleophiles via Oxyphosphonium Intermediates. *Org. React.* 1983, 29, 1–162.
7d. Hudlicky, M., Fluorination with Diethylaminosulfur Trifluoride and Related Aminofluorosulfuranes. *Org. React.* 1988, 35, 513–637.
8. Gemal, A. L.; Luche, J. L., Lanthanoids in Organic Synthesis. 6. The Reduction of α-Enones by Sodium Borohydride in the Presence of Lanthanoid Chlorides: Synthetic and Mechanistic Aspects. *J Am. Chem. Soc.*, 1981, 103, 5454–5459.
9a. Feuer, H.; Vincent, B. F., Jr.; Bartlett, R. S., The Reduction of Oximes with Diborane. A New Synthesis of N-Monosubstituted Hydroxylamines. *J Org. Chem.*, 1965, 30, 2877–2880.
9b. Feuer, H.; Braunstein, D. M., The Reduction of Oximes, Oxime Ethers, and Oxime Esters with Diborane. A Novel Synthesis of Amines. *J Org. Chem.*, 1969,34,1817–1821.
9c. Borch, R. F.; Bernstein, M. D.; Durst, H. D., The Cyanohydridoborate Anion as a Selective Reducing Agent. *J Amer. Chem. Soc.*, 1971, 93, 2897–2904.
10. For a review, see Nielsen, A. T.; Houlihan, W. J., The Aldol Condensation. *Org. React.* 1968, 16, 1–438.
11. For reviews, see:
 (a) Mukaiyama, T., The Directed Aldol Reaction. *Org. React.* 1982, 28, 203–331.
 (b) Reetz, M. T., Chelation or Non-Chelation Control in Addition Reactions of Chiral α-and β-Alkoxy Carbonyl Compounds, *Angew. Chem. Int. Ed.* Eng. 1984, 23, 556–569.
 (c) Shibata, I.; Baba, A., Organotin Enolates in Organic Synthesis. *Org. Prep. Proc. Int.* 1994, 26, 85–100.
12. For a review on chiral titanium complexes, see Duthaler, R. O.; Hafter, A., Chiral Titanium Complexes for Enantioselective Addition of Nucleophiles to Carbonyl Groups. *Chem. Rev.*, 1992, 92, 807–832 and reference cited therein.
13. For a review on chiral boron complexes, see Paterson, L.; Goodman, J. M.; M., Aldol Reactions in Polypropionate Synthesis: High π-Face Selectivity of Enol Borinates from α-Chiral Methyl and Ethyl Ketones under Substrate Control. *Tetrahedron Lett.* 1989, 30, 7121–7124 and references cited therein.
14. Tsunoda, T.; Yamamiya, Y.; Kawamura, Y.; Ito, S., Mitsunobu Acylation of Sterically Congested Secondary Alcohols by N,N,N',N'-Tetramethylazodicarboxamide-Tributylphosphine Reagents. *Tetrahedron Lett.* 1995, 36, 2529–2530.
15. Crombie, L.; Jones, R. C. F.; Palmer, C. J., Synthesis of the Mammea Coumarin. Part 1. The Coumarin of the Mannnea A, B, and C Series. *J Chem. Soc., Perkin Trans.* 1, 1987, 317–331.
16. Very recently, a similar work has been published in the literature; Cardellina, J. H., II; Bokesch, H. R.; McKee, T. C.; Boyd, M. R., Resolution and Comparative Anti-HIV Evaluation of the Enantiomers of Calanolides A and B. *Bioorg. Med. Chem. Lett.* 1995,5, 1011–1014.
17. Deshpande, P. P., Tagliaferri, F.; Victory, S. F.; Yan, S.; Baker, D. C., Synthesis of Optically Active Calanolides A and B. *J Org. Chem.* 1995, 60, 2964–2965.
18. Gulakowski, R. J.; McMahon, J. B.; Staley, P. G.; Moran, R. A.; Boyd, M. R., A serinautomated Multiparameter Approach for Anti-HIV Drug Screening, *J Virol. Methods*, 1991, 33, 87–100.
19. Larder, B. A.; Darby, G.; Richman, D. D., HIV with reduced Sensitivity to Zidovudine (AZT) isolated during Prolonged Therapy, *Science*, 1989, 243, 1731–1734.
20. Nunberg, J. H.; Schlief, W. A.; Boots, E. J.; O'Brien, J. A.; Quintero, J. C.; Hoffmnan, J. M.; Emini, E. A.; Goldman, M. E., Viral Resistance to Human Inununodeficiency Virus Type 1-specific Pyridinone Reverse Transcriptase, *J Virol.*, 1991, 65, 4887–4892.
21. Hoofnagle, J. H. Chronic hepatitis B, *N. Engl. J Med.* 1990, 323, 337–339.
22. Martin, P. and Friedman, L. S. In *Innovations in Antiviral Development and the Detection of Virus Infections*; T. M.

Block; D. Junkind; R. L. Crowell; M. Dension; L. R. Walsh, Ed.; Plenum Press: New York, 1992, 111–120.
23. Aach, R. D. The treatment of chronic type B viral hepatitis. *Ann. Intern. Med.* 1988, 109, 88–91.
24. Alexander, G. J.; Brahm, J.; Fagan, E. A.; Smith, H. M.; Daniels, H. M.; Eddleston, A. L.; Williams, R., Loss of HBSAg with interferon therapy in chronic hepatitis B virus infection. *Lancet* 1987, ii, 66–69.
25. Hoofniagle, J. H.; Di Bisceglie, A. M. Antiviral therapy of viral hepatitis. In *Antiviral Agents and Viral Diseases of Man;* G. J. Galasso; R. J. Whiteley; T. C. Merigan, Ed; Raven Press: New York, 1972, 415–457.
26. Yokosuka, O.; Omata, O. M.; Imazeki, F.; Okauda, K.; Summers, J. Changes of hepatitis B virus DNA in liver and serum caused by recombinant leukocyte interferon treatment: analysis of intrahepatic replicative hepatitis B virus DNA. *Hepatology* 1985,5,728–734.
27. Doong, S. L.; Tsai, C. H.; Schinazi, R. F.; Liota, D. C.; Cheng, Y. C. Inhibition of the replication of hepatitis B virus in vitro by 2',3'-dideoxy-3'-thiacytidine and related analogues. *Pro. Natl. Acad. Sci. USA* 1991, 88, 8495–99.
28. Schlam, S. W.; de Man, R. A.; Heijtink, R. A.; Niesters, G. M. New nucleoside analogues for chronic hepatitis B. *J Hepatalogy* 1995, 22, 52–56.
29. van Leeuwen R.; Katlama, C.; Kitchen, V.; Boucher, C. A. B.; Tubiana, R.; McBride, M.; Ingrand, D.; Weber, J.; Hill, A.; McDade, H.; Danner, S. A. Evaluation of safety and efficacy of 3TC (Lamivudine) in patients with asymptomatic or mildly symptomatic human immunodeficiency virus infection: A phase I/II study. *J Inf Dis.* 1995, 171, 1166–71.
30. Kaplan, M. M.; Webster, R. G. The epidemiology of influenza, *Sci. Am.,* 1977, 236(6), 88–105.
31. Hoffman, C. E. Amantadine HCl and related compounds. In *Selective Inhibitors of Viral Functions;* Carter, W. A., Ed.; CRC Press: Cleveland, 1973, 199.
32. Dolin, R.; Reichman, R. C.; Madore, H. P.; Maynard, R.; Lindon, P. M.; Webber-Jones, J. A controlled trial of amantadine and rimandatine in the prophylaxis of influenza A infections. *N. Engl. J Med.* 1982, 307, 580–584.
33. Oxford, J. S.; Galbraith, A. Anti-influenza virus activity of amantadine: A selective review of laboratory and clinical data: In *Viral Chemotherapy;* Shugar D. Ed.; Pergamon Press, 1985, 169–254.
34. Couch, R. B.; Jackson, G. G. Antiviral agents in influenza—Summary of influenza workshop VIII. *J Infect. Dis.* 1976, 134, 516–527.
35. Bryson, Y. J.; Monahan, C.; Pollack, M.; Shields, W. D. A prospective double-blind study of side effects associated with the administration of amantadine for influenza A virus prophylaxis. *J Infect. Dis.* 1980, 141, 543–547.
36. Tsunoda, A.; Maasab, H. H.; Cochran, K. W.; Eveland, W. C. Antiviral activity of α-methyl-1-adamantane methylamine hydrochloride. *Antimicrob. Agents Chemother.* 1966, 553.
37. Tisdale, M.; Bauer, D. J. The relative potencies of anti-influenza compounds. *Ann. N. Y. Acad. Sci.* 1977, 284,254–263.
38. Degelau, J; Somani, S. K.; Cooper, S. L.; Guay, D. R. P.; Crossley, K. B. Amantadine-resistant influenza A in a nursing facility. *Arch. Intern. Med.* 1992, 152, 390–392.
39. Hayden, F. G.; Belshe, R. B.; Clover, R. D.; Hay, A. J.; Oakers, M. G.; Soo, W. Emergence and apparent transmission of rimantadine-resistant influenza virus in families. *N. Engl. J Med.* 1989, 321, 1696–1702.
40. Mast, E. E.; Harmon, M. W.; Gravenstein, S.; Wu, S. P.; Arden, H. H.; Circo, R.; Tyszka, G.; Kendal, A. P.; Davis, J. P. Emergence and possible transmission of amantadine-resistant viruses during nursing home outbreaks of influenza A (H3N2). *Am J Epidemiol.* 1992, 134, 988–997.
41. Hayden, F. G.; Couch, R. B. Clinical and epidemiological importance of influenza A viruses resistant to amantadine and rimantadine. *Rev. Med. ViroL,* 1992, 2, 89–96.
42. Kimberlin, D. W.; Crampacker, C. S.; Straus, S. E.; Biron, K. K.; Drew, W. L.; Hayden, F. G.; McKinlay, M.; Richman, D. D.; Whitley, R. J. Antiviral resistance in clinical practice. *Antiviral Res.,* 1995, 26, 423–438.
43. Knight, V.; Gilbert, B. E. Ribavirin aerosol treatment of influenza. In *Infectious Disease Clinics of North America,* Vol 1.; Moellering, Jr. Ed.; 1987, 441–57.
44. Ray, C. G.; Icenogle, T. B.; Minnich, L. L; Copeland, J. G.; Grogan, T. M. The use of intravenous ribavirin to treat influenza virus-associated acute myocarditis. *J Infect Dis.,* 1989, 159, 829–836.
45. Hoover, D. R.; Saah, A. J.; Bacellar, H.; Phair, J.; Detels, R.; Anderson, R.; Kaslow, R. A. Clinical manifestations of AIDS in the Era of *Pneumocysis* Prophylaxis. *N. Eng. J Med.* 1993,329, 1922–1926.
46. Studies of the Ocular Complications of AIDS Research Group, AIDS clinical Trials Group. Mortality in Patients with the Acquired Immunodeficiency Syndrome Treated with Either Foscarnet or Ganciclovir for Cytomegaloviruse Retinitis. *N. Eng. J Med.* 1992,326,213–220.
47. Gelb, C. D. In *The Human Herpesviruses,* New York, 1993, 288–300.
48. Dellamonica, P. et al. *Clin. Pharmacol.* 1991,10,301
49. Smith, J. Strategies against Herpes Simplex Virus. *Intl. Antiviral News* 1997, 5,223–225.

What is claimed is:
1. A compound of formula i:

wherein

R$_1$ and R$_2$ are independently ⋯ⅠⅠⅠⅠ or ◀.

2. The compound of claim 1, wherein R$_1$=⋯ⅠⅠⅠⅠ and R$_2$=◀.

3. The compound of claim 1, wherein R$_1$=◀ and R$_2$=⋯ⅠⅠⅠⅠ.

4. The compound of claim 1, wherein R$_1$=⋯ⅠⅠⅠⅠ and R$_2$=⋯ⅠⅠⅠⅠ.

5. The compound of claim 1, wherein R$_1$=◀ and R$_2$=◀.

6. 6,6,10,11-tetramethyl-4-propyl-2H,6H,12H-benzo[1,2-b:3,4-b':5,6-b"]tripyran-2,12-dione.

7. A compound of formula ii:

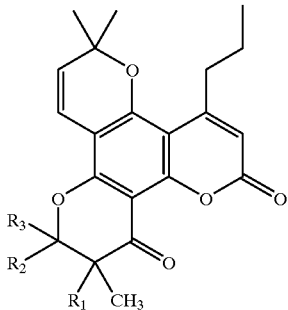

wherein $R_1$, $R_2$, and $R_3$ are independently H or $CH_3$.

8. The compound of claim 7, wherein $R_1$=H and $R_2$=$R_3$=$CH_3$.

9. The compound of claim 7, wherein $R_1$=$R_2$=$R_3$=H.

10. The compound of claim 7, wherein $R_1$=$R_2$=$CH_3$ and $R_3$=H.

11. A compound of formula iii:

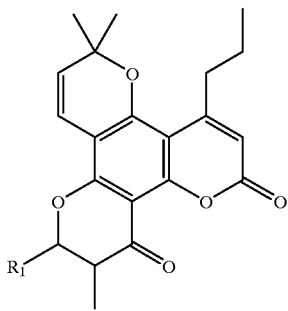

wherein $R_1$ is $C_1$–$C_6$ linear or branched alkyl.

12. The compound of claim 11, wherein $R_1$=ethyl.

13. The compound of claim 11, wherein $R_1$=isopropyl.

14. The compound of claim 11, having formula vi:

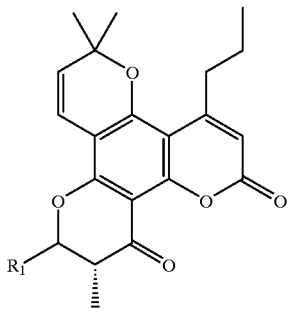

wherein $R_1$ is $C_1$–$C_6$ linear or branched alkyl.

15. The compound of claim 14, wherein $R_1$=ethyl.

16. The compound of claim 14, wherein $R_1$=isopropyl.

17. A compound of formula iv:

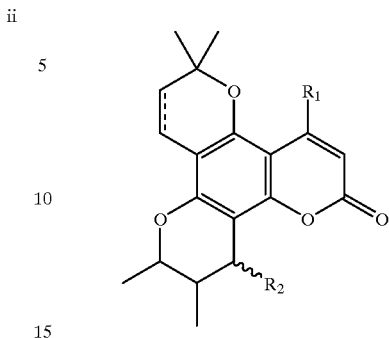

wherein $R_1$ is propyl orphenyl and $R_2$ is ·····IIIOH or ◂◼OH; with the proviso that the compound of formula iv is not (+)-costatolide, (+)-dihydrocostatolide, (+)-soulattrolide, or (+)-calanolide A.

18. The compound of claim 17, wherein $R_1$=propyl and $R_2$=◂◼OH.

19. The compound of claim 17, wherein $R_1$=phenyl and $R_2$=◂◼OH.

20. The compound of claim 17, wherein $R_1$=propyl and $R_2$=·····IIIOH.

21. The compound of claim 17, having formula vii:

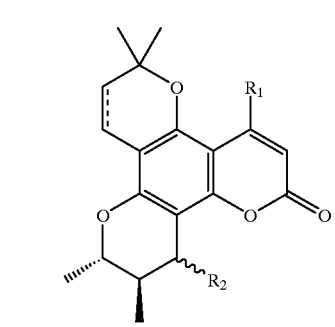

wherein $R_1$ is propyl or phenyl and $R_2$ is ·····IIIOH or ◂◼OH; with the proviso that the compound of formula vii is not (+)-costatolide, (+)-dihydrocostatolide, (+)-soulattrolide, or (+)-calanolide A.

22. The compound of claim 21, wherein $R_1$=propyl and $R_2$=◂◼OH.

23. The compound of claim 21, wherein $R_1$=phenyl and $R_2$=◂◼OH.

24. The compound of claim 21, wherein $R_1$=propyl and $R_2$=·····IIIOH.

25. A method of preventing or treating a viral infection comprising administering to a mammal an effective, non-toxic amount of at least one antiviral compound of the formula I:

I

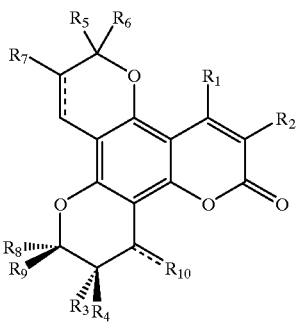

wherein
- $R_1$ is H, halogen, hydroxyl, amino, $C_{1-6}$ alkyl, aryl-$C_{1-6}$ alkyl, mono-or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;
- $R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;
- $R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;
- $R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocycle ring;
- $R_7$ is H, halogen, methyl, or ethyl;
- $R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_8$ and $R_9$ can be taken together to form a 5–7 membered saturated cycle ring or heterocyclic ring;
- $R_{10}$ is halogen, O, $OR_{11}$, $NOR_{11}$, $NHOR_{11}$, $NOR_{12}$, $NHOR_{12}$, $NR_{11}R_{12}$, $NR_{12}$, or $NR_{12}R_{13}$; wherein $R_{11}$ is H, acyl, $P(O)(OH)_2$, $S(O)(OH)_2$, $CO(C_{1-10}$ alkyl) $CO_2H$, $(C_{1-8}$ alkyl)$CO_2H$, $CO(C_{1-10}$ alkyl)$NR_{12}R_{13}$, $(C_{1-8}$ alkyl) $NR_{12}R_{13}$; $R_{12}$ and $R_{13}$ are independently selected from the group consisting of H, $C_{1-6}$ alkyl, aryl, and aryl-$C_{1-6}$ alkyl; and $R_{12}$ and $R_{13}$ can be taken together to form a 5–7 membered saturated heterocyclic ring containing said nitrogen; or a pharmaceutically acceptable salt thereof.

26. The method of claim 25, wherein the viral infection is from a virus selected from the group consisting of Hepatitis B, a herpes virus, or a respiratory virus.

27. The method of claim 26, wherein the herpes virus is Herpes Simplex Type 1, Herpes Simplex Type 2, Cytomegalovirus, Varicella Zoster Virus, or Epstein Barr Virus.

28. The method of claim 26, wherein the respiratory virus is Influenza A, Influenza B, Parainfluenza, Adenovirus, Measles, or Respiratory Syncytial Virus.

29. The method of claim 25, wherein the antiviral compound comprises formula i:

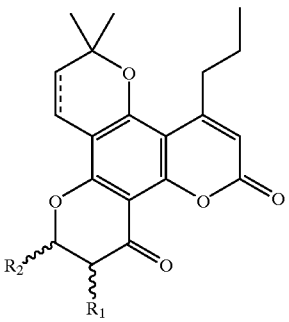

wherein $R_1$ and $R_2$ are independently ⋯⫼ or ◂.

30. The method of claim 29, wherein $R_1$=⋯⫼ and $R_2$=◂.

31. The method of claim 29, wherein $R_1$=◂ and $R_2$=⋯⫼.

32. The method of claim 29, wherein $R_1$=⋯⫼ and $R_2$=⋯⫼.

33. The method of claim 29, wherein $R_1$=◂ and $R_2$=◂.

34. The method of claim 29, wherein the viral infection is from a virus selected from the group consisting of Hepatitis B, a herpes virus, or a respiratory virus.

35. The method of claim 34, wherein the herpes virus is Herpes Simplex Type 1, Herpes Simplex Type 2, Cytomegalovirus, Varicella Zoster Virus, or Epstein Barr Virus.

36. The method of claim 34, wherein the respiratory virus is Influenza A, Influenza B, Parainfluenza, Adenovirus, Measles, or Respiratory Syncytial Virus.

37. The method of claim 30, wherein the viral infection is from a virus selected from the group consisting of Hepatitis B, Cytomegalovirus, Epstein Barr Virus, or measles.

38. The method of claim 25, wherein the antiviral compound comprises 6,6,10,11-tetramethyl-4-propyl-2H,6H,12H-benzo[1,2-b:3,4-b': 5,6-b"]tripyran-2,12-dione.

39. The method of claim 38, wherein the viral infection is from a virus selected from the group consisting of Hepatitis B, a herpes virus, or a respiratory virus.

40. The method of claim 39, wherein the herpes virus is Herpes Simplex Type 1, Herpes Simplex Type 2, Cytomegalovirus, Varicella Zoster Virus, or Epstein Barr Virus.

41. The method of claim 39, wherein the respiratory virus is Influenza A, Influenza B, Parainfluenza, Adenovirus, Measles, or Respiratory Syncytial Virus.

42. The method of claim 25, wherein the antiviral compound comprises formula ii:

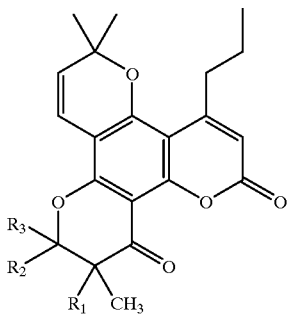

ii wherein $R_1$, $R_2$, and $R_3$ are independently H or $CH_3$.

43. The method of claim 42, wherein $R_1$=H and $R_2$=$R_3$=$CH_3$.

44. The method of claim 42, wherein $R_1$=$R_2$=$R_3$=H.

45. The method of claim 42, wherein $R_1$=$R_2$=$CH_3$ and $R_3$=H.

46. The method of claim 42, wherein the viral infection is from a virus selected from the group consisting of Hepatitis B, a herpes virus, or a respiratory virus.

47. The method of claim 46, wherein the herpes virus is Herpes Simplex Type 1, Herpes Simplex Type 2, Cytomegalovirus, Varicella Zoster Virus, or Epstein Barr Virus.

48. The method of claim 46, wherein the respiratory virus is Influenza A, Influenza B, Parainfluenza, Adenovirus, Measles, or Respiratory Syncytial Virus.

49. The method of claim 44, wherein the viral infection is from Hepatitis B.

50. The method of claim 45, wherein the viral infection is from Hepatitis B.

51. The method of claim 25, wherein the antiviral compound comprises formula iii:

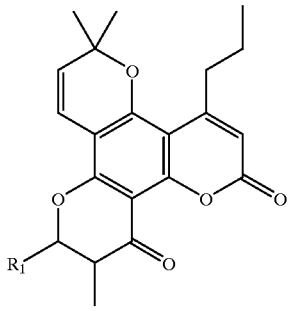

iii wherein $R_1$ is $C_1$–$C_6$ linear or branched alkyl.

52. The method of claim 51, wherein $R_1$=ethyl.

53. The method of claim 51, wherein $R_1$=isopropyl.

54. The method of claim 51, wherein the viral infection is from a virus selected from the group consisting of Hepatitis B, a herpes virus, or a respiratory virus.

55. The method of claim 54, wherein the herpes virus is Herpes Simplex Type 1, Herpes Simplex Type 2, Cytomegalovirus, Varicella Zoster Virus, or Epstein Barr Virus.

56. The method of claim 54, wherein the respiratory virus is Influenza A, Influenza B, Parainfluenza, Adenovirus, Measles, and Respiratory Syncytial Virus.

57. The method of claim 51, wherein the antiviral compound comprises formula vi:

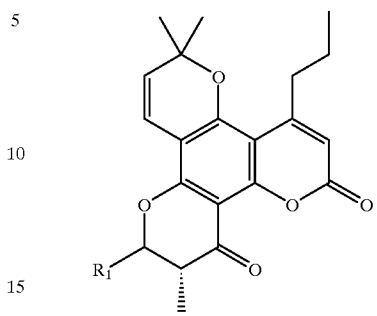

vi wherein $R_1$ is $C_1$–$C_6$ linear or branched alkyl.

58. The method of claim 57, wherein $R_1$=ethyl.

59. The method of claim 57, wherein $R_1$=isopropyl.

60. The method of claim 57, wherein the viral infection is from a virus selected from the group consisting of Hepatitis B, a herpes virus, or a respiratory virus.

61. The method of claim 60, wherein the herpes virus is Herpes Simplex Type 1, Herpes Simplex Type 2, Cytomegalovirus, Varicella Zoster Virus, or Epstein Barr Virus.

62. The method of claim 60, wherein the respiratory virus is Influenza A, Influenza B, Parainfluenza, Adenovirus, Measles, and Respiratory Syncytial Virus.

63. The method of claim 25, wherein the antiviral compound comprises formula iv:

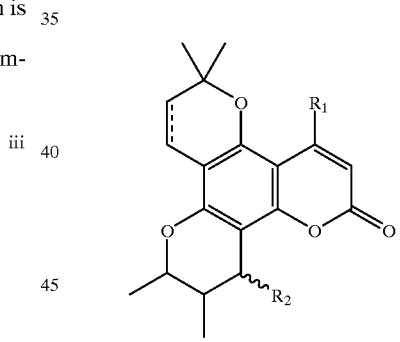

iv wherein $R_1$ is propyl or phenyl and $R_2$ is ''''''OH or ◂█OH.

64. The method of claim 63, wherein $R_1$=propyl and $R_2$=◂█OH.

65. The method of claim 63, wherein $R_1$=phenyl and $R_2$=◂█OH.

66. The method of claim 63, wherein $R_1$=propyl and $R_2$=''''''OH.

67. The method of claim 63, wherein the viral infection is from a virus selected from the group consisting of Hepatitis B, a herpes virus, or a respiratory virus.

68. The method of claim 67, wherein the herpes virus is Herpes Simplex Type 1, Herpes Simplex Type 2, Cytomegalovirus, Varicella Zoster Virus, or Epstein Barr Virus.

69. The method of claim 67, wherein the respiratory virus is Influenza A, Influenza B, Parainfluenza, Adenovirus, Measles, and Respiratory Syncytial Virus.

70. The method of claim 64, wherein the viral infection is from a virus selected from the group consisting of Hepatitis B or Cytomegalovirus.

71. The method of claim 63, wherein the antiviral compound comprises formula vii:

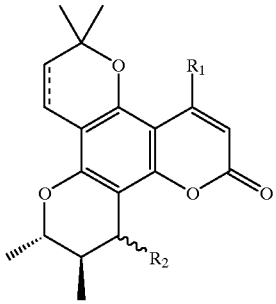

vii wherein $R_1$ is propyl or phenyl and $R_2$ is ·····ııııOH or ◂◂◂◂OH.

72. The method of claim 71, wherein $R_1$=propyl and $R_2$=◂◂◂◂OH.

73. The method of claim 71, wherein $R_1$=phenyl and $R_2$=◂◂◂◂OH.

74. The method of claim 71, wherein $R_1$=propyl and $R_2$·····ııııOH.

75. The method of claim 71, wherein the viral infection is from a virus selected from the group consisting of Hepatitis B, a herpes virus, or a respiratory virus.

76. The method of claim 75, wherein the herpes virus is Herpes Simplex Type 1, Herpes Simplex Type 2, Cytomegalovirus, Varicella Zoster Virus, or Epstein Barr Virus.

77. The method of claim 75, wherein the respiratory virus is Influenza A, Influenza B, Parainfluenza, Adenovirus, Measles, and Respiratory Syncytial Virus.

78. The method of claim 72, wherein the viral infection is from a virus selected from the group consisting of Hepatitis B or Cytomegalovirus.

79. The method of claim 25, which further comprises co-administering an effective therapeutic amount of at least one compound selected from the group consisting of a second antiviral compound, an immunostimulant, an immunomodulator, an antibiotic, or a chemokine inhibitor.

80. The method of claim 79, wherein the second antiviral compound is a protease inhibitor.

81. The method of claim 80, wherein the protease inhibitor is selected from the group consisting of indinavir, saquinavir, ritonavir, and nelfinavir.

82. The method of claim 79, wherein the second antiviral compound is a biflavanoid.

83. The method of claim 82, wherein the biflavanoid is selected from the group consisting of robustaflavone, amentoflavone, and a derivate or salt thereof.

84. The method of claim 79, wherein the second antiviral compound is selected from the group consisting of AZT, ddC, ddI, D4T, 3TC, acyclovir, gancyclovir, fluorinated nucleosides and nonnucleoside analog compounds such as TIBO derivatives and nevirapine, α-interfon, recombinant CD4, amantadine, rimantadine, ribavirin, and vidarabine.

85. The method of claim 79, wherein the immunostimulant is an interleukin or cytokine.

86. The method of claim 79, wherein the antibiotic is an antibacterial agent, antifungal agent, or anti-pneumocysitis agent.

87. A compound of the formula I:

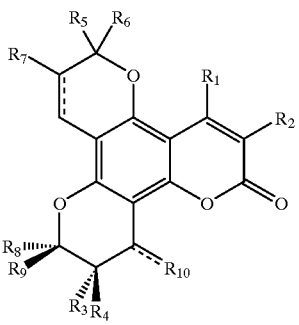

I wherein $R_1$ is H, halogen, hydroxyl, amino, $C_{1-6}$ alkyl, aryl-$C_{1-6}$ alkyl, mono-or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alky, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocycle ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_8$ and $R_9$ can be taken together to form a 5–7 membered saturated cycle ring or heterocyclic ring;

$R_{10}$ is halogen, O, $OR_{11}$, $NOR_{11}$, $NHOR_{11}$, $NOR_{12}$, $NHOR_{12}$, $NR_{11}R_{12}$, $NR_{12}$, or $NR_{12}R_{13}$; wherein $R_{11}$ is H, acyl, $P(O)(OH)_2$, $S(O)(OH)_2$, $CO(C_{1-10}$ alkyl) $CO_2H$, $(C_{1-8}$ alkyl)$CO_2H$, $CO(C_{1-10}$alkyl)$NR_{12}R_{13}$, $(C_{1-8}$ alkyl) $NR_{12}R_{13}$; $R_{12}$ and $R_{13}$ are independently selected from the group consisting of H, $C_{1-6}$ alkyl, aryl, and aryl-$C_{1-6}$ alkyl; and $R_{12}$ and $R_{13}$ can be taken together to form a 5–7 membered saturated heterocyclic ring containing said nitrogen; or a pharmaceutically acceptable salt thereof, alone or in combination with a carrier.

88. The compound of claim 87, having formula viii:

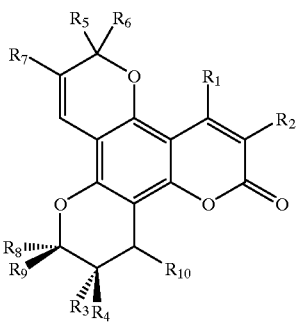

wherein
- $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-8}$ alkyl)amino-$C_{1-8}$ alkyl, nitro, azido or halogen;
- $R_2$ is H, halogen, hydroxyl, $C_{1-6}$ alkyl, aryl-$C_{1-6}$ alkyl, mono- or poly-fluorinated $C_{1-6}$ alky, aryl or heterocycle;
- $R_3$ and $R_4$ are independently selected from the group consisting of H, halogen, hydroxyl, amino, $C_1$alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;
- $R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle;
- $R_7$ is H, halogen, methyl, or ethyl;
- $R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_8$ and $R_9$ can be taken together to form a 5–7 membered saturated cycle ring or heterocyclic ring;
- $R_{10}$ is halogen, $OR_{11}$, $NHOR_{11}$, $NHOR_{12}$, $NR_{11}R_{12}$, $NR_{12}R_{13}$; wherein $R_{11}$ is H, acyl, $P(O)(OH)_2$, $S(O)(OH)_2$, $CO(C_{1-10}$ alkyl)$CO_2H$, $(C_{1-8}$ alkyl)$CO_2H$, $CO(C_{1-10}$ alkyl)$NR_{12}R_{13}$, $(C_{1-8}$ alkyl) $NR_{12}R_{13}$; $R_{12}$ and $R_{13}$ are independently selected from the group consisting of H and $C_{1-6}$ alkyl; and $R_{12}$ and $R_{13}$ can be taken together to form a 5–7 membered saturated heterocyclic ring containing said nitrogen;

or a pharmaceutically acceptable salt thereof, alone or in combination with a carrier; with the proviso that when $R_1$ is n-propyl or phenyl, $R_2$, $R_7$, and $R_8$ are H, $R_5$, $R_6$, and $R_9$ are methyl, and $R_{10}$ is OH, then $R_3$ and $R_4$ cannot both be H; when $R_1$ is n-propyl or phenyl, $R_2$, $R_4$, $R_7$, and $R_8$ are H, $R_5$, $R_6$, and $R_9$ are methyl, and $R_{10}$ is OH, then $R_3$ cannot be methyl; when $R_1$ is n-propyl or phenyl, $R_2$, $R_3$, $R_7$, and $R_9$ are H, $R_5$, $R_6$, and $R_8$ are methyl, and $R_{10}$ is OH, then $R_4$ cannot be methyl.

89. The compound of claim 88 wherein $R_3$ is methyl.
90. The compound of claim 89 wherein $R_4$ is methyl.
91. The compound of claim 90 wherein $R_8$ is H.
92. The compound of claim 91 wherein $R_9$ is methyl.
93. The compound of claim 92 wherein $R_1$ is phenyl.
94. The compound of claim 92 wherein $R_1$ is n-propyl.
95. The compound of claim 88, wherein $R_1$=n-propyl; $R_3=R_4=R_5=R_6=R_9$=methyl; $R_2=R_7=R_9$=H; and $R_{10}$=OH.
96. The compound of claim 88, wherein $R_1$=n-propyl; $R_3=R_4=R_5=R_6=R_8$=methyl; $R_2=R_7=R_9$=H; and $R_{10}$=OH.
97. The compound of claim 89 wherein $R_4$ is H.
98. The compound of claim 97 wherein $R_8$ is H.
99. The compound of claim 98 wherein $R_9$ is ethyl.
100. The compound of claim 99 wherein $R_1$ is phenyl.
101. The compound of claim 99 wherein $R_1$ is n-propyl.
102. The compound of claim 88, wherein $R_1$=n-propyl; $R_2=R_4=R_7=R_8$=H; $R_3=R_5=R_6$ methyl; $R_9$ ethyl; and $R_{10}$=OH.
103. The compound of claim 88, wherein $R_1$=n-propyl; $R_2=R_3=R_7=R_9$=H; $R_4=R_5=R_6$=methyl;$R_8$=ethyl; and $R_{10}$=OH.
104. The compound of claim 88, wherein $R_1$=n-propyl, $R_2=R_3=R_7=R_8$=H; $R_4=R_5=R_6$=methyl; $R_9$=ethyl; and $R_{10}$=OH.
105. The compound of claim 88, wherein $R_1$=n-propyl, $R_2=R_4=R_7=R_9$=H; $R_3=R_5=R_6$=methyl; $R_8$=ethyl; and $R_{10}$=OH.
106. The compound of claim 89 wherein $R_8$ is methyl.
107. The compound of claim 106 wherein $R_9$ is methyl.
108. The compound of claim 107 wherein $R_4$ is H.
109. The compound of claim 108 wherein $R_1$ is phenyl.
110. The compound of claim 108 wherein $R_1$ is n-propyl.
111. The compound of claim 108, wherein $R_1$=n-propyl; $R_2=R_4=R_7$=H; $R_3=R_5=R_6=R_8=R_9$=methyl; and $R_{10}$=OH.
112. The compound of claim 88, wherein $R_1$=n-propyl; $R_2=R_3=R_7$=H; $R_4=R_5=R_6=R_8=R_9$=methyl; and $R_{10}$=OH.
113. The compound of claim 87, having formula ix:

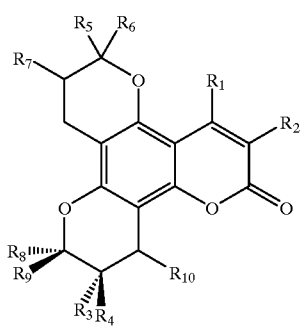

wherein
- $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;
- $R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocyclic ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{,1-8}$ alkyl, cyclohexyl, aryl or heterocycle; and $R_8$ and $R_9$ can be taken together to form a 5–7 membered saturated cycle ring or heterocyclic ring;

$R_{10}$ is halogen, $OR_{11}$, $NHOR_{11}$, $NHOR_{12}$, $NR_{11}R_{12}$, $NR_{12}R_{13}$; wherein $R_{11}$ is H, acyl, $P(O)(OH)_2$, $S(O)(OH)_2$, $CO(C_{1-10}$ alkyl)$CO_2H$, $(C_{1-8}$ alkyl)$CO_2H$, $CO(C_{1-10}$ alkyl)$NR_{12}R_{13}$, $(C_{1-8}$ alkyl) $NR_{12}R_{13}$; $R_{12}$ and $R_{13}$ are independently selected from the group consisting of H and $C_{1-6}$ alkyl; and $R_{12}$ and $R_{13}$ can be taken together to form a 5–7 membered saturated heterocyclic ring containing said nitrogen;

or a pharmaceutically acceptable salt thereof, alone or in combination with a carrier; with the proviso that when $R_1$ is n-propyl, $R_2$, $R_4$, $R_7$, and $R_8$ are H, $R_5$, $R_6$, and $R_9$ are methyl, and $R_{10}$ is OH, then $R_3$ cannot be methyl; when $R_1$ is n-propyl, $R_2$, $R_3$, $R_7$, and $R_9$ are H, $R_5$, $R_6$, and $R_8$ are methyl, and $R_{10}$ is OH, then $R_4$ cannot be methyl.

114. The compound of claim 87, having formula x:

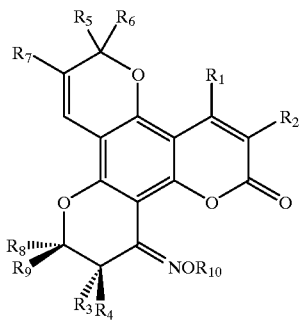

x wherein $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocycle ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_8$ and $R_9$ can be taken together to form a 5–7 membered saturated cycle ring or heterocyclic ring;

$R_{10}$ is H, $C_{1-6}$ alkyl, aryl and aryl-$C_{1-6}$ alkyl, acyl, $P(O)(OH)_2$, $S(O)(OH)_2$, $CO(C_{1-10}$ alkyl)$CO_2H$, $(C_{1-8}$ alkyl)$CO_2H$, $CO(C_{1-10}$ alkyl)$NR_{11}R_{12}$, $(C_{1-8}$ alkyl) $NR_{11}R_{12}$; wherein $R_{11}$ and $R_{12}$ are independently selected from the group consisting of H, $C_{1-6}$ alkyl, aryl, and aryl-$C_{1-6}$ alkyl; and $R_{11}$ and $R_{12}$ can be taken together to form a 5–7 membered saturated heterocyclic ring containing said nitrogen;

or a pharmaceutically acceptable salt thereof, alone or in combination with a carrier.

\* \* \* \* \*